(12) United States Patent
Giordani et al.

(10) Patent No.: US 9,174,966 B2
(45) Date of Patent: Nov. 3, 2015

(54) CRYSTALLINE FORMS OF 6-(1H-IMIDAZOL-1-YL)-2-PHENYLQUINAZOLINE

(75) Inventors: Antonio Giordani, Pavia (IT); Stefano Mandelli, Casatenovo (IT); Francesca Porta, Milan (IT); Matteo Ghirri, Milan (IT); Lucio Claudio Rovati, Monza (IT)

(73) Assignee: ROTTAPHARM S.P.A., Milan (IT)

( * ) Notice: Subject to any disclaimer, the term of this patent is extended or adjusted under 35 U.S.C. 154(b) by 0 days.

(21) Appl. No.: 13/375,816

(22) PCT Filed: Jun. 4, 2010

(86) PCT No.: PCT/IB2010/052496
§ 371 (c)(1),
(2), (4) Date: Dec. 2, 2011

(87) PCT Pub. No.: WO2010/140139
PCT Pub. Date: Dec. 9, 2010

(65) Prior Publication Data
US 2012/0142713 A1  Jun. 7, 2012

(30) Foreign Application Priority Data
Jun. 4, 2009  (IT) .............................. TO2009A0424

(51) Int. Cl.
C07D 403/04 (2006.01)
A61K 31/517 (2006.01)
A01N 43/54 (2006.01)

(52) U.S. Cl.
CPC ............... *C07D 403/04* (2013.01); *A01N 43/54* (2013.01); *A61K 31/517* (2013.01)

(58) Field of Classification Search
CPC ..... A01N 43/54; A61K 31/517; C07D 239/72
USPC ..................... 514/266.1, 266.2; 544/283, 284
See application file for complete search history.

(56) References Cited

FOREIGN PATENT DOCUMENTS

| WO | WO 2008/014822 | 2/2008 | |
|---|---|---|---|
| WO | WO2008/014822 | * 2/2008 | ........... C07D 401/04 |
| WO | WO 2009/152868 | 12/2009 | |

OTHER PUBLICATIONS

Amidon, G.L. et al., "A Theoretical Basis for a Bipharmaceutic Drug Classification: The Correlation of in Vitro Drug Product Dissolution and in Vivo Bioavailability," Pharm. Res. 12(3): 413-420 (1995).
Giron, Danielle, "Monitoring Polymorphism of Drugs, an On-Going Challenge—Part 2," American Pharmaceutical Review, 11(3), 86-90 (2008).
Brittain, Harry G., "X-ray Powder Diffraction of Pharmaceutical Materials," American Pharmaceutical Review, 5(1), 74-76 (2002).
Byrn, Stephen R. et al., "Regulatory Aspects of X-Ray Powder Diffraction," American Pharmaceutical Review, 8(3), 55-59 (2005).
Guillory J K ED, Brittain H G, "Generation of Polymorphs, Hydrates, Solvates, and Amorphous Solids," Polymorphism in Pharmaceutical Solids, Jan. 1, 1999, pp. 182-226.
International Search Report and Written Opinion issued in International Application No. PCT/IB2010/052496, mailed on Dec. 10, 2010.

* cited by examiner

*Primary Examiner* — Paul V Ward
(74) *Attorney, Agent, or Firm* — Pearl Cohen Zedek Latzer Baratz LLP

(57) ABSTRACT

The present invention relates to the solid state of 6-(1H-imidazol-1-yl)-2-phenylquinazoline (I) and therefore to novel crystalline forms of the base and of pharmaceutically acceptable salts and solvates thereof, and also to methods for preparing them, to the respective pharmaceutical formulations and to their therapeutic use.

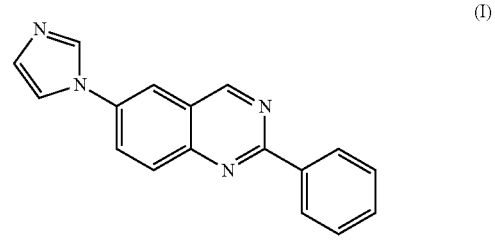

Compound (I) may be obtained as the free base in five different crystalline forms, three polymorphic forms and two hydrates. Some pharmaceutically acceptable salts of (I) that have physicochemical characteristics acceptable for pharmaceutical development were obtained, and the respective polymorphic forms and/or hydrates were characterized.

6 Claims, 66 Drawing Sheets

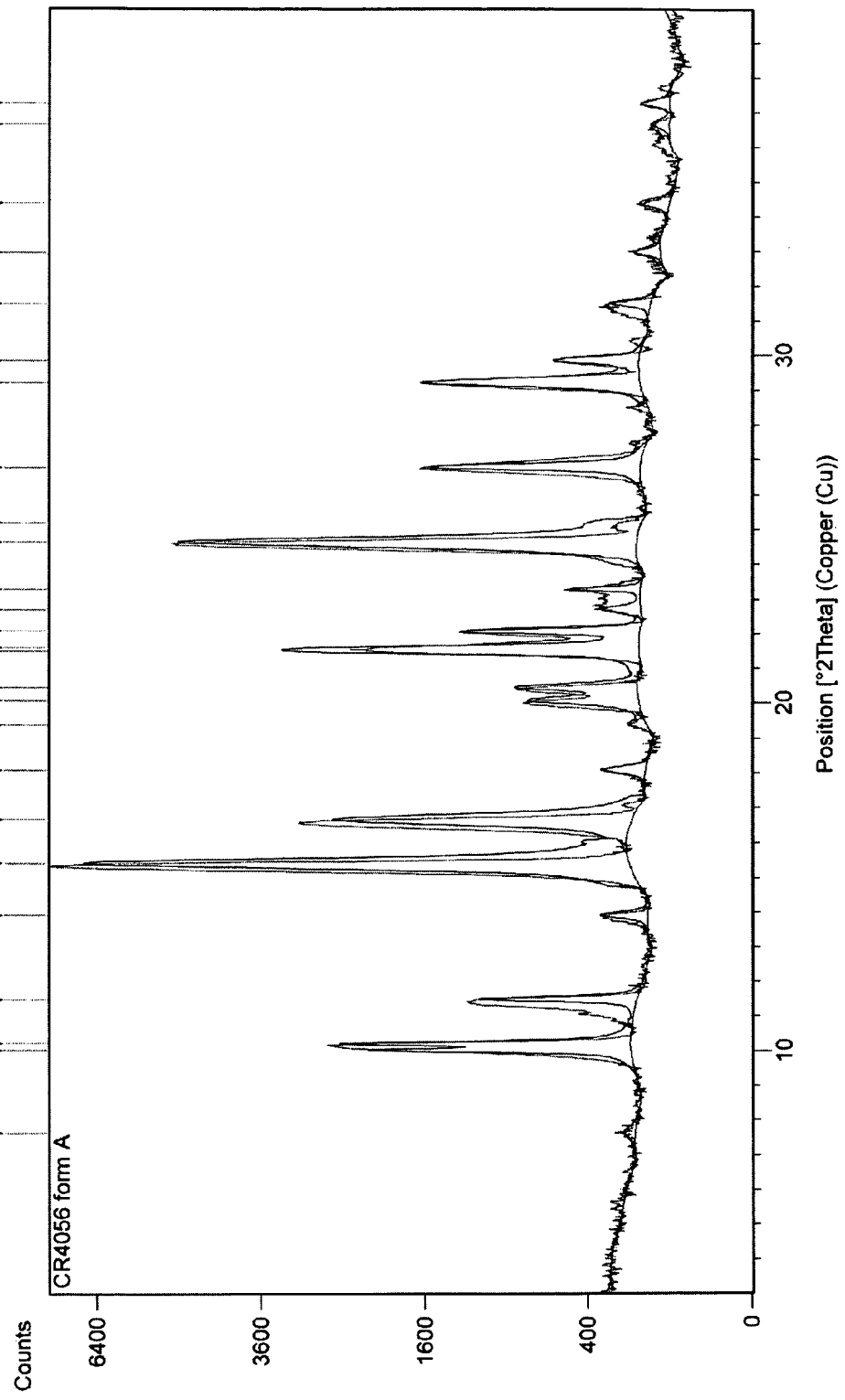

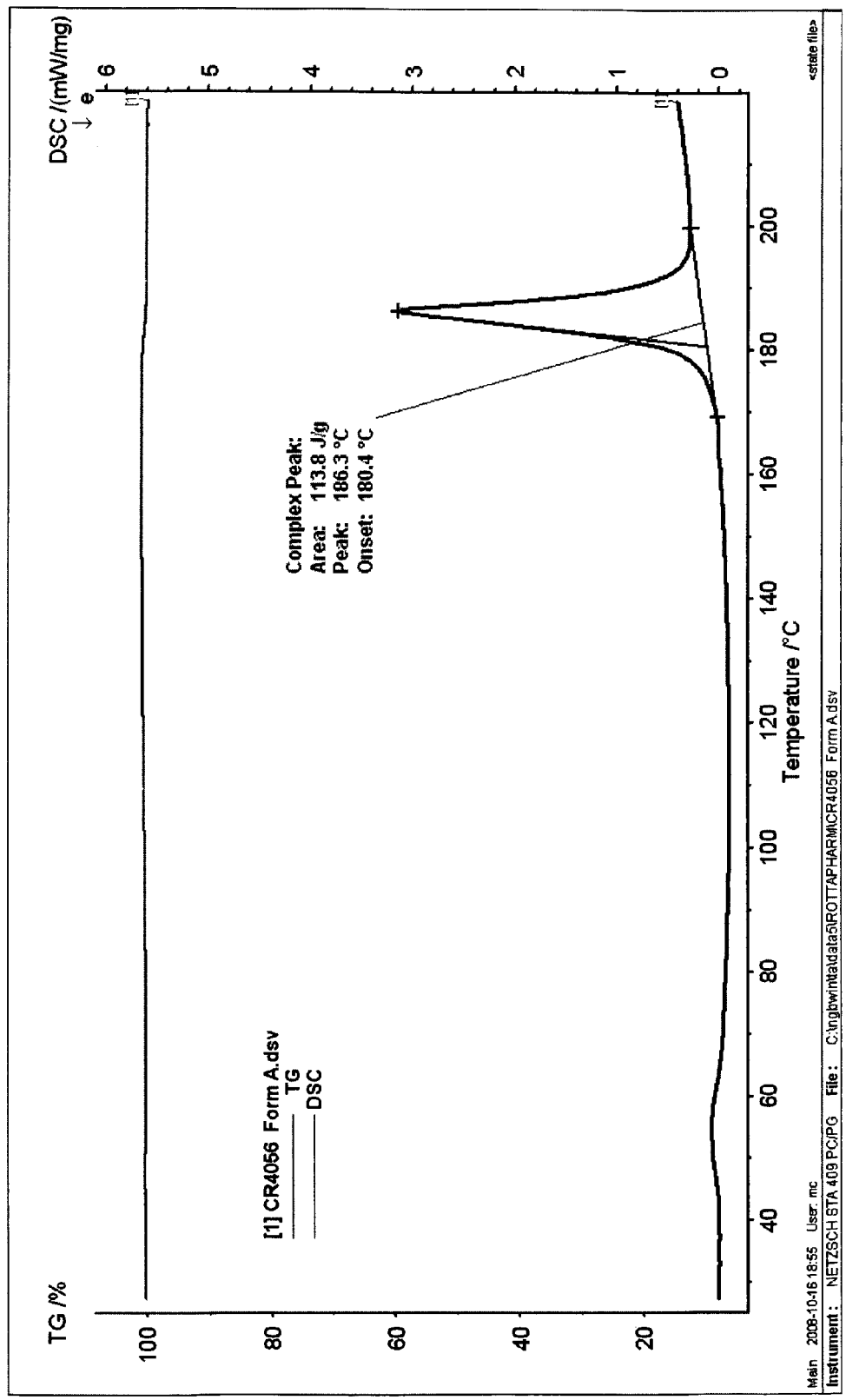
Figure 2: 6-(1H-imidazol-1-yl)-2-phenylquinazoline, Polymorph A, DSC

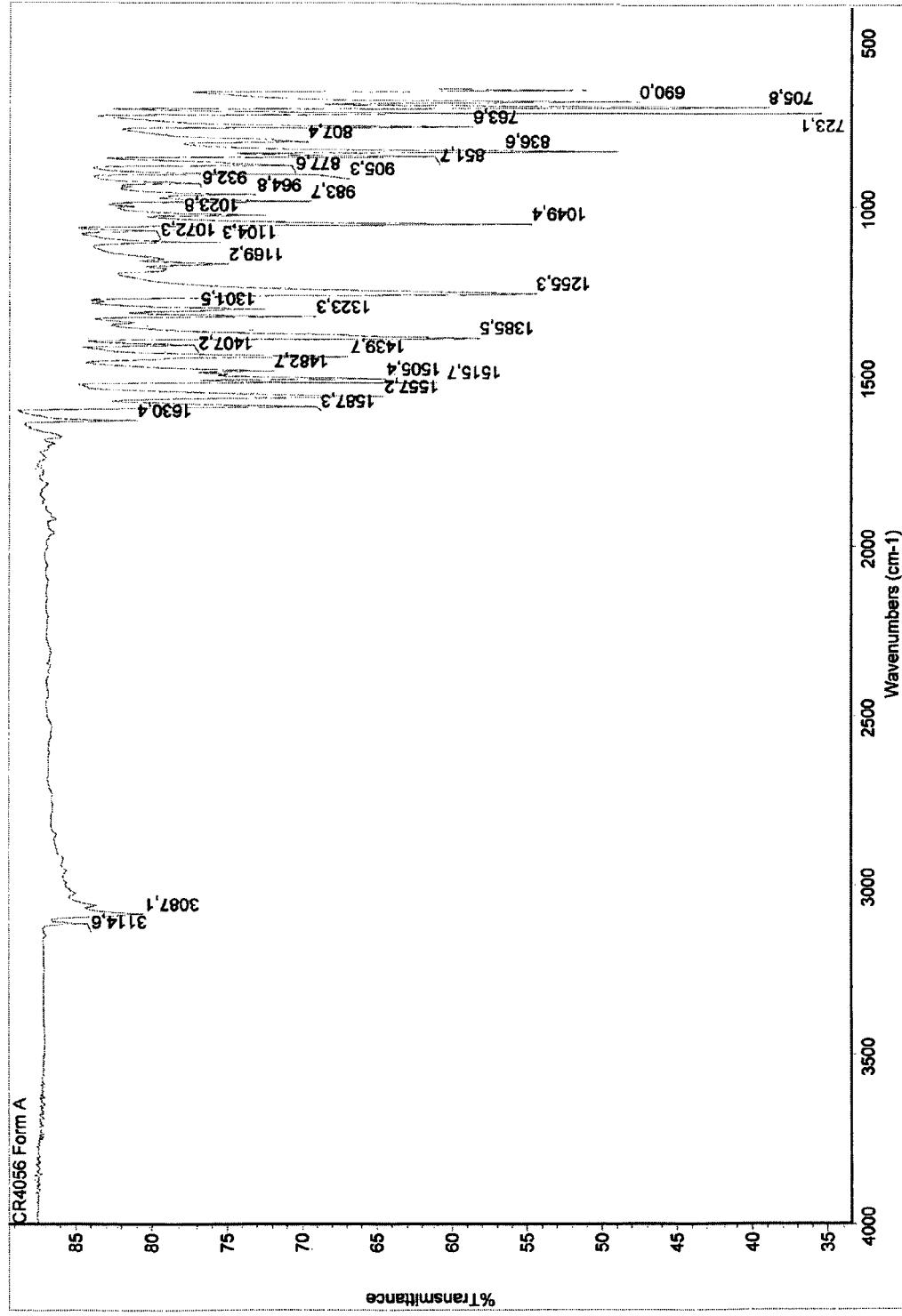

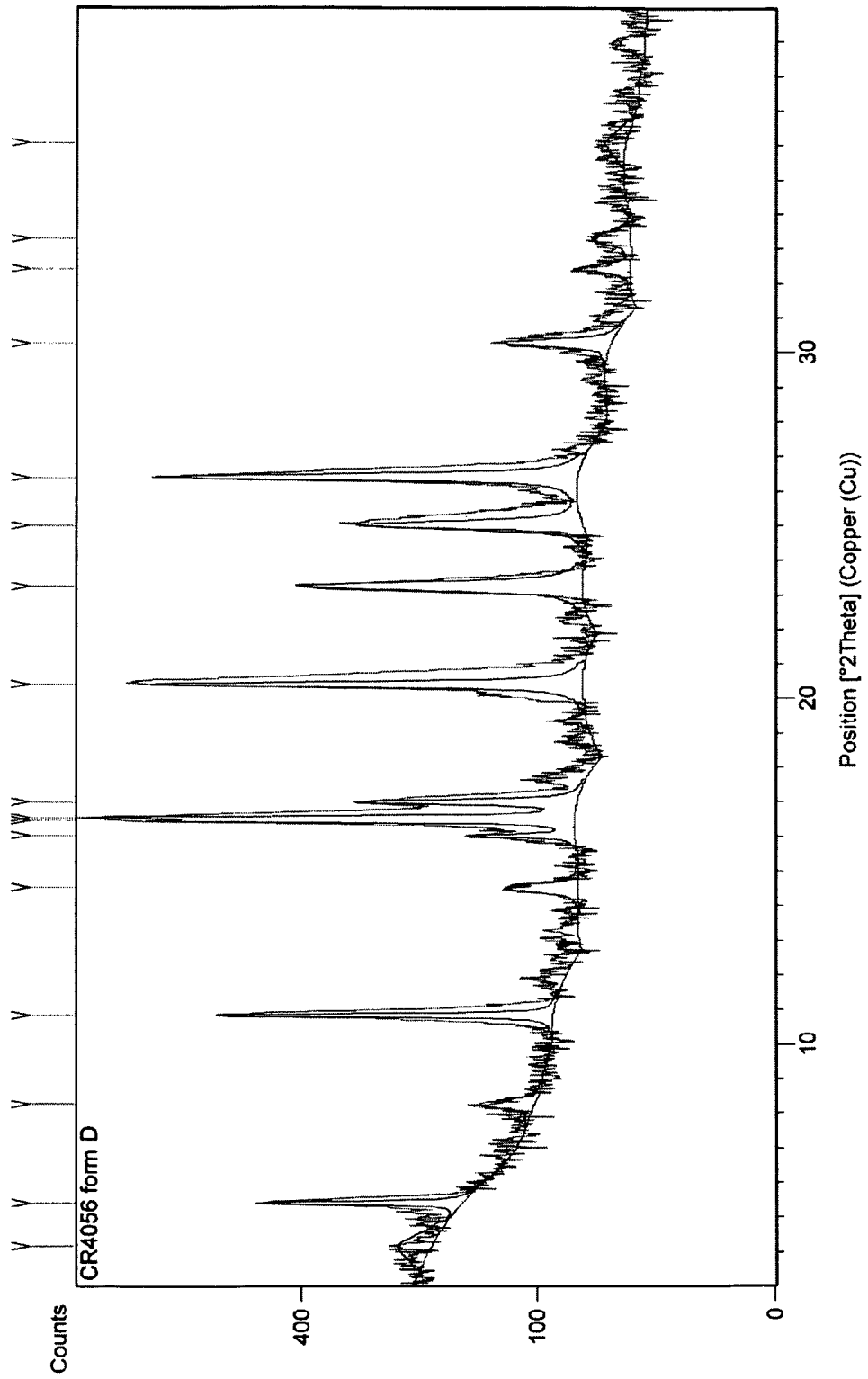

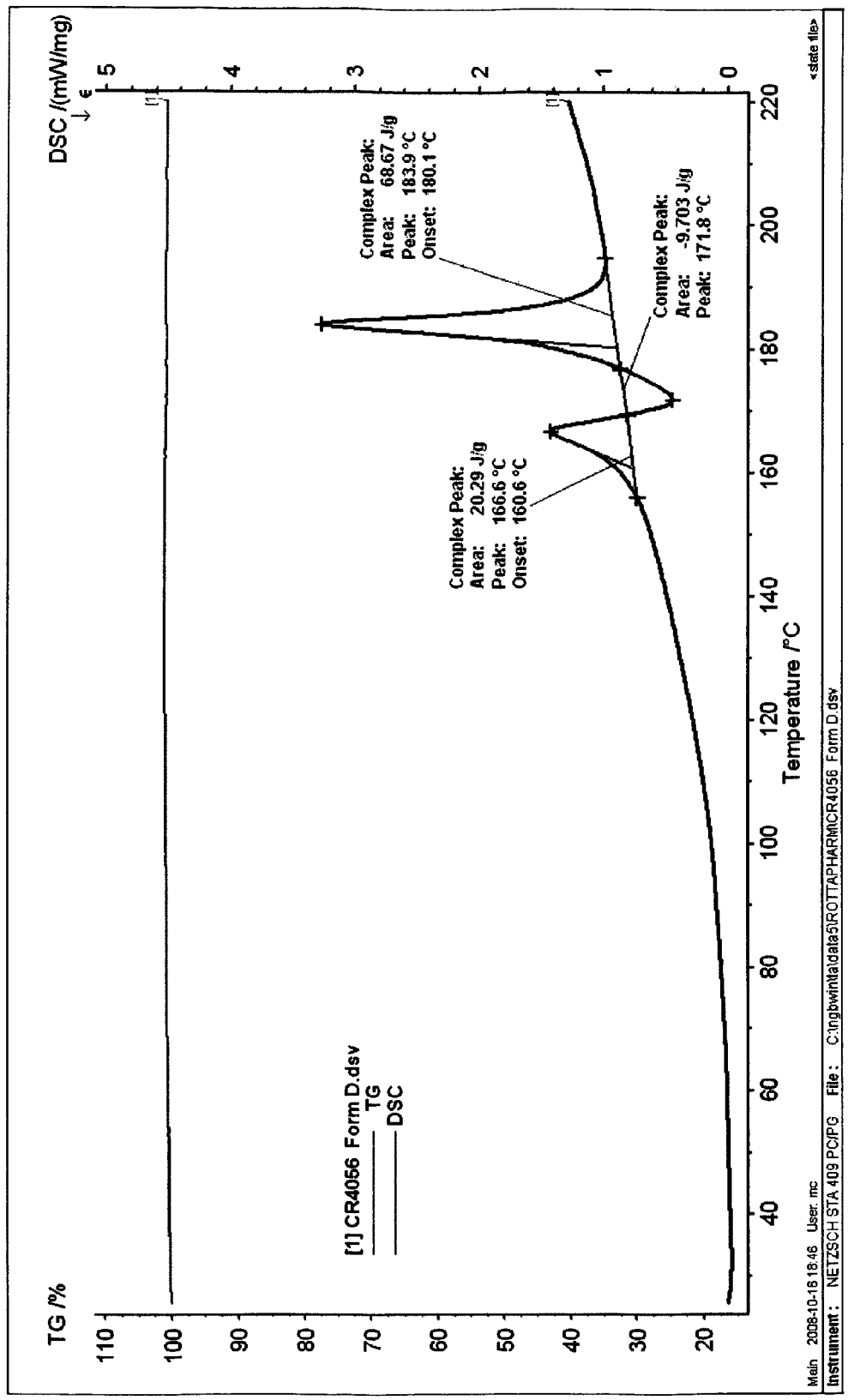
Figure 5: 6-(1H-imidazol-1-yl)-2-phenylquinazoline, Polymorph D, DSC

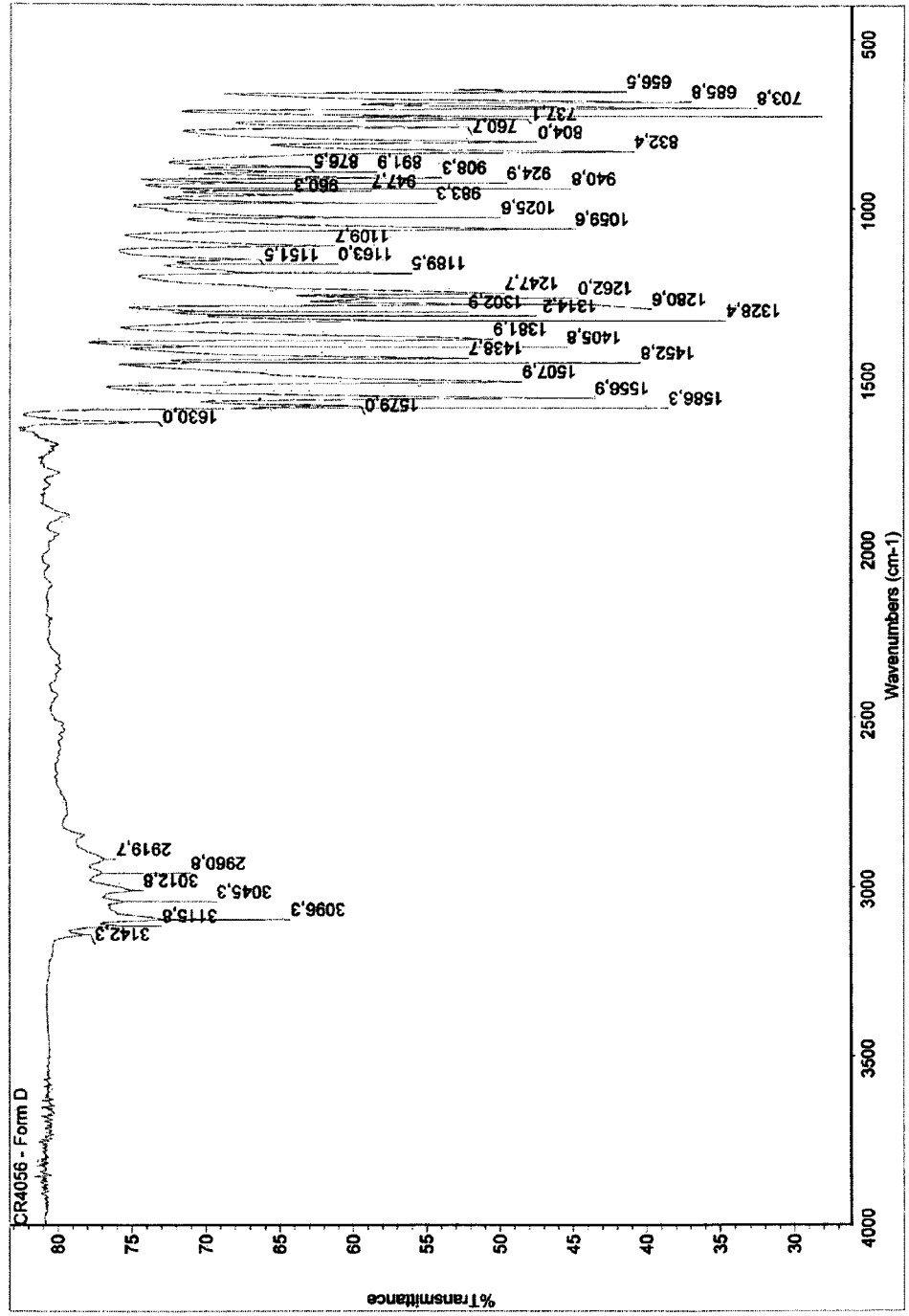
Figure 6: 6-(1H-imidazol-1-yl)-2-phenylquinazoline, Polymorph D, FT-IR

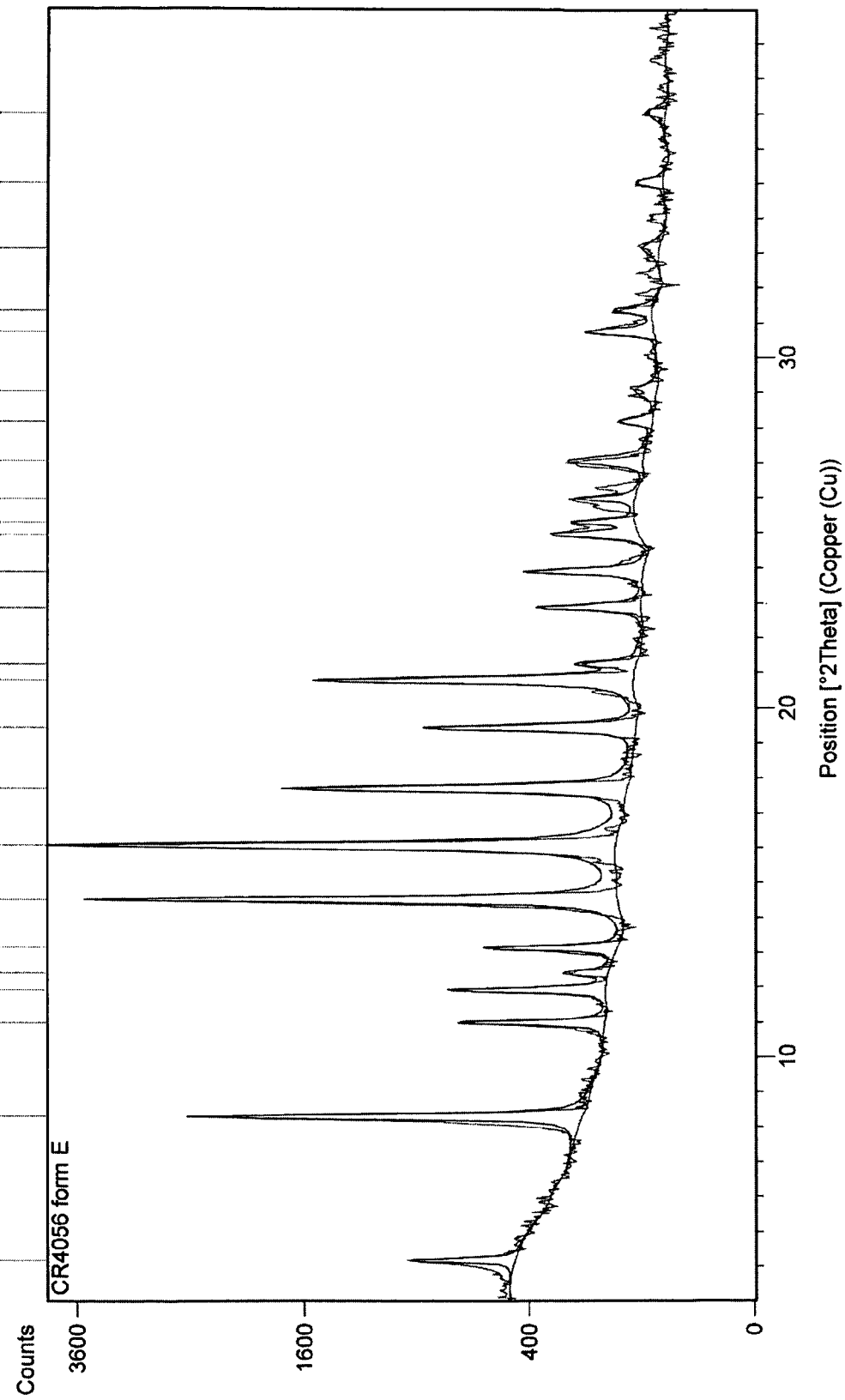

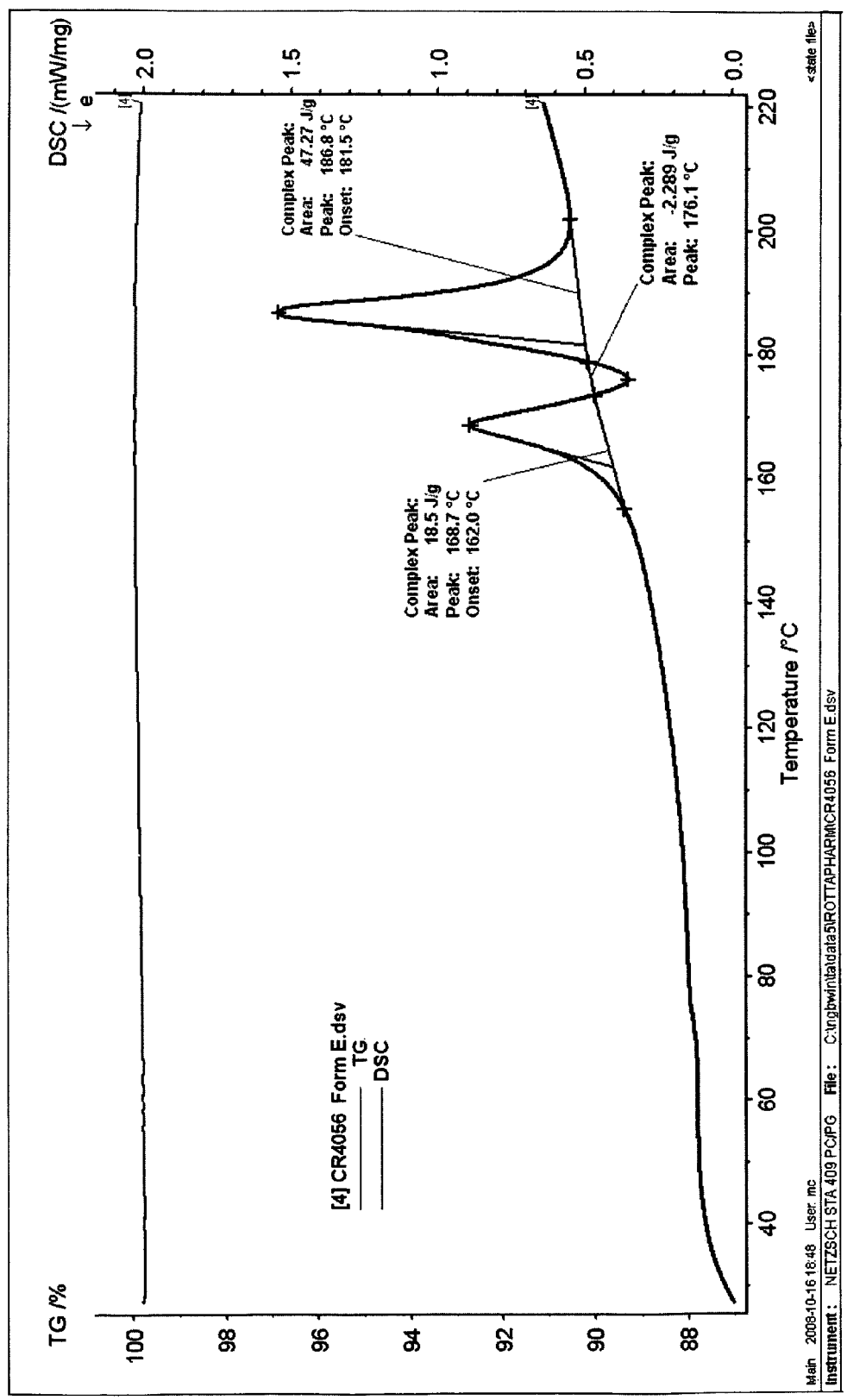
Figure 8: 6-(1H-imidazol-1-yl)-2-phenylquinazoline, Polymorph E, DSC

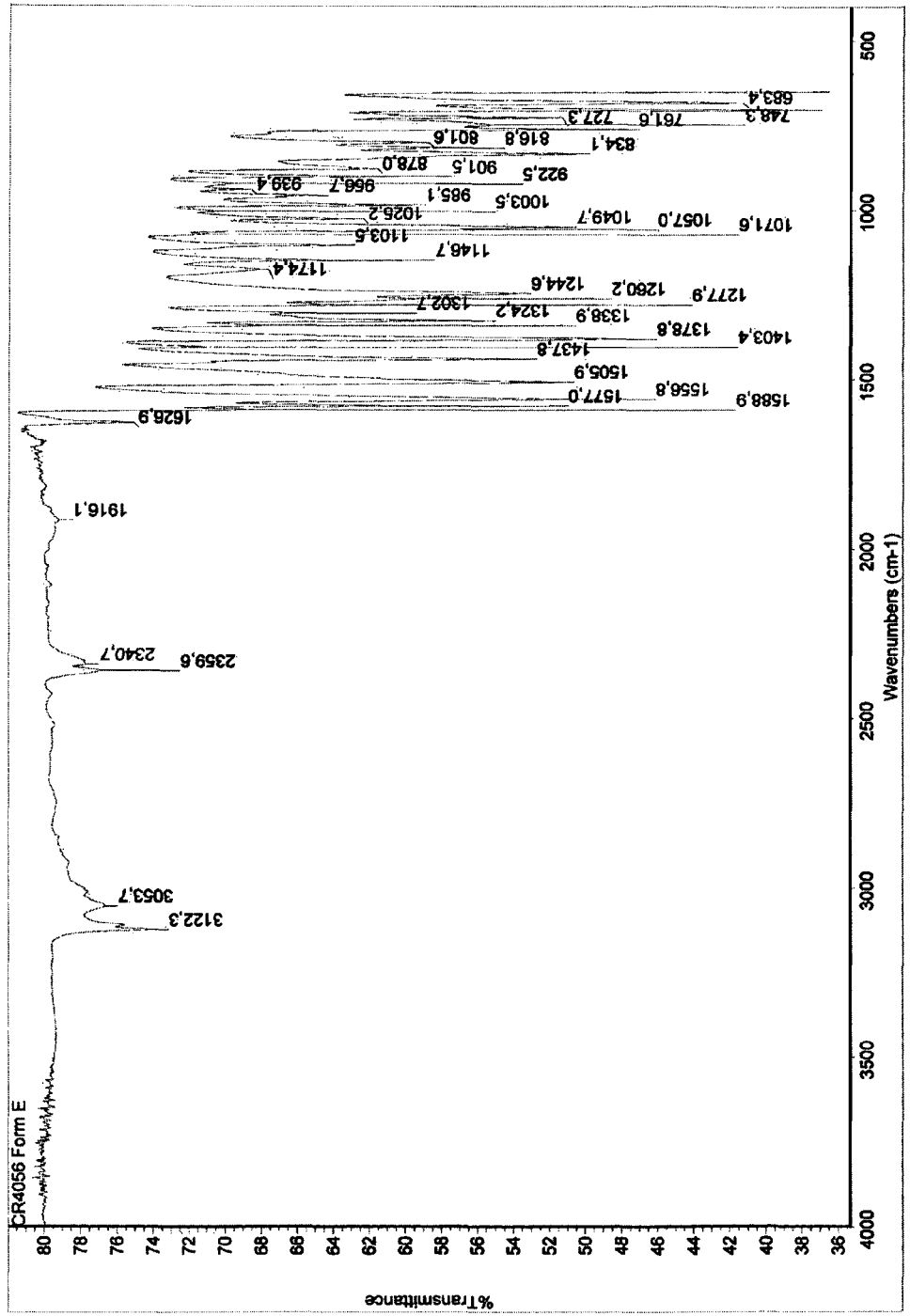

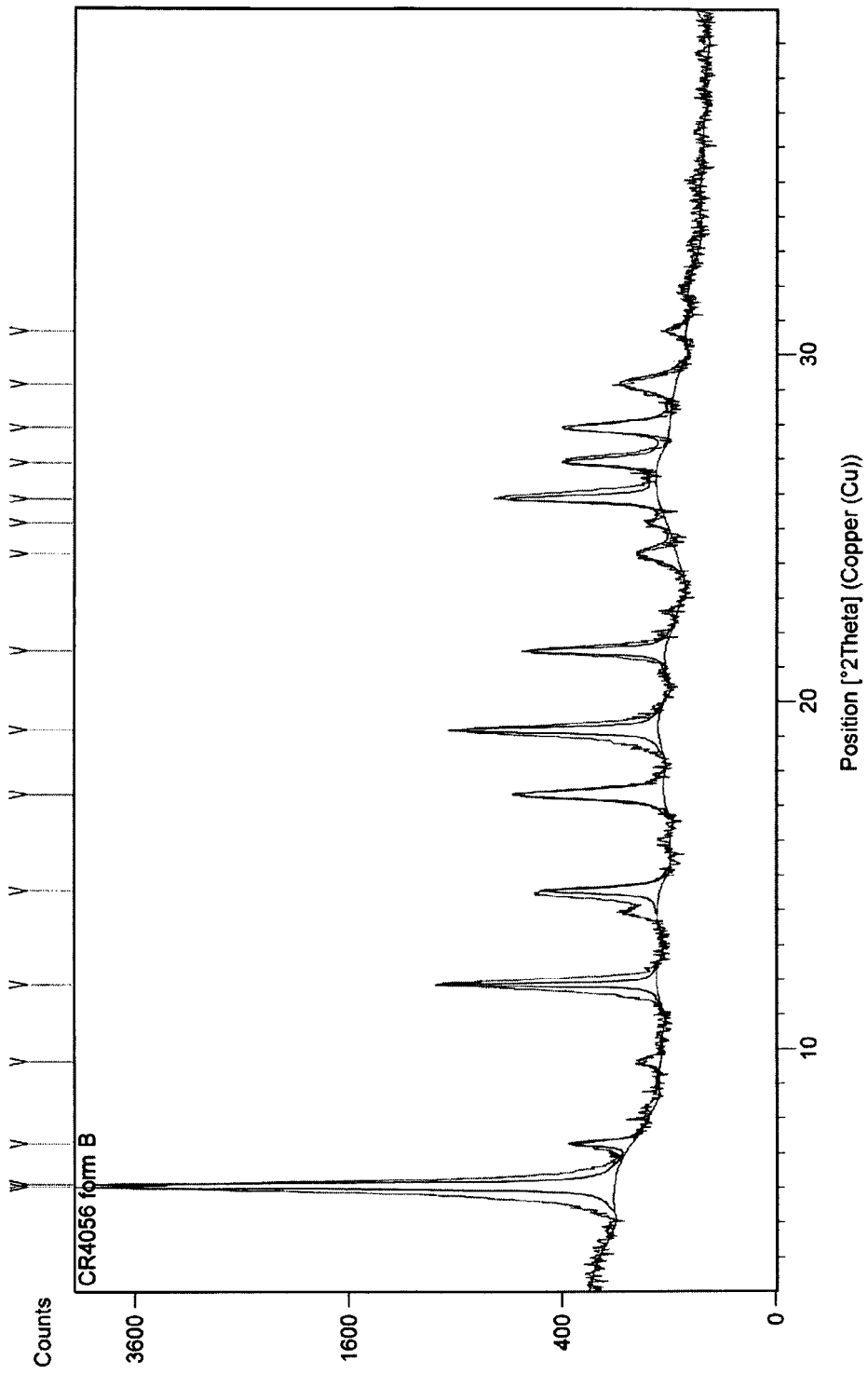

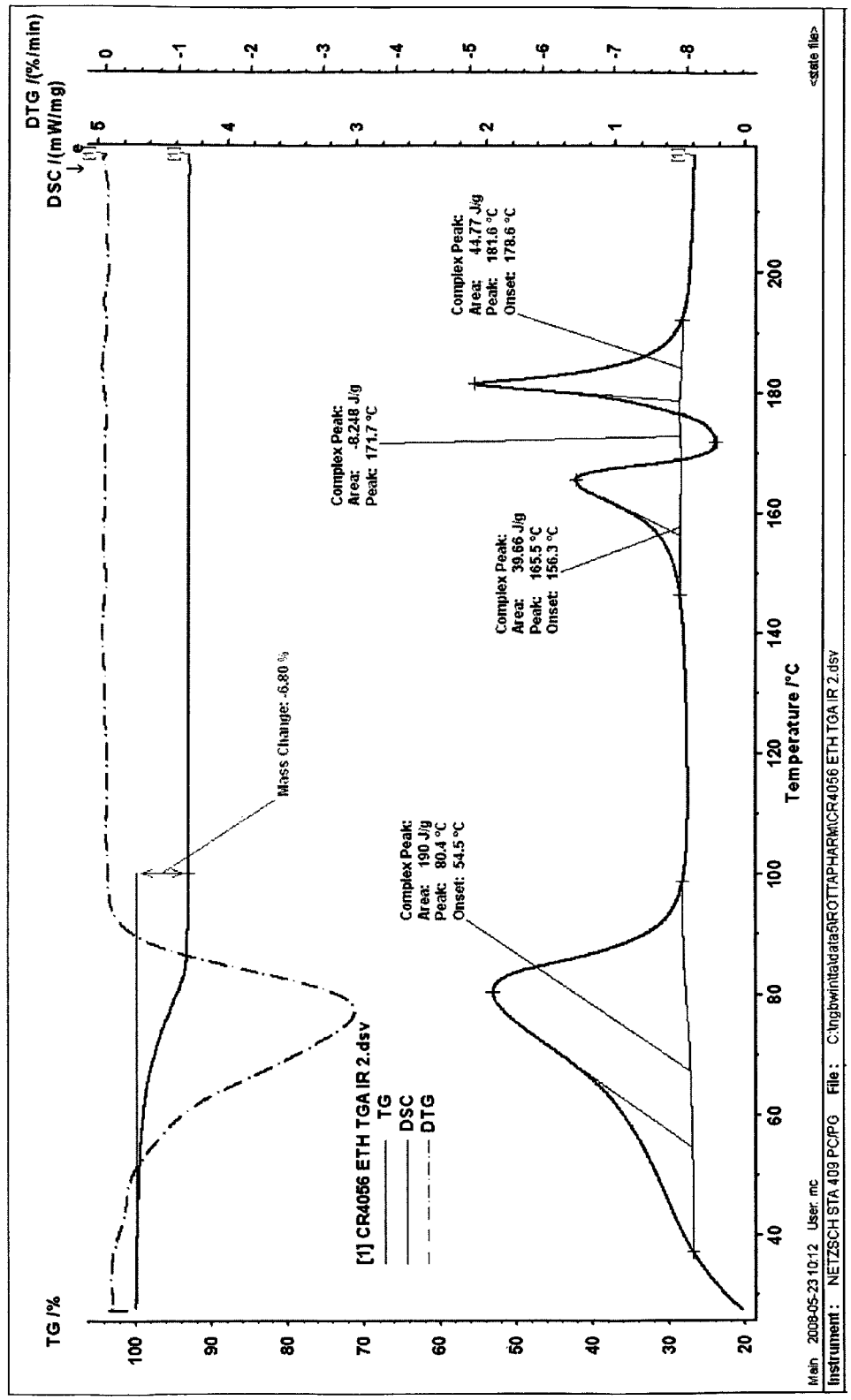
Figure 11: 6-(1H-imidazol-1-yl)-2-phenylquinazoline hydrate, form B, DSC

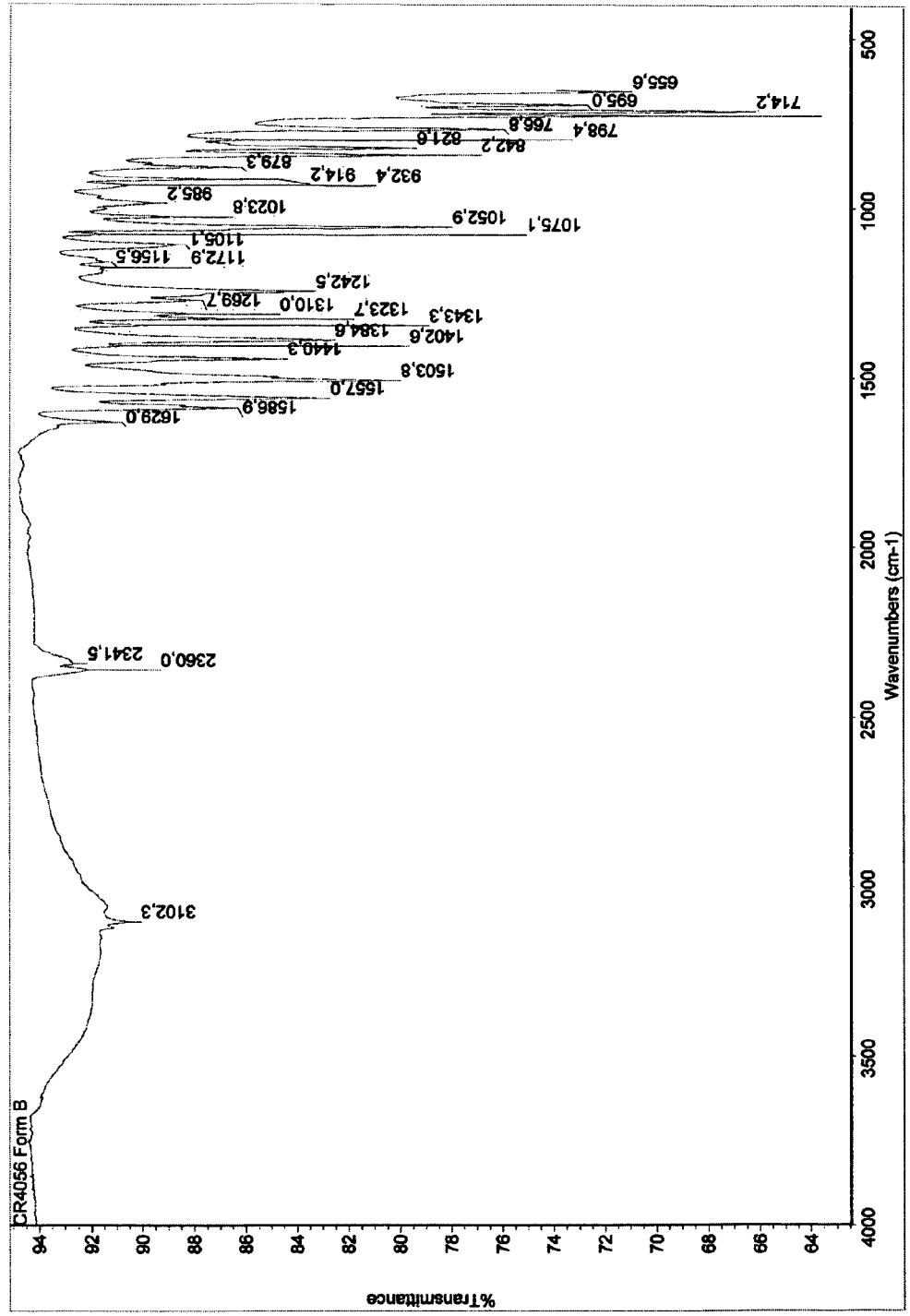

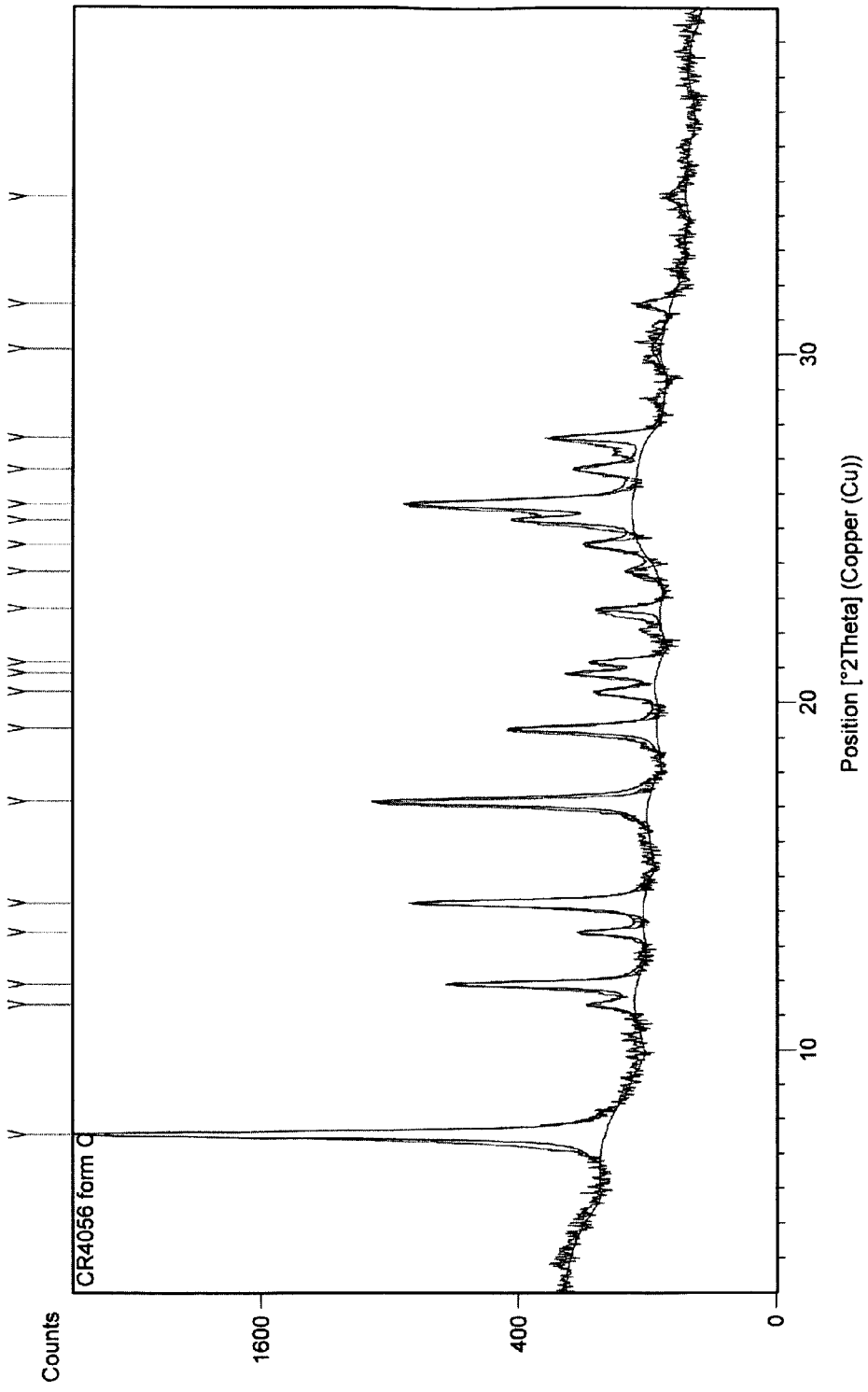

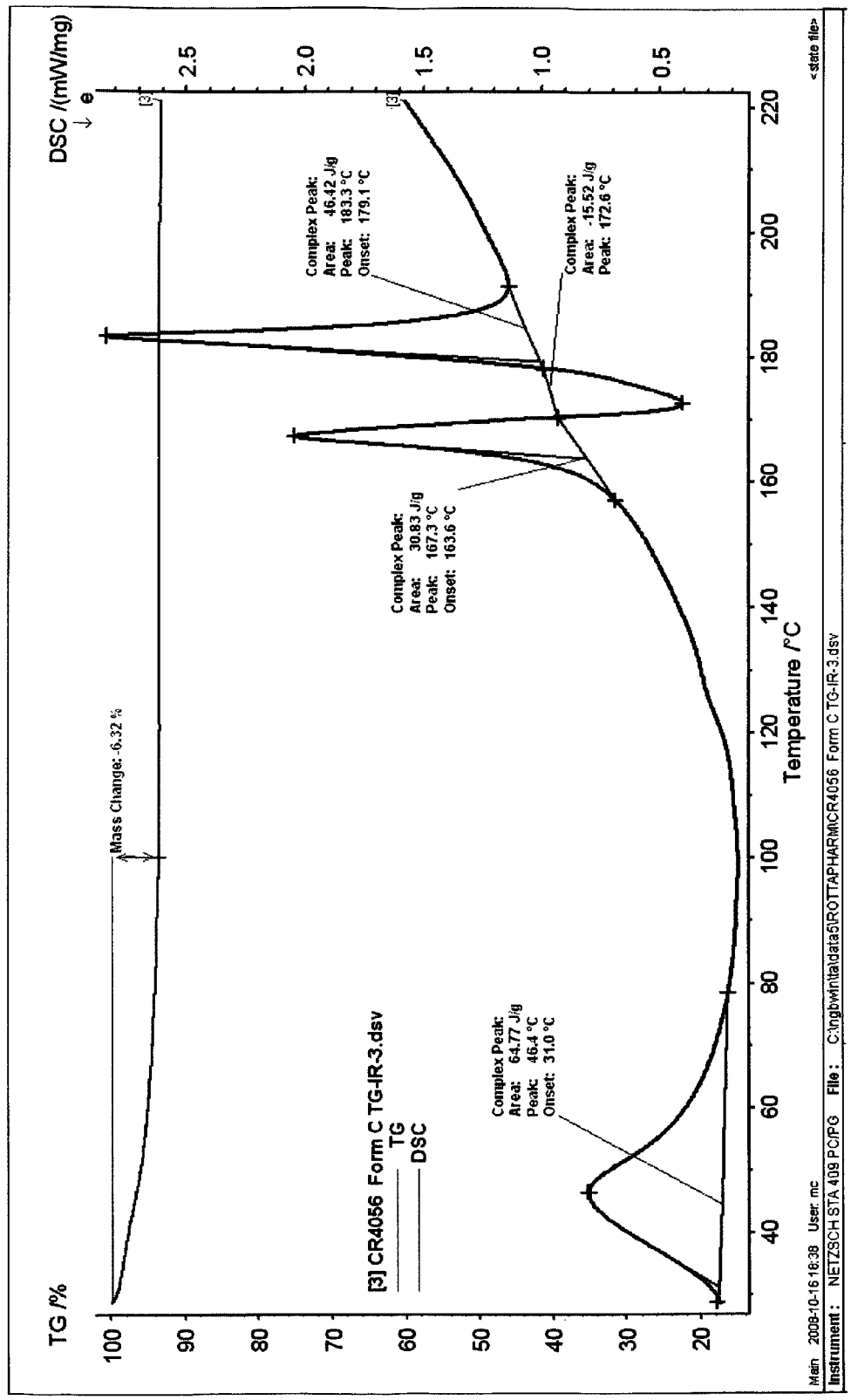
Figure 14: 6-(1H-imidazol-1-yl)-2-phenylquinazoline hydrate, form C, DSC

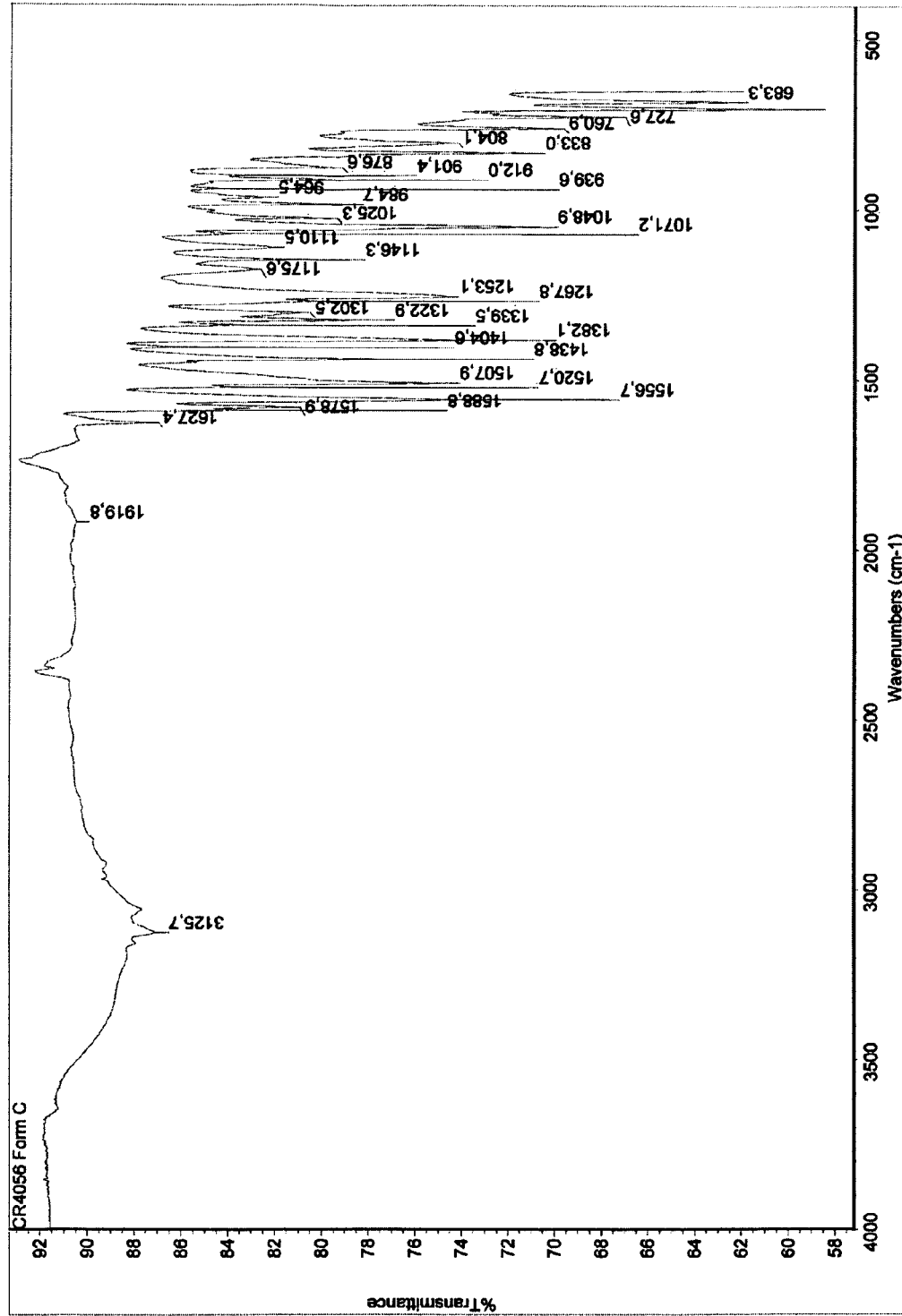

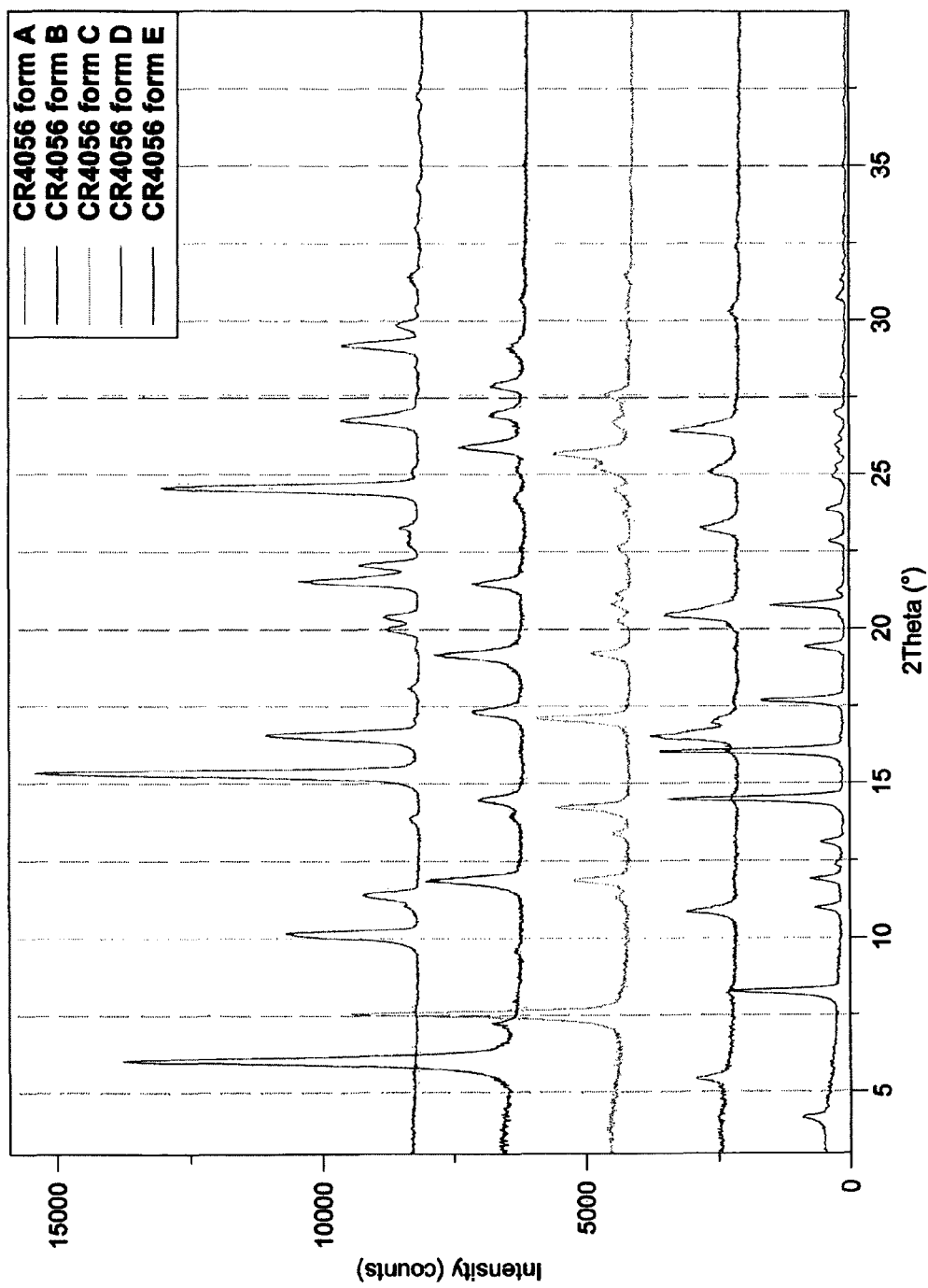
Figure 16: XRPD comparison between the various forms (polymorphs and hydrates) of 6-(1H-imidazol-1-yl)-2-phenylquinazoline as non salified base

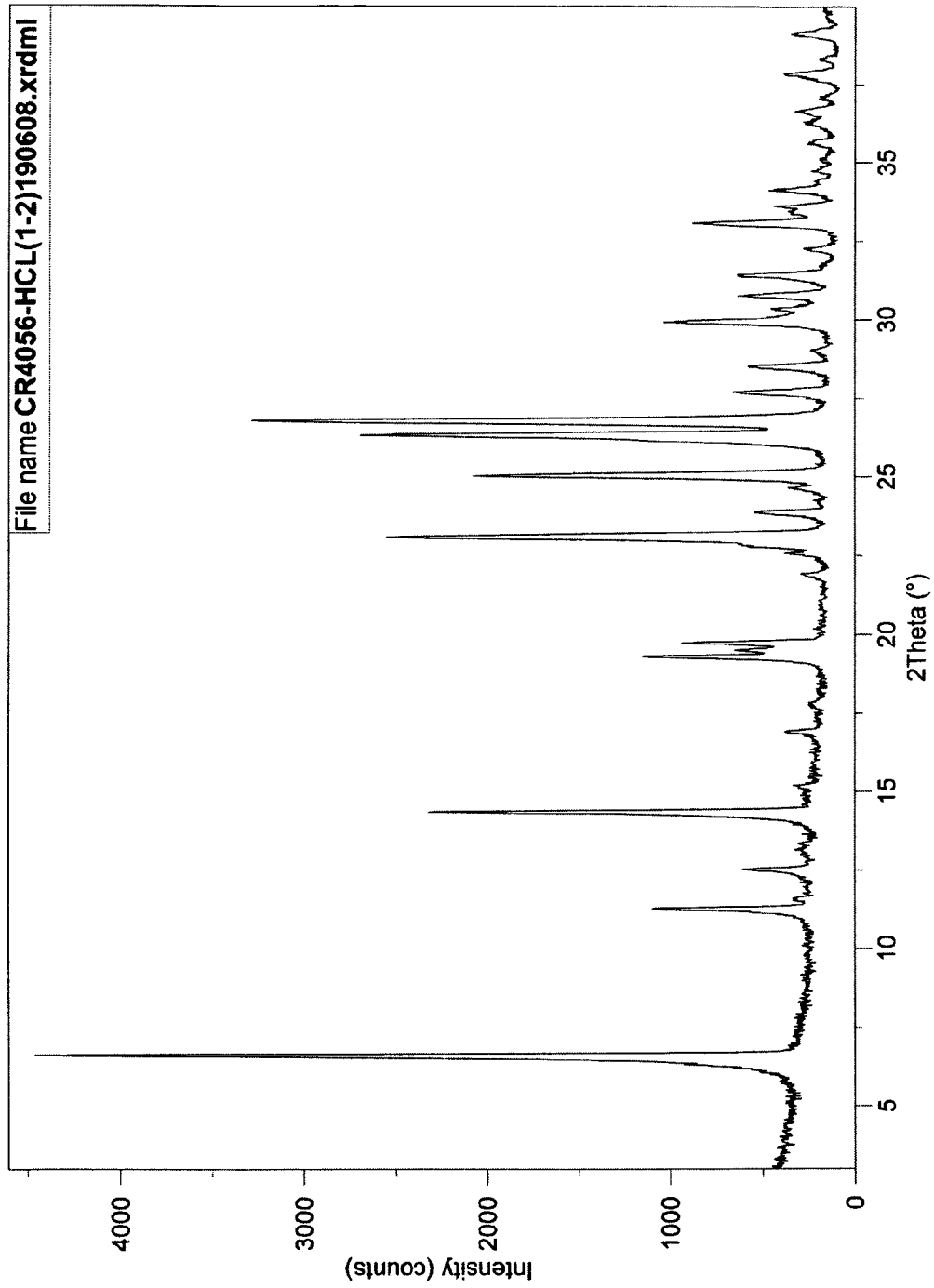

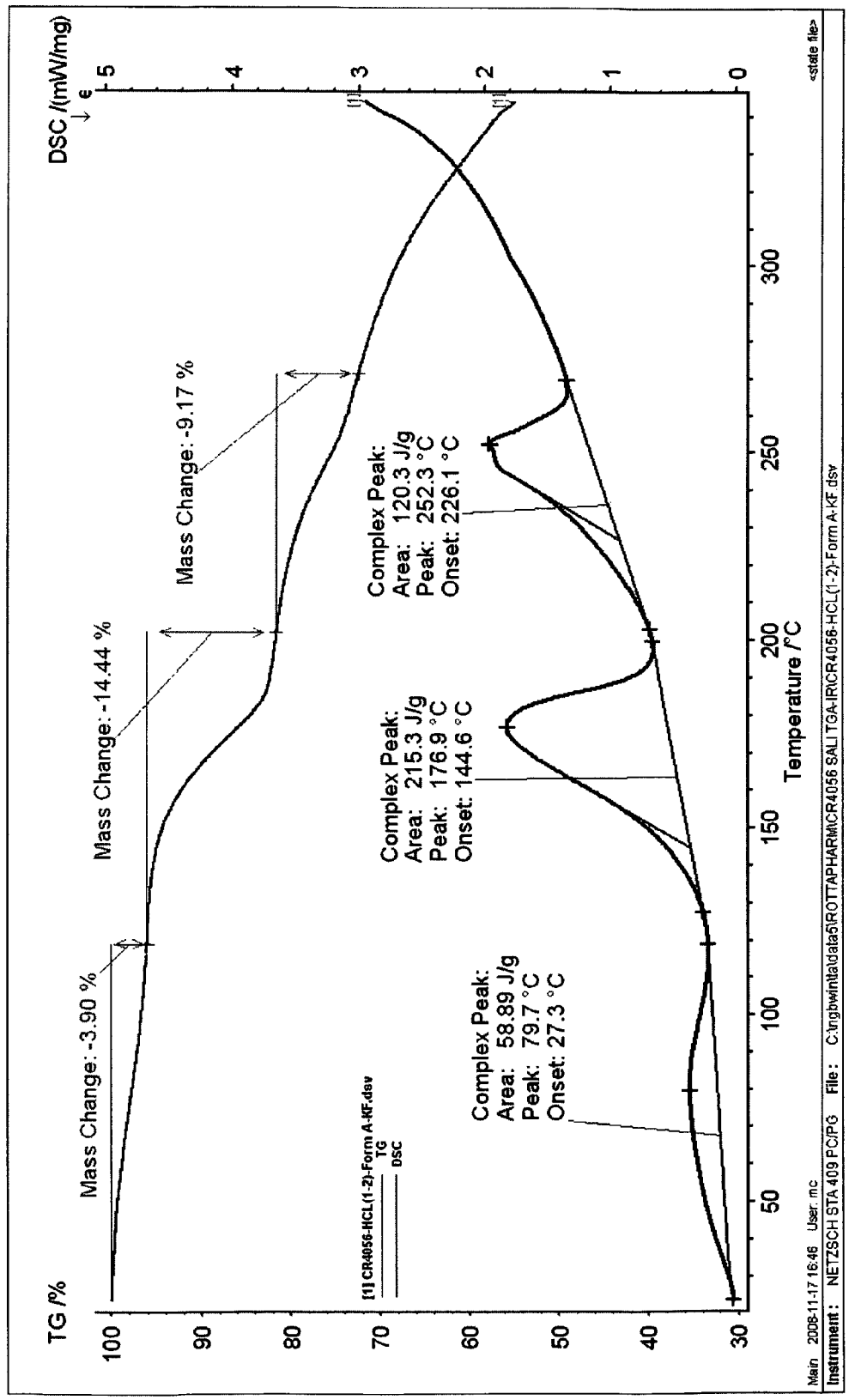
Figure 18: 6-(1H-imidazol-1-yl)-2-phenylquinazoline dihydrochloride monohydrate, form A, DSC

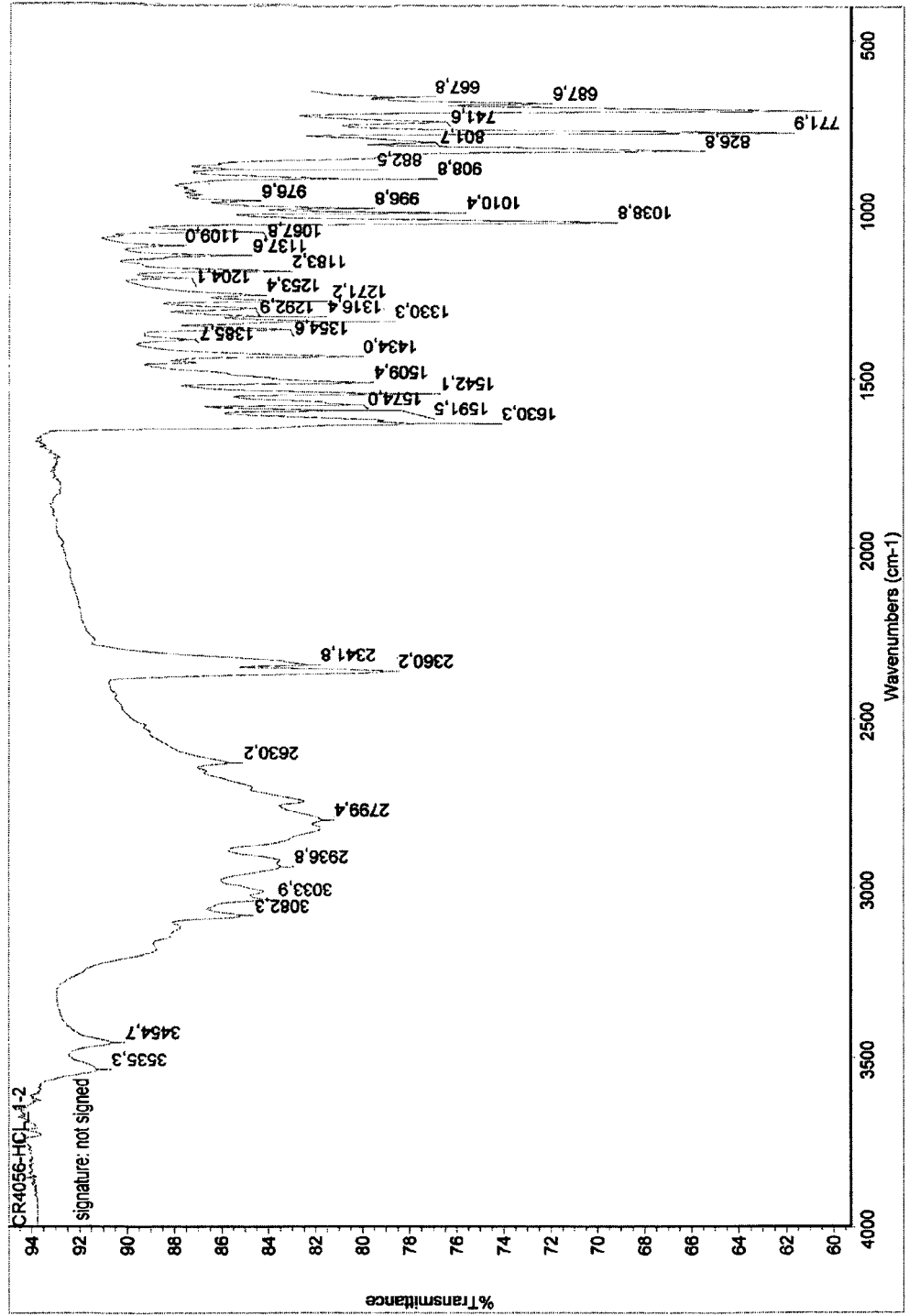

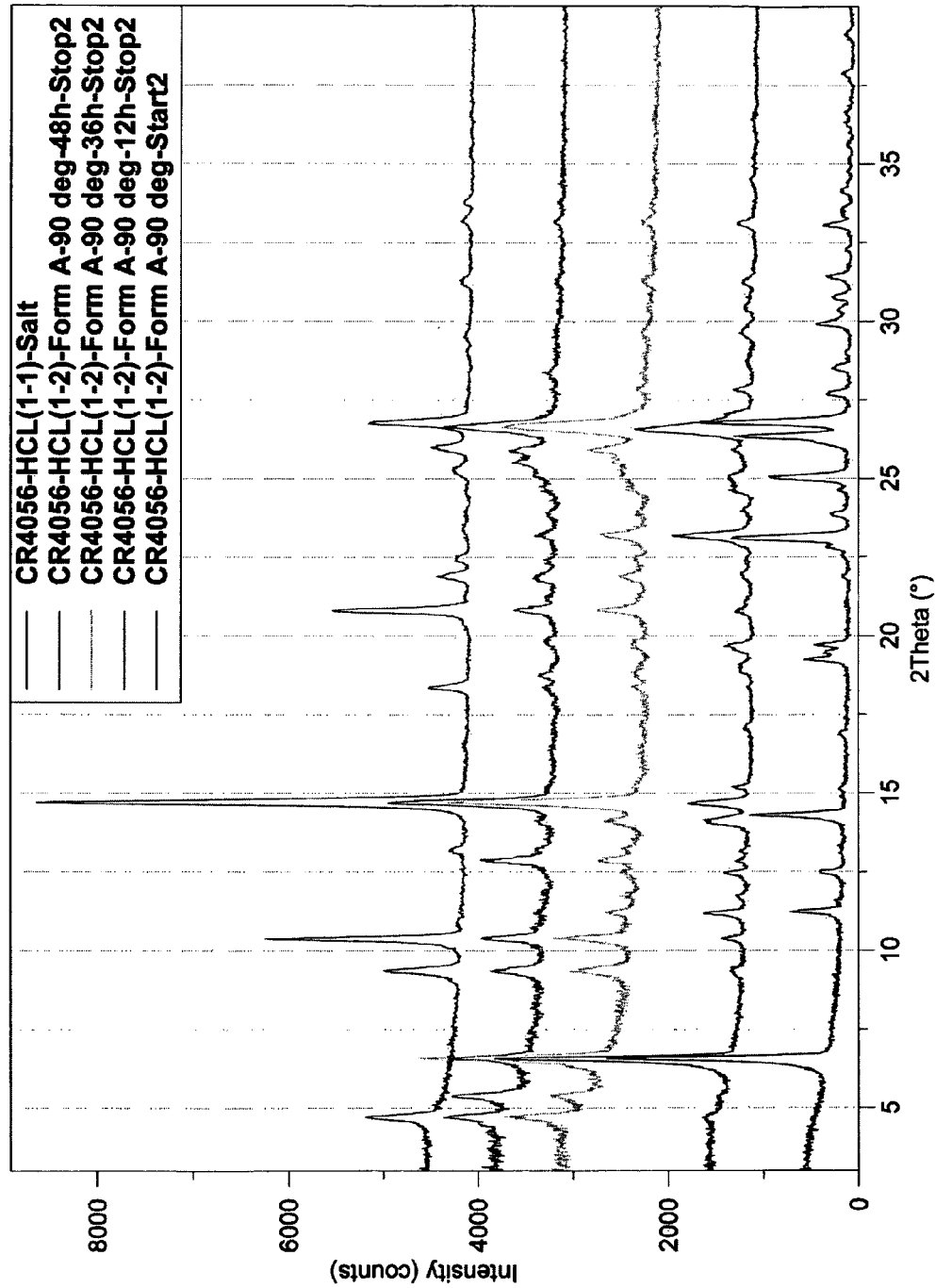
Figure19b: 6-(1H-imidazol-1-yl)-2-phenylquinazoline dihydrochloride monohydrate, form A, Thermal stability XRPD-VT

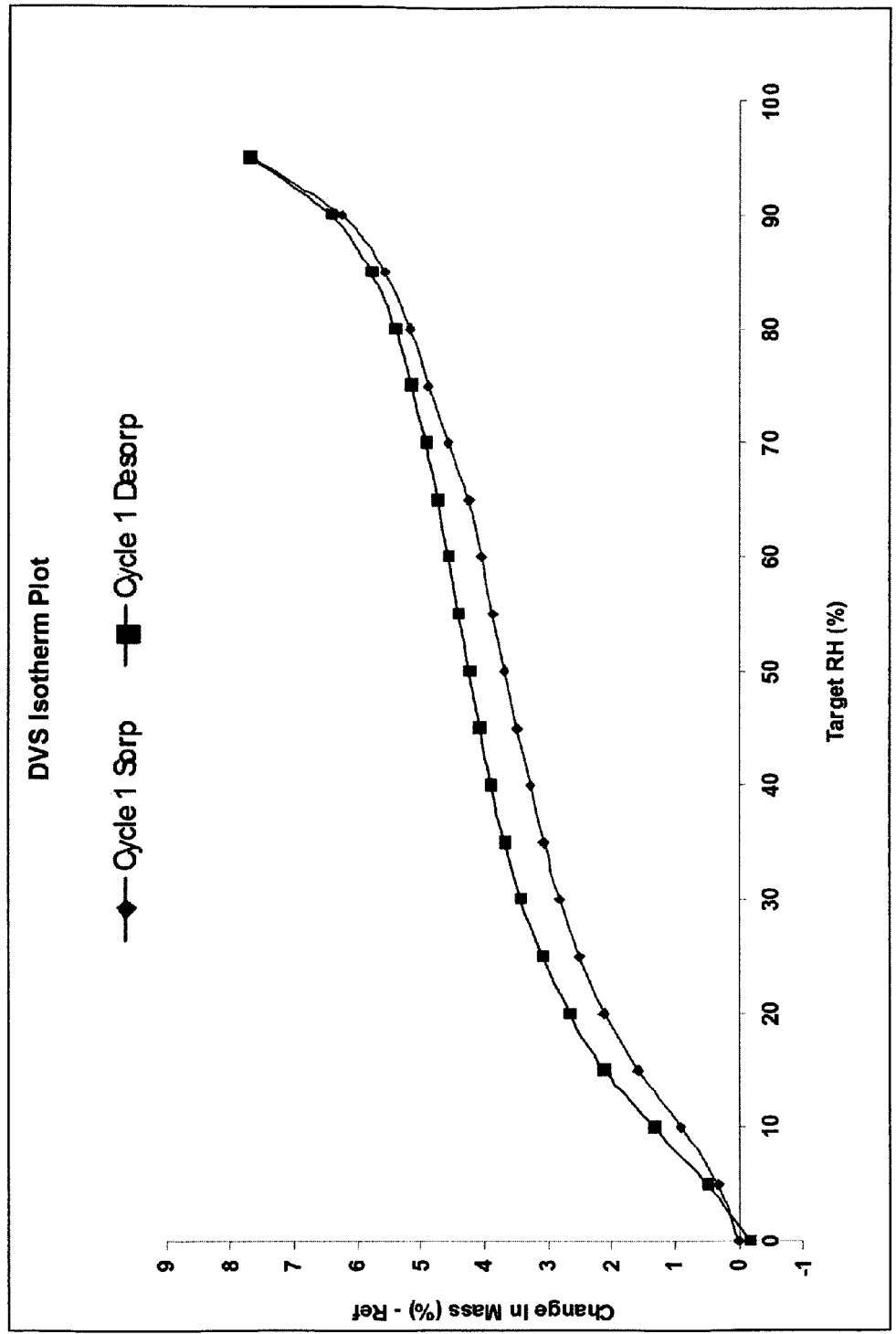
Figure 19c: 6-(1H-imidazol-1-yl)-2-phenylquinazoline dihydrocloride monohydrate forma A, DVS

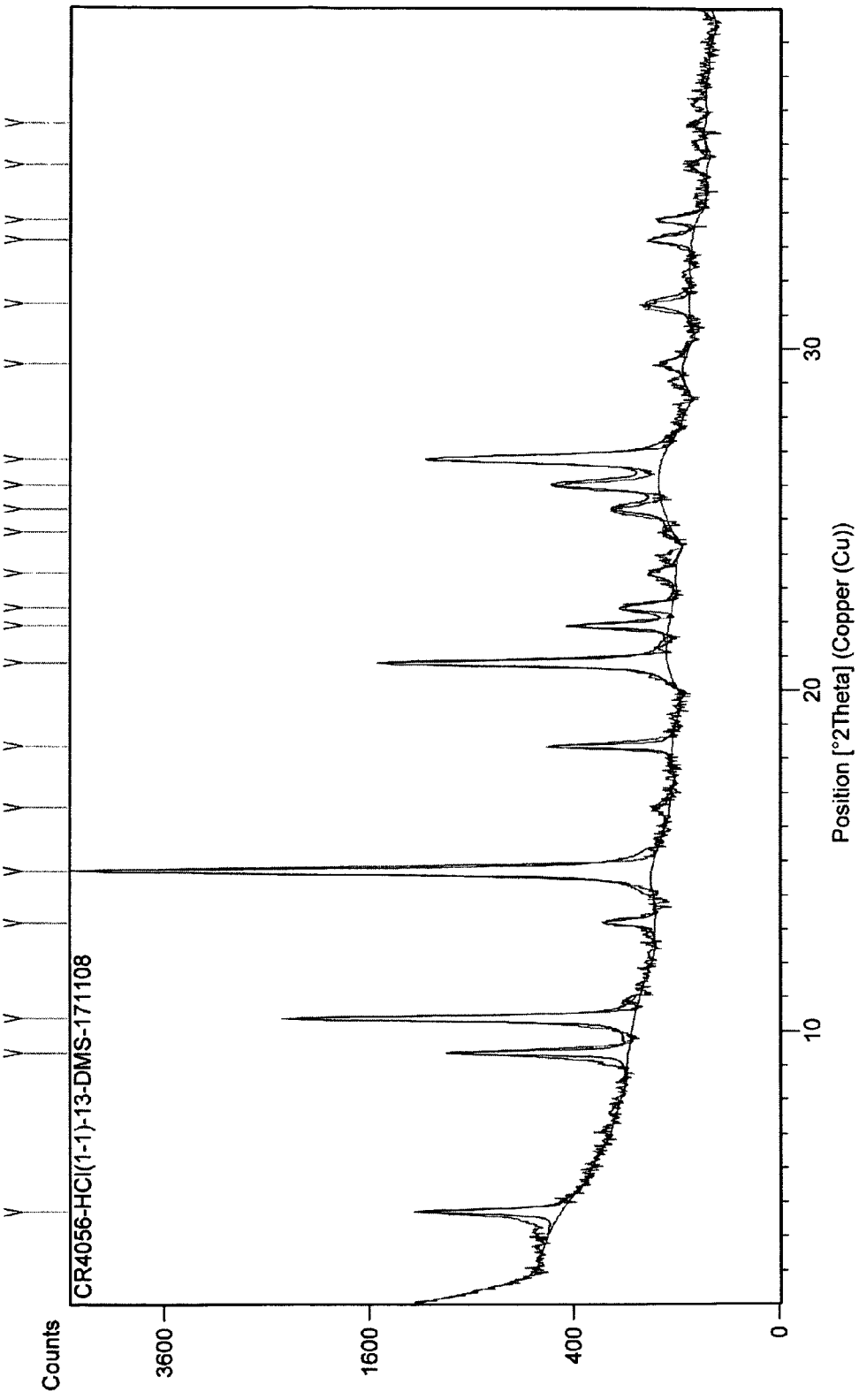

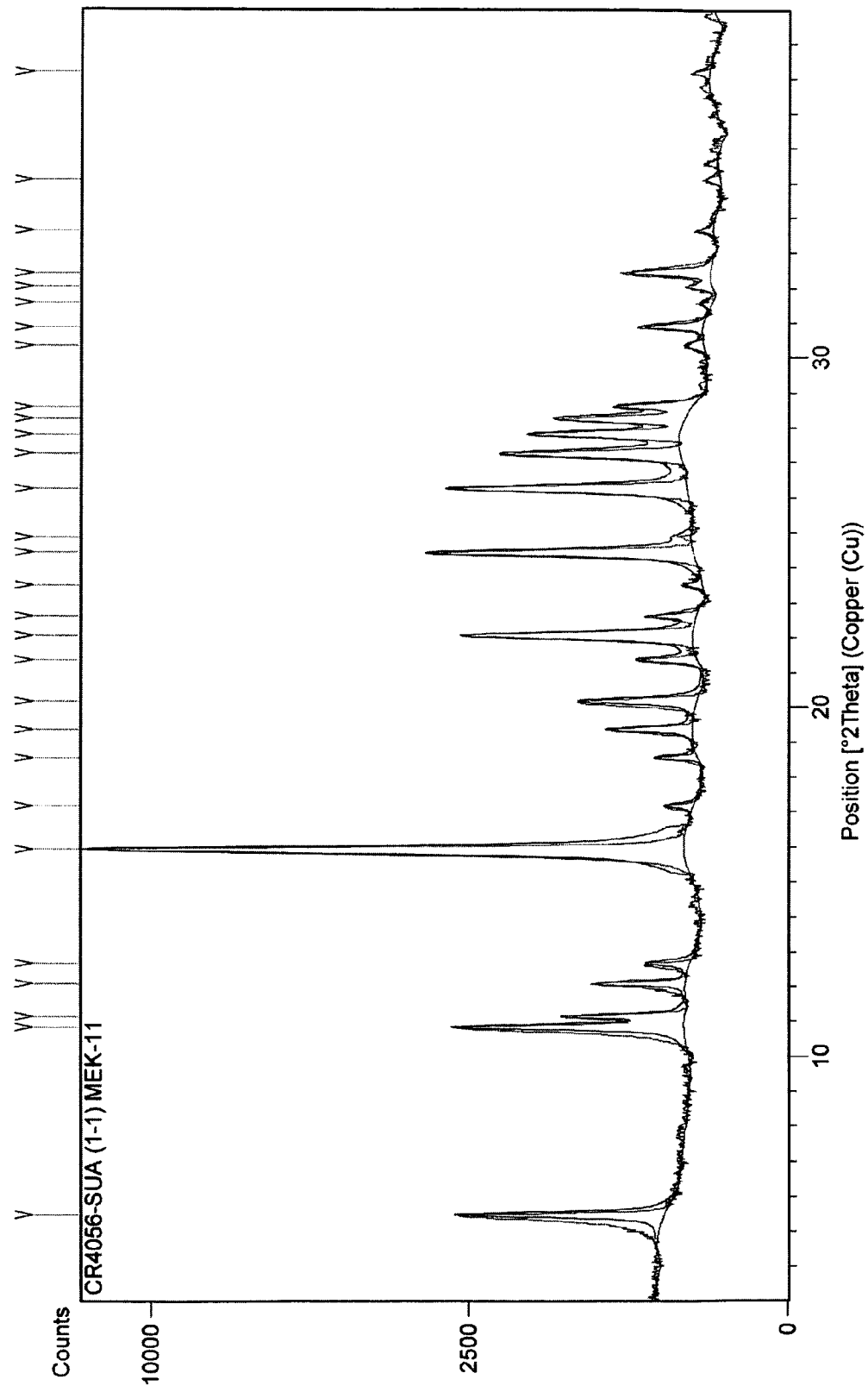
Figure 21: XRPD 6-(1H-imidazol-1-yl)-2-phenylquinazoline (I) succinate Form A

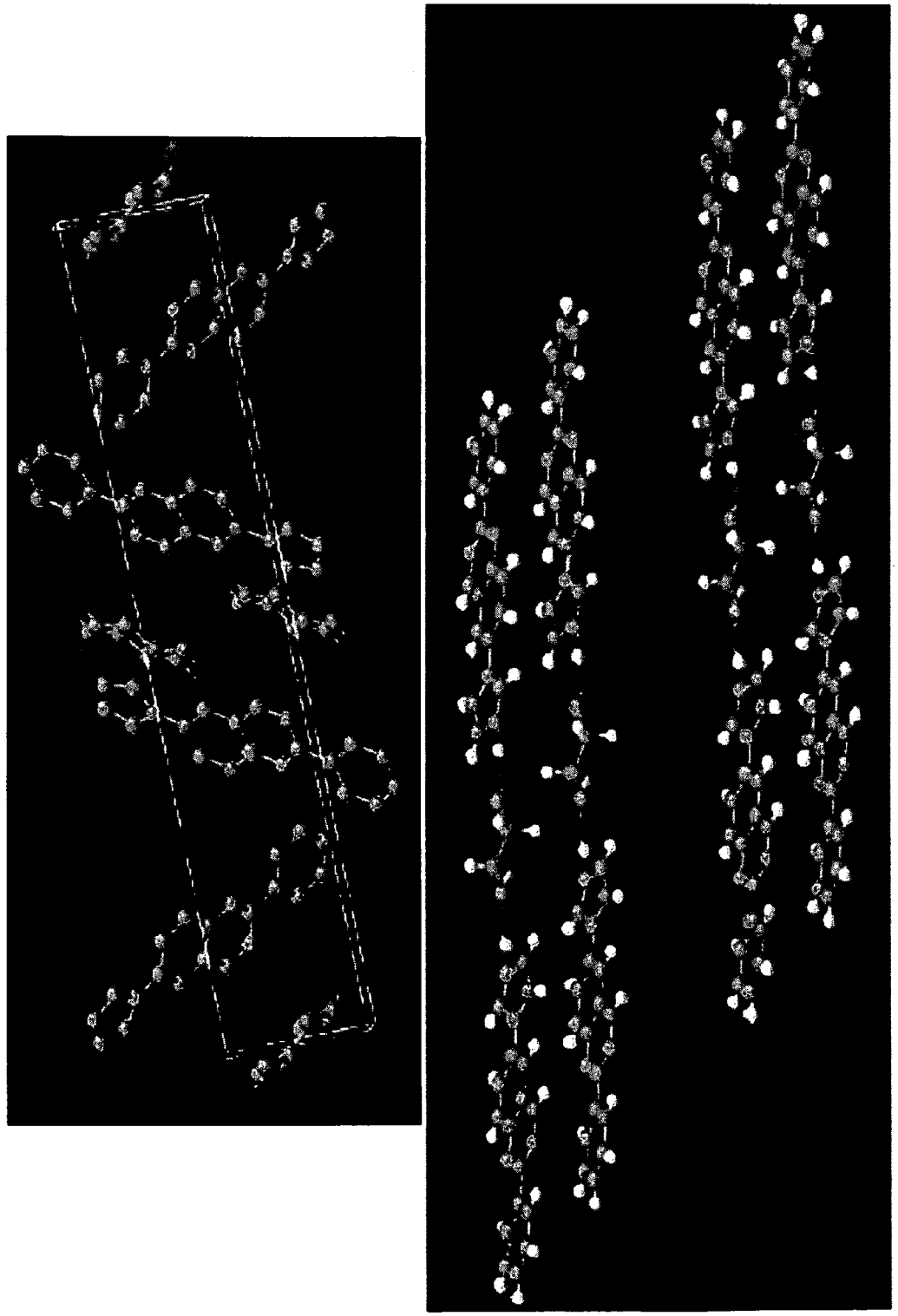
Figure 21a: Crystal structure of 6-(1H-imidazol-1-yl)-2-phenylquinazoline succinate, Form A, as obtained by SC-RX

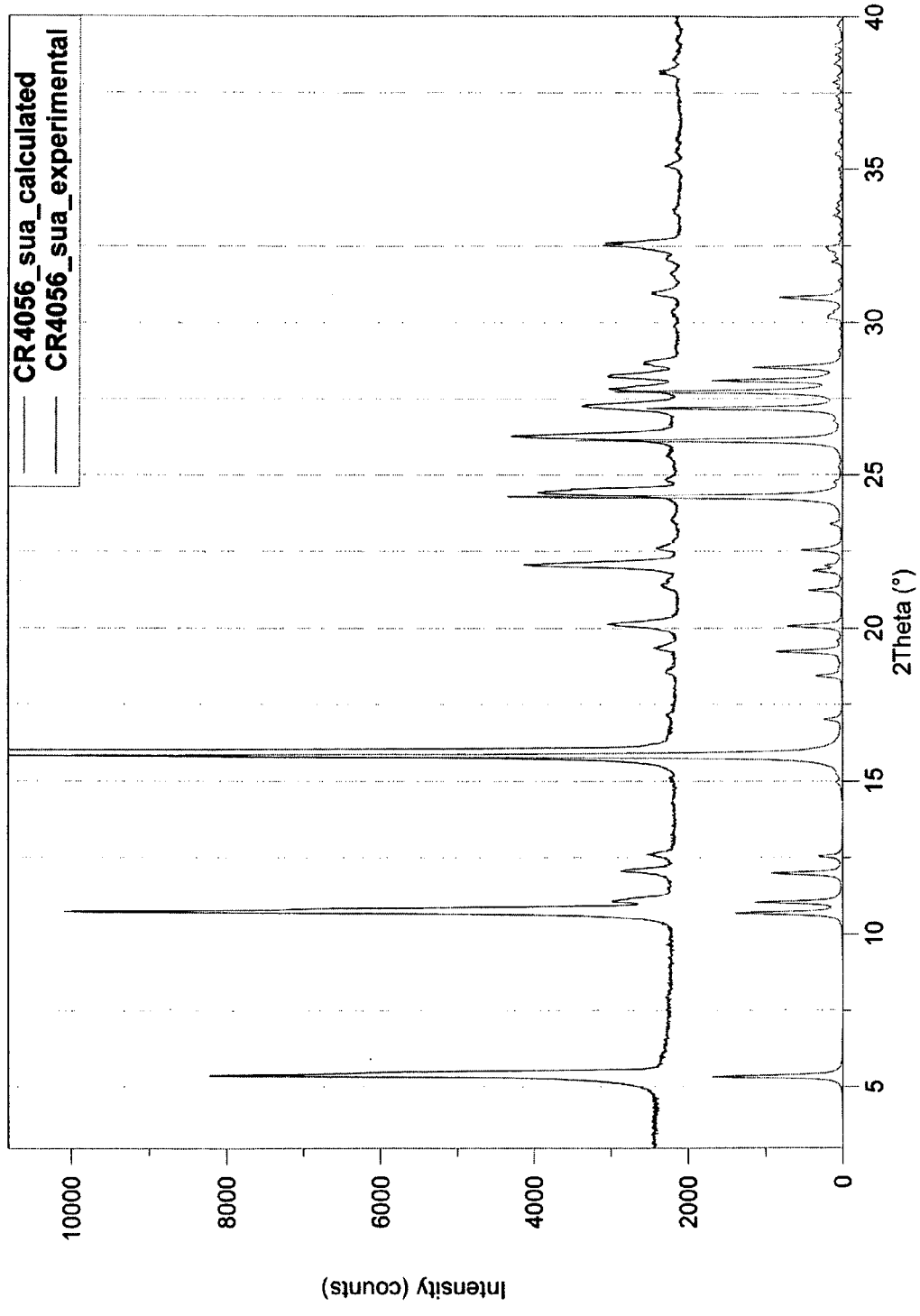
Figure 21b: comparison between XRPD calculated on the basis of the structure obtained by SC-RX and the experimental result

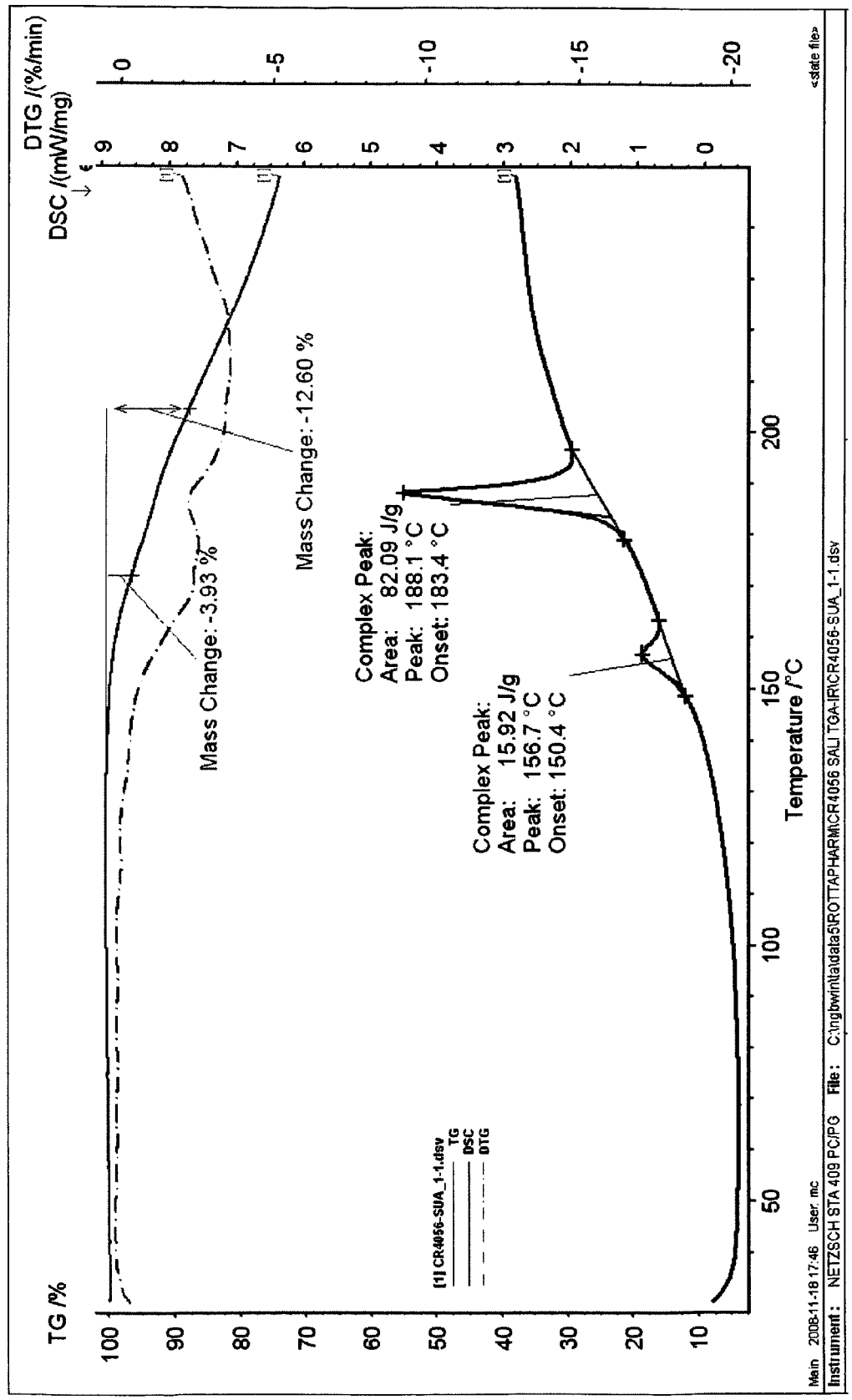
Figure 22: 6-(1H-imidazol-1-yl)-2-phenylquinazoline succinate, Form A, DSC

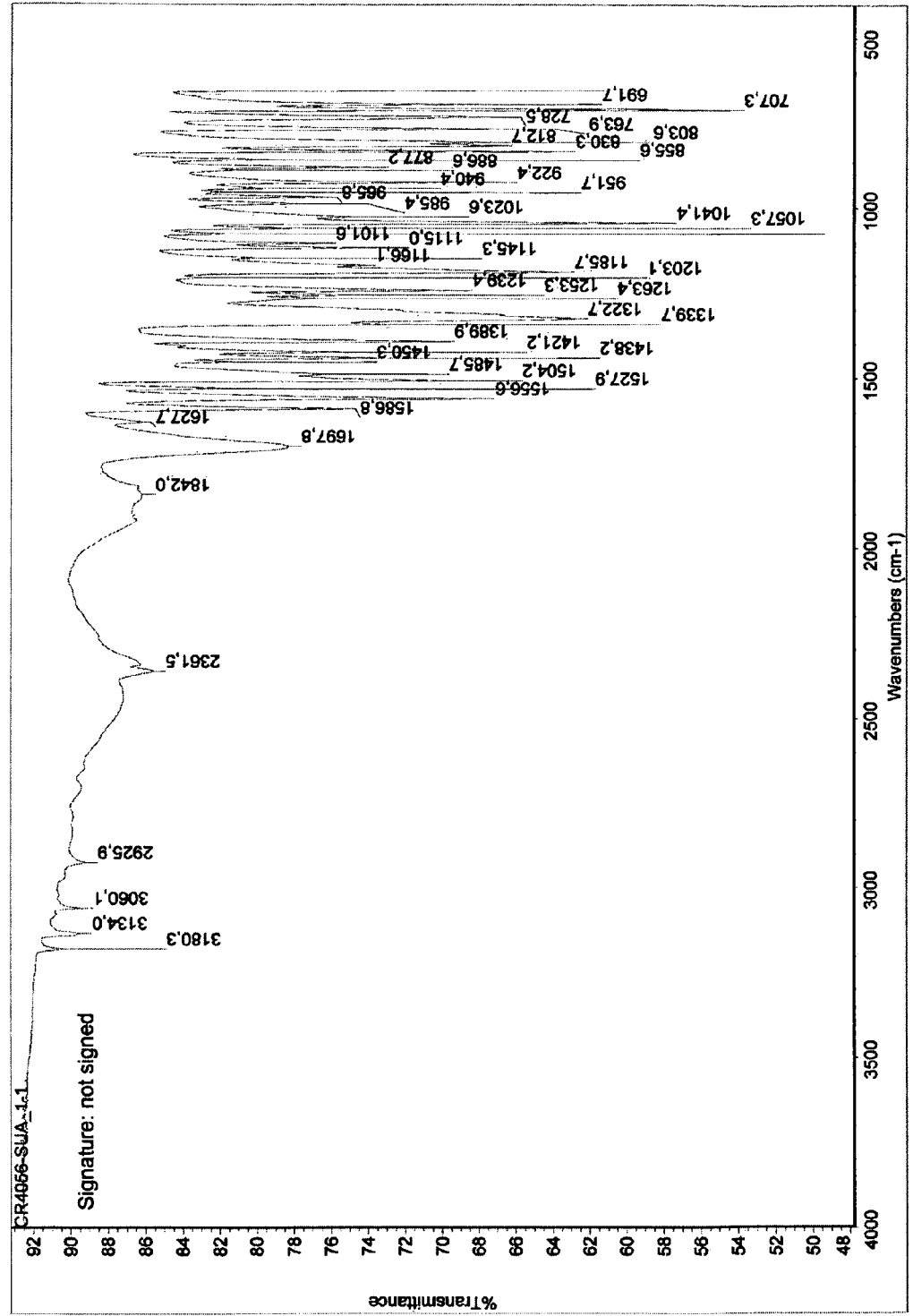
Figure 23: 6-(1H-imidazol-1-yl)-2-phenylquinazoline succinate, Form A, FT-IR

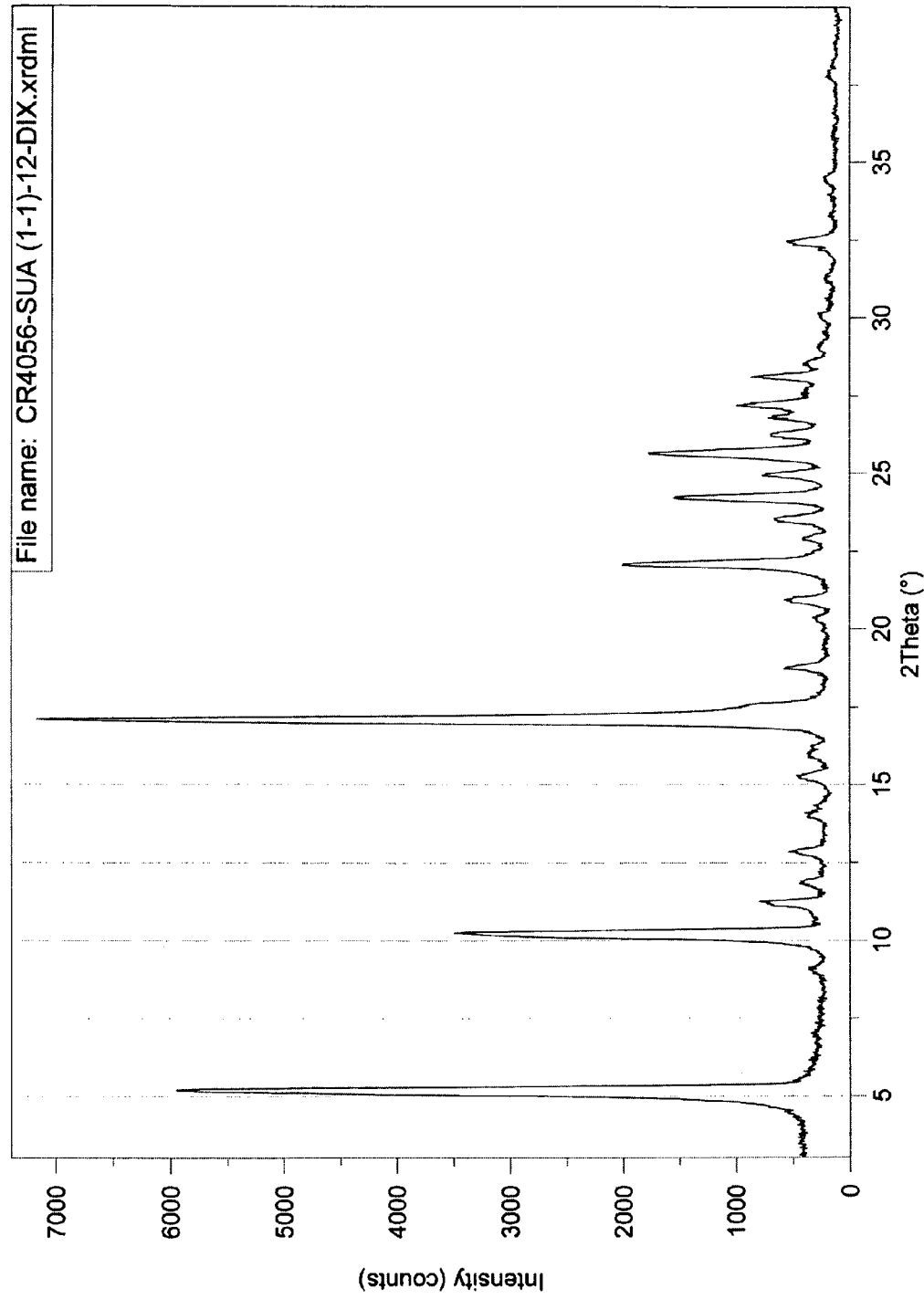

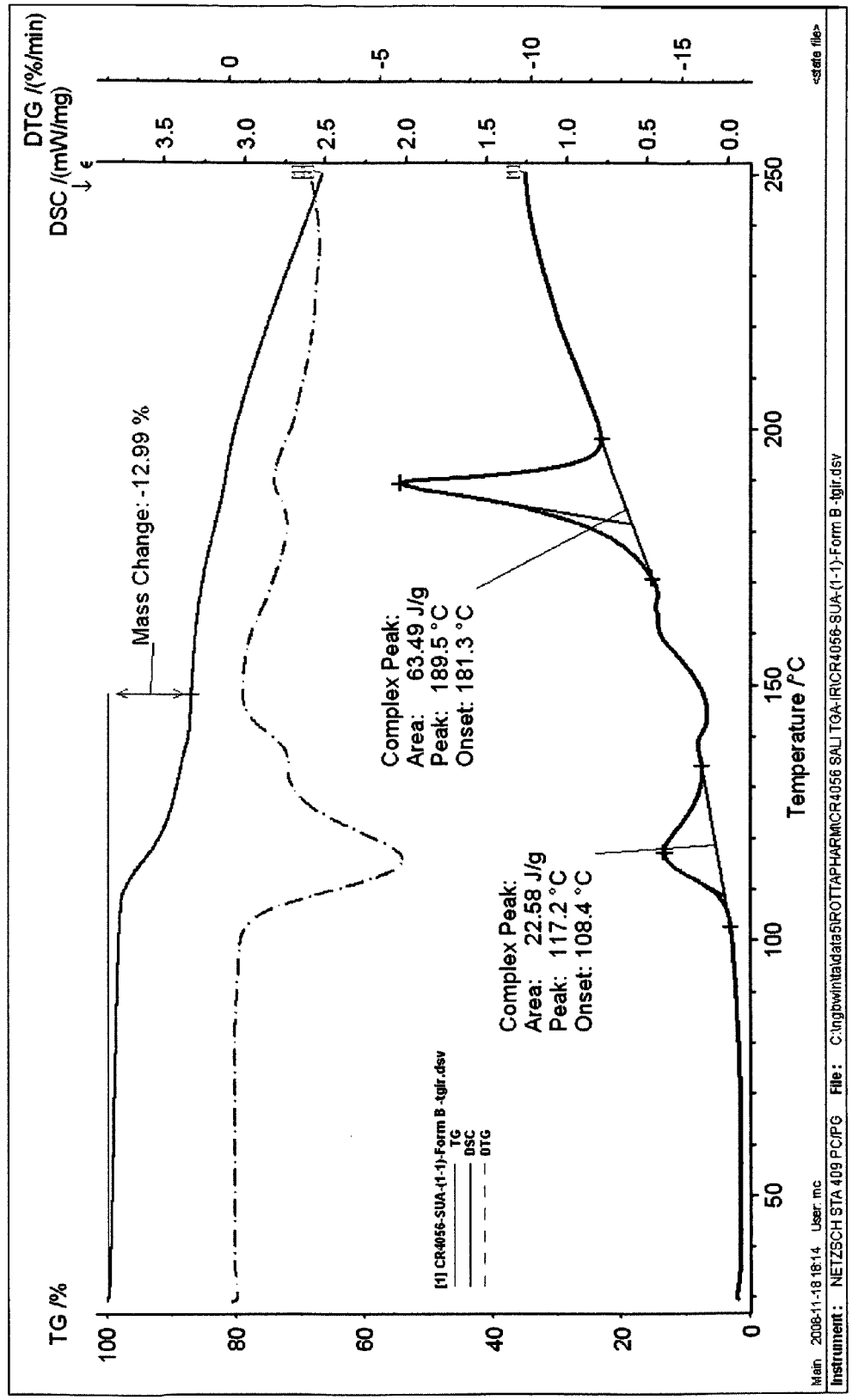
Figure 25: 6-(1H-imidazol-1-yl)-2-phenylquinazoline succinate, Form B, DSC

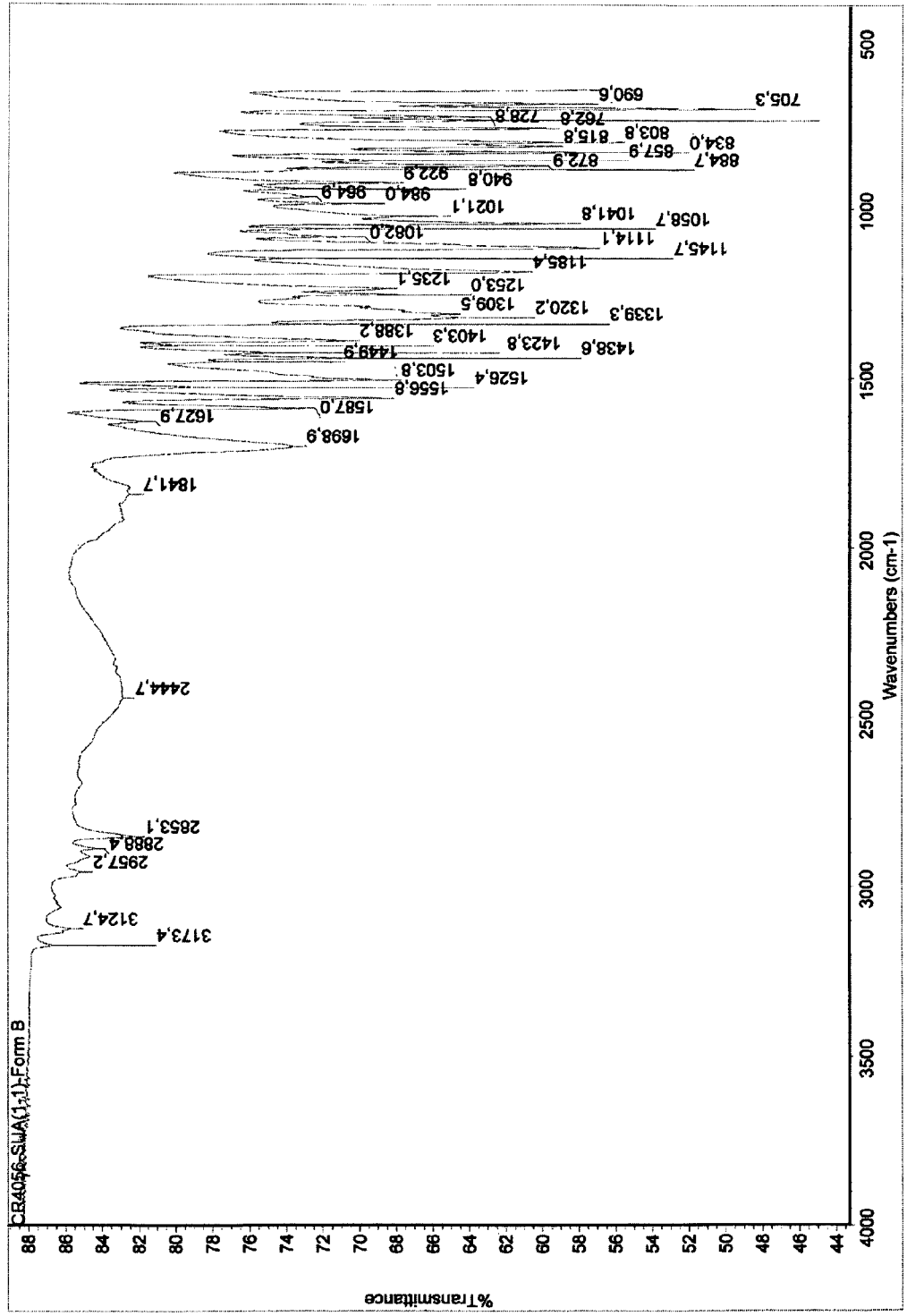
Figure 26: 6-(1H-imidazol-1-yl)-2-phenylquinazoline succinate, Form B, FT-IR

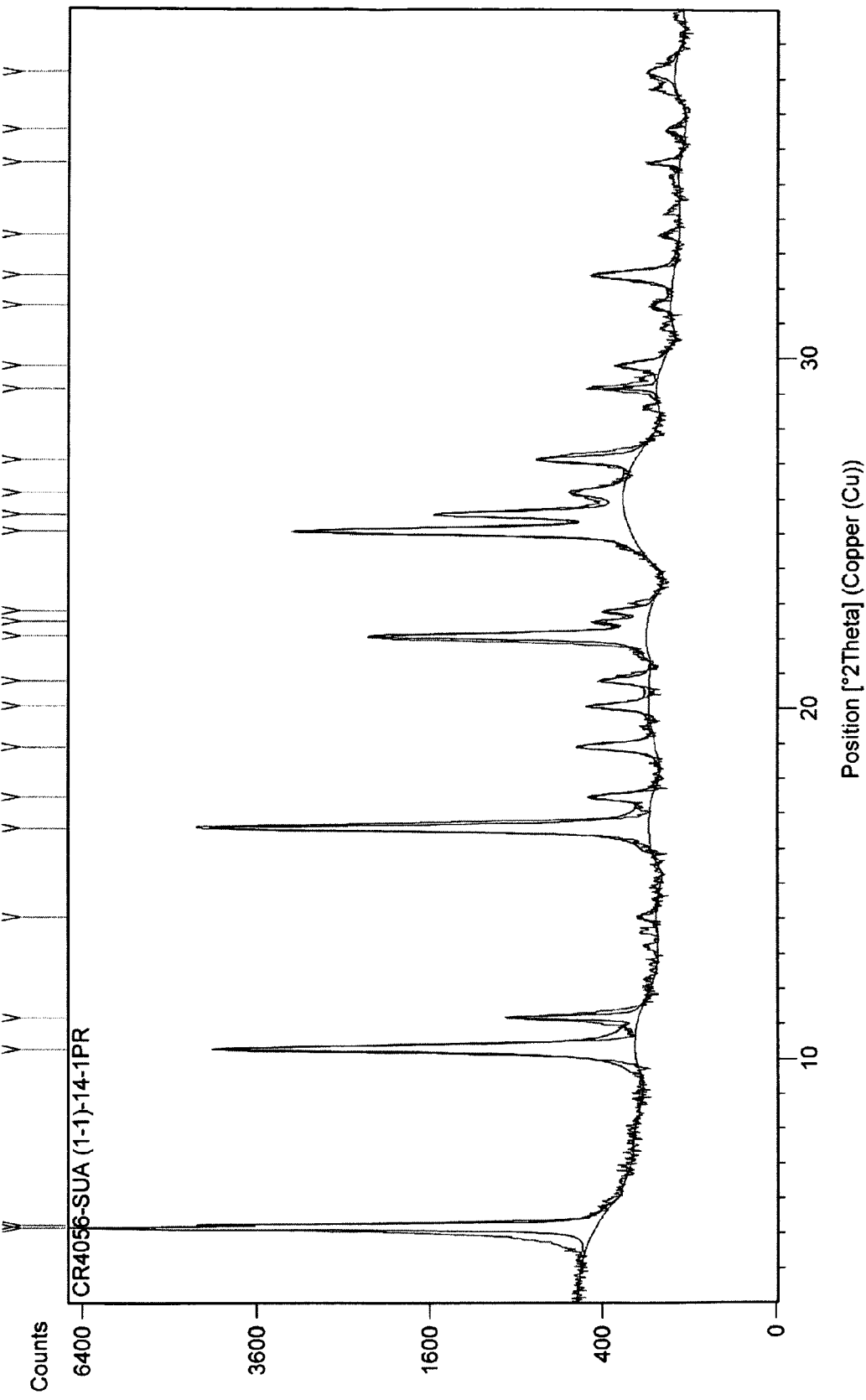
Figure 27: Crystalline form of 6-(1H-imidazol-1-yl)-2-phenylquinazoline succinate, Form C, XRPD

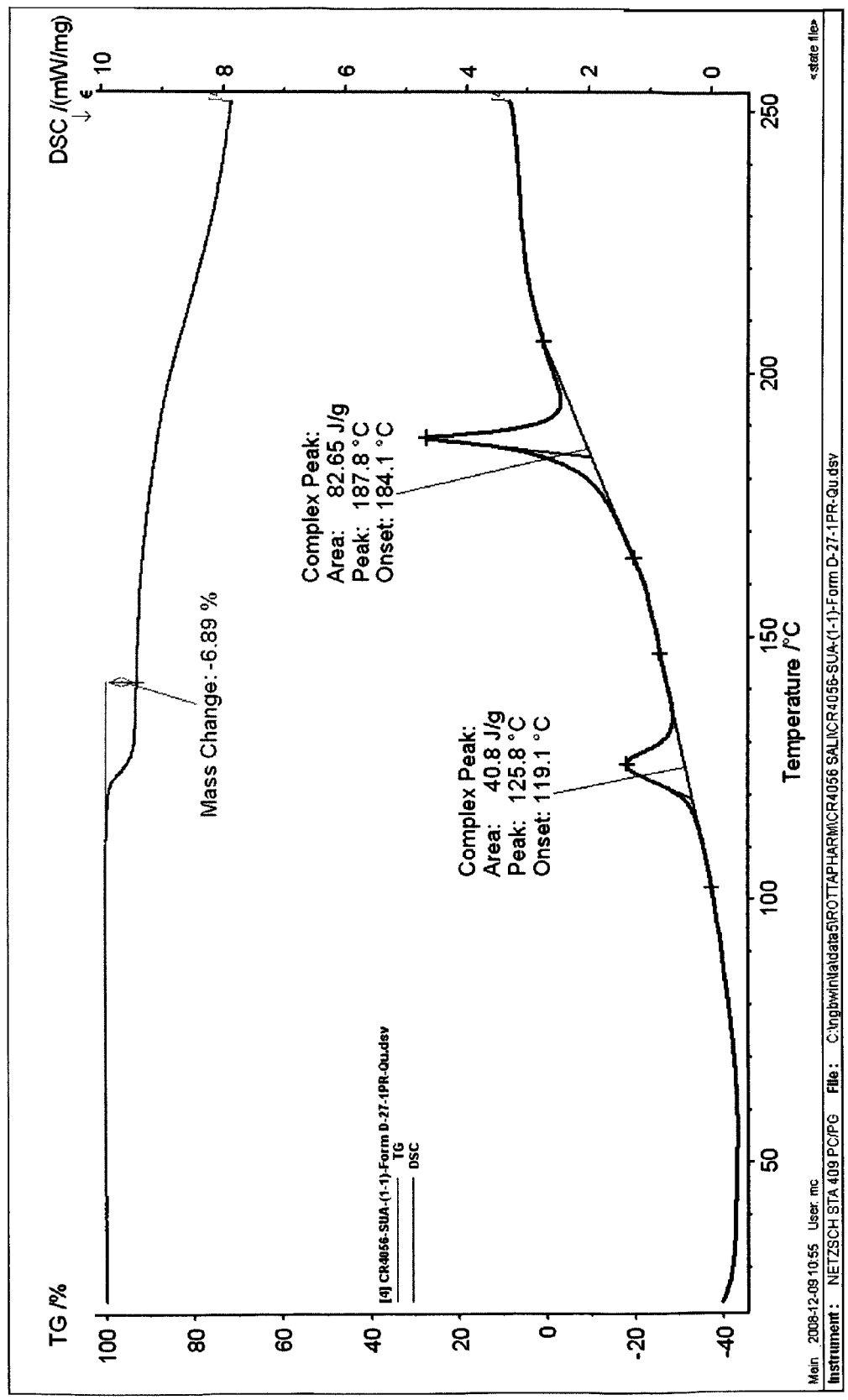
Figure 28: 6-(1H-imidazol-1-yl)-2-phenylquinazoline succinate, Form C, DSC

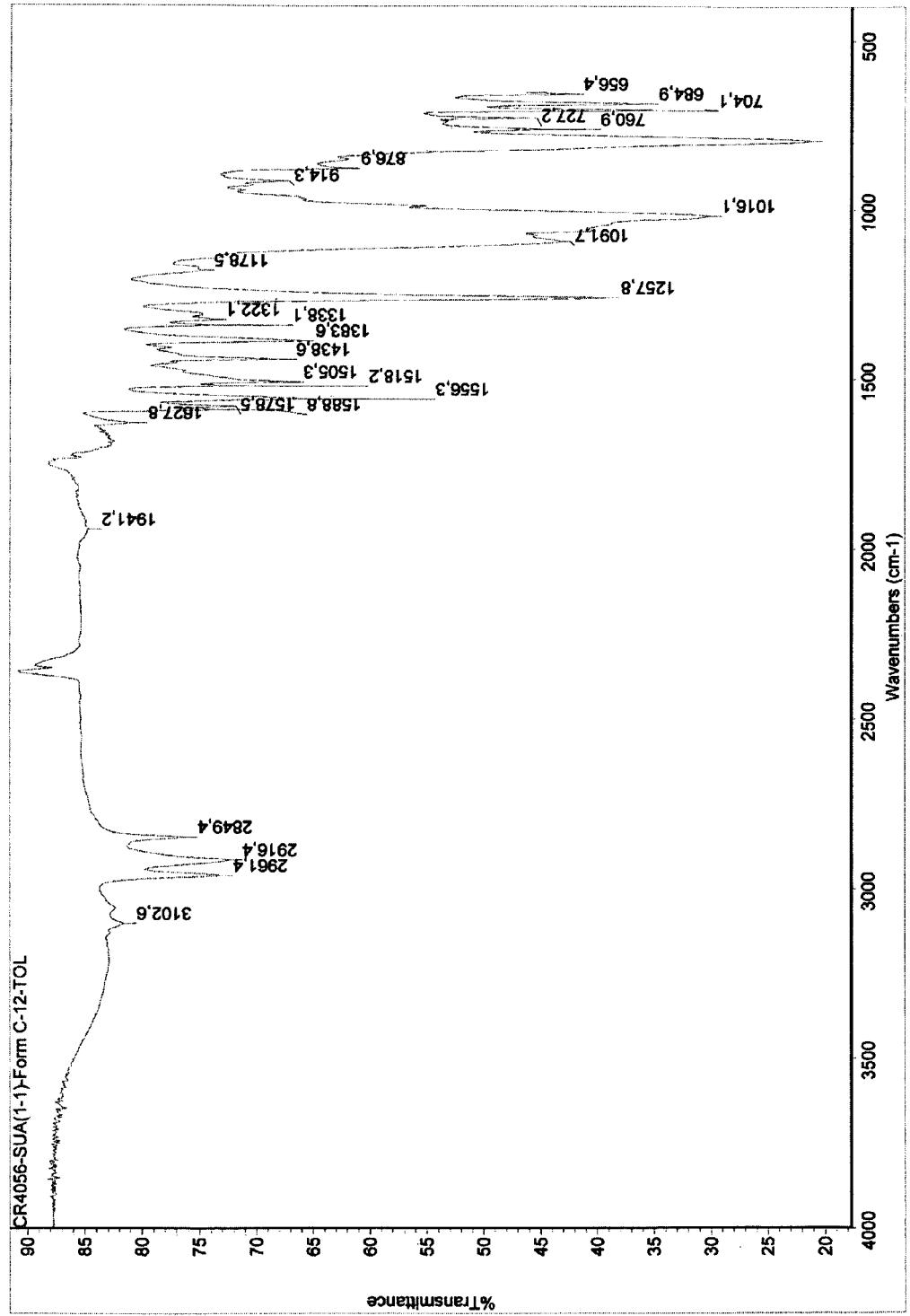
Figure 29: 6-(1H-imidazol-1-yl)-2-phenylquinazoline succinate, Form C, FT-IR

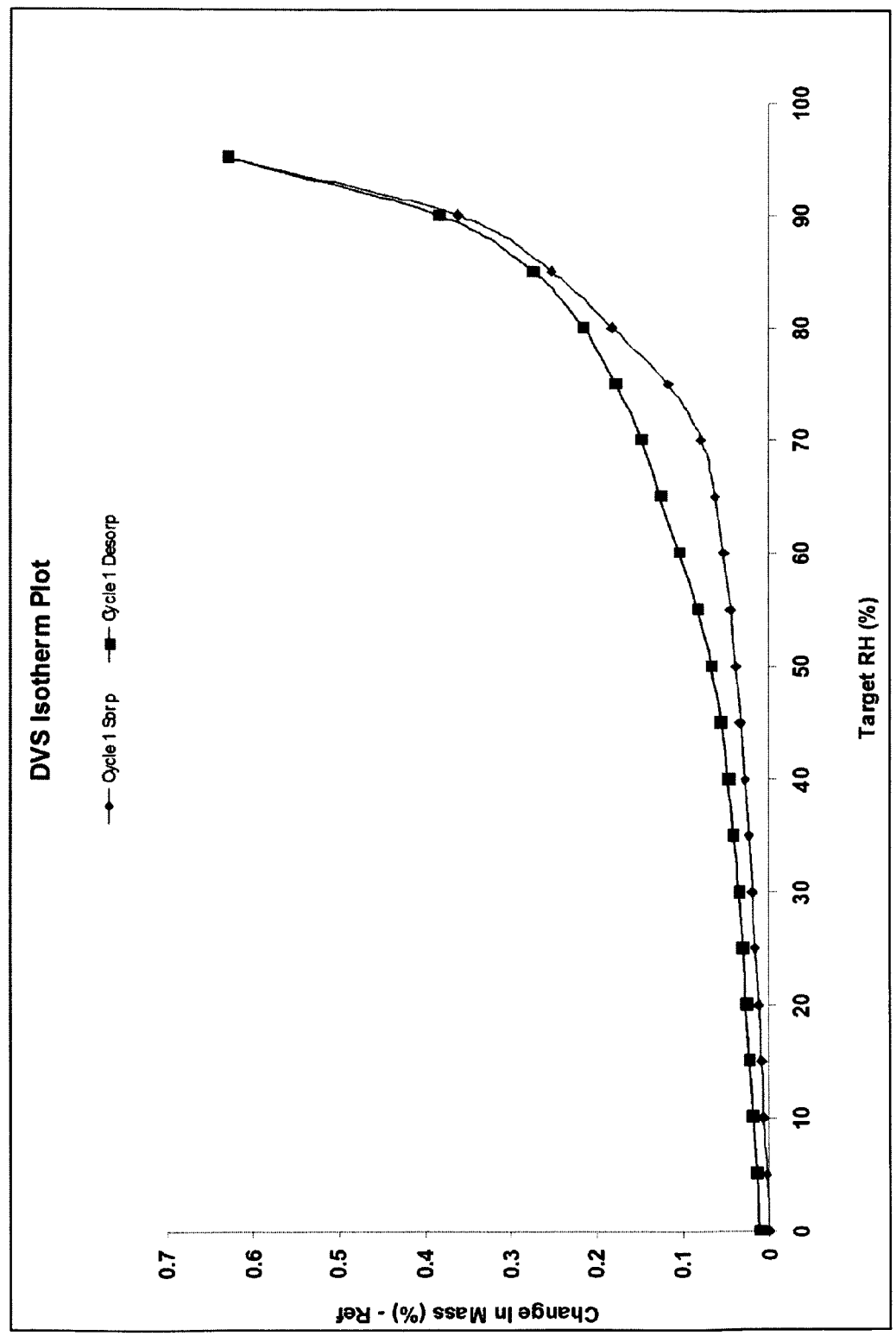
Figure 30: 6-(1H-imidazol-1-yl)-2-phenylquinazoline succinate form A, DVS

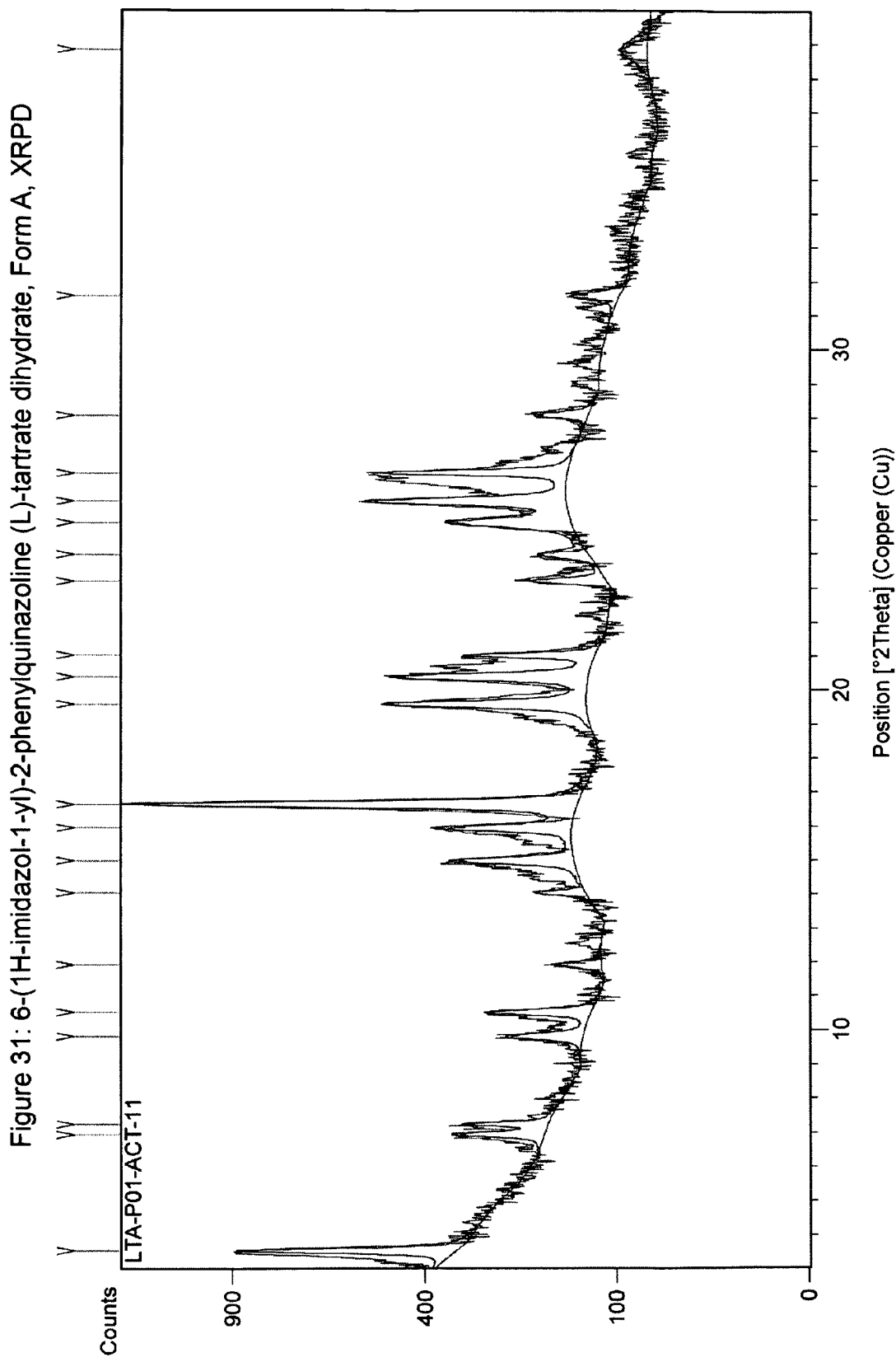
Figure 31: 6-(1H-imidazol-1-yl)-2-phenylquinazoline (L)-tartrate dihydrate, Form A, XRPD

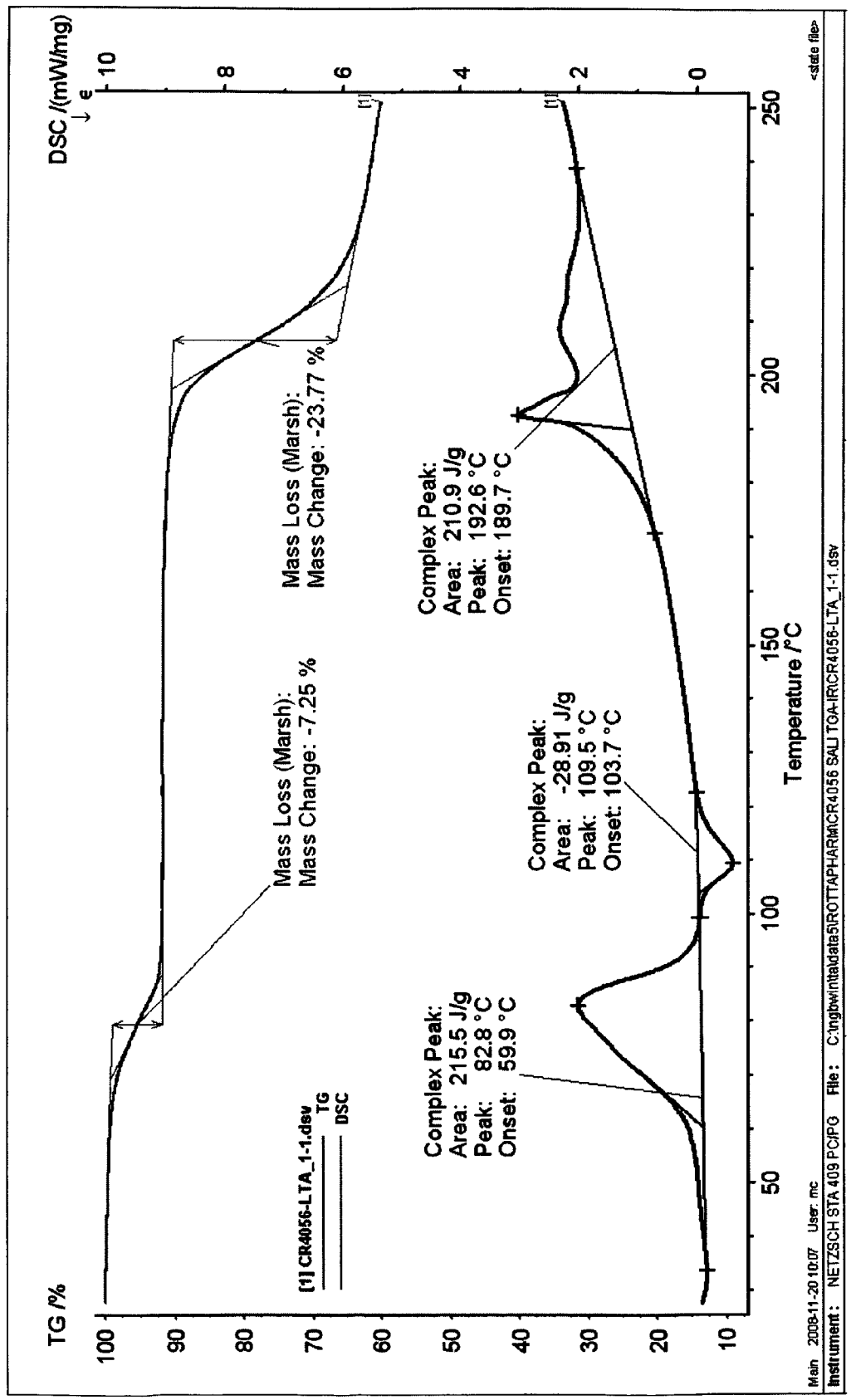
Figure 32: 6-(1H-imidazol-1-yl)-2-phenylquinazoline (L)-tartrate dihydrate, Form A, DSC

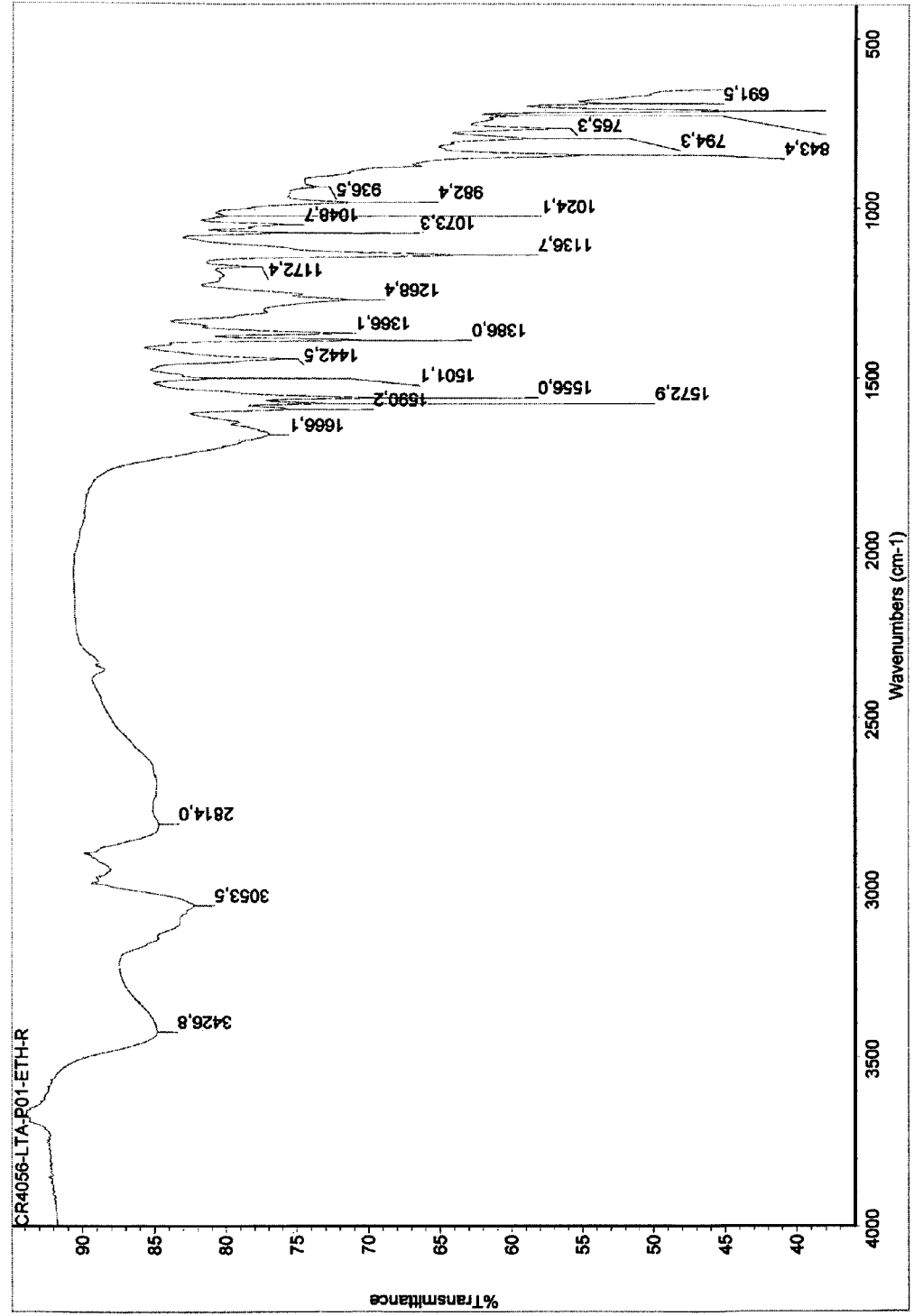

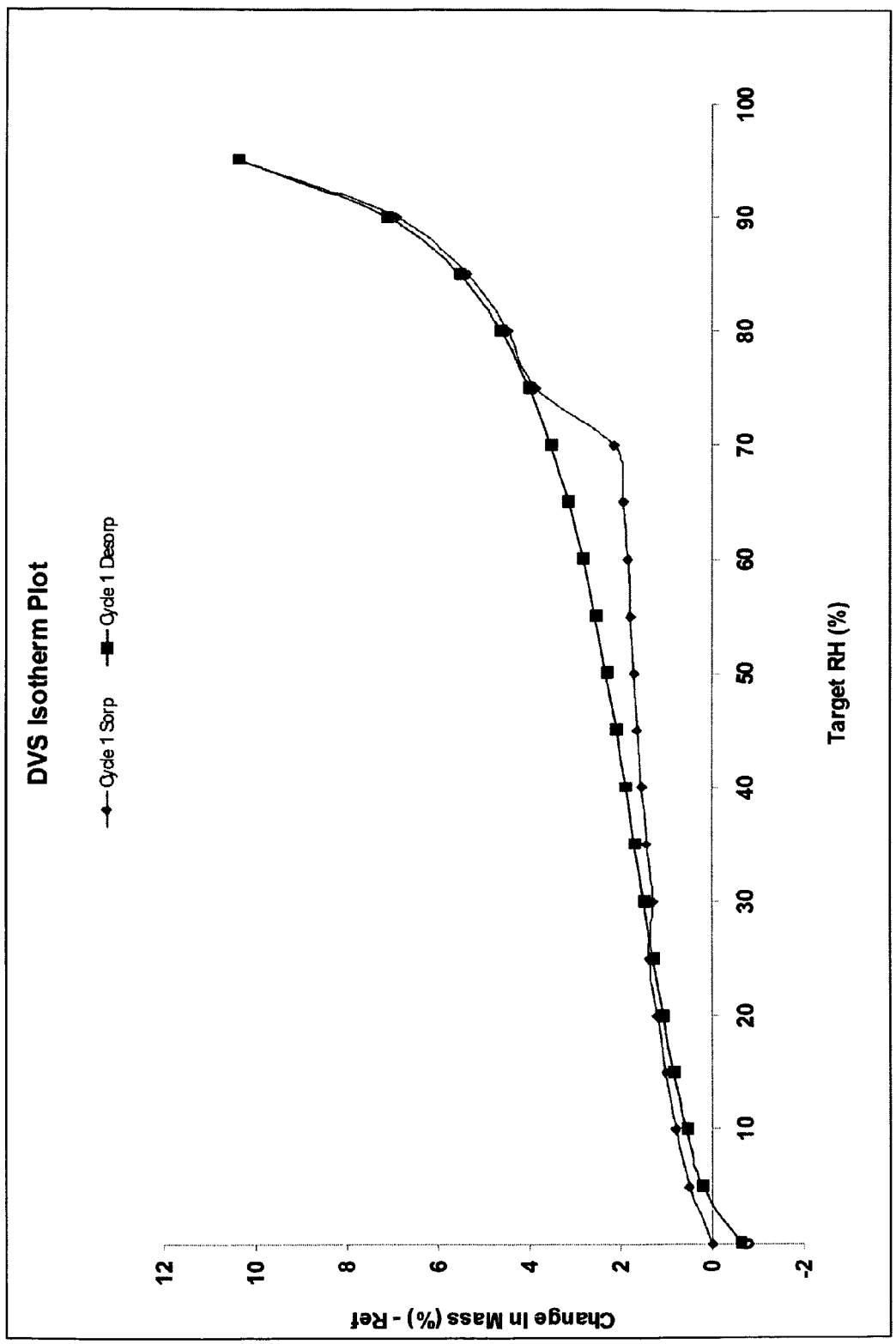
Figure 34: 6-(1H-imidazol-1-yl)-2-phenylquinazoline tartrate dihydrate, form A, DVS

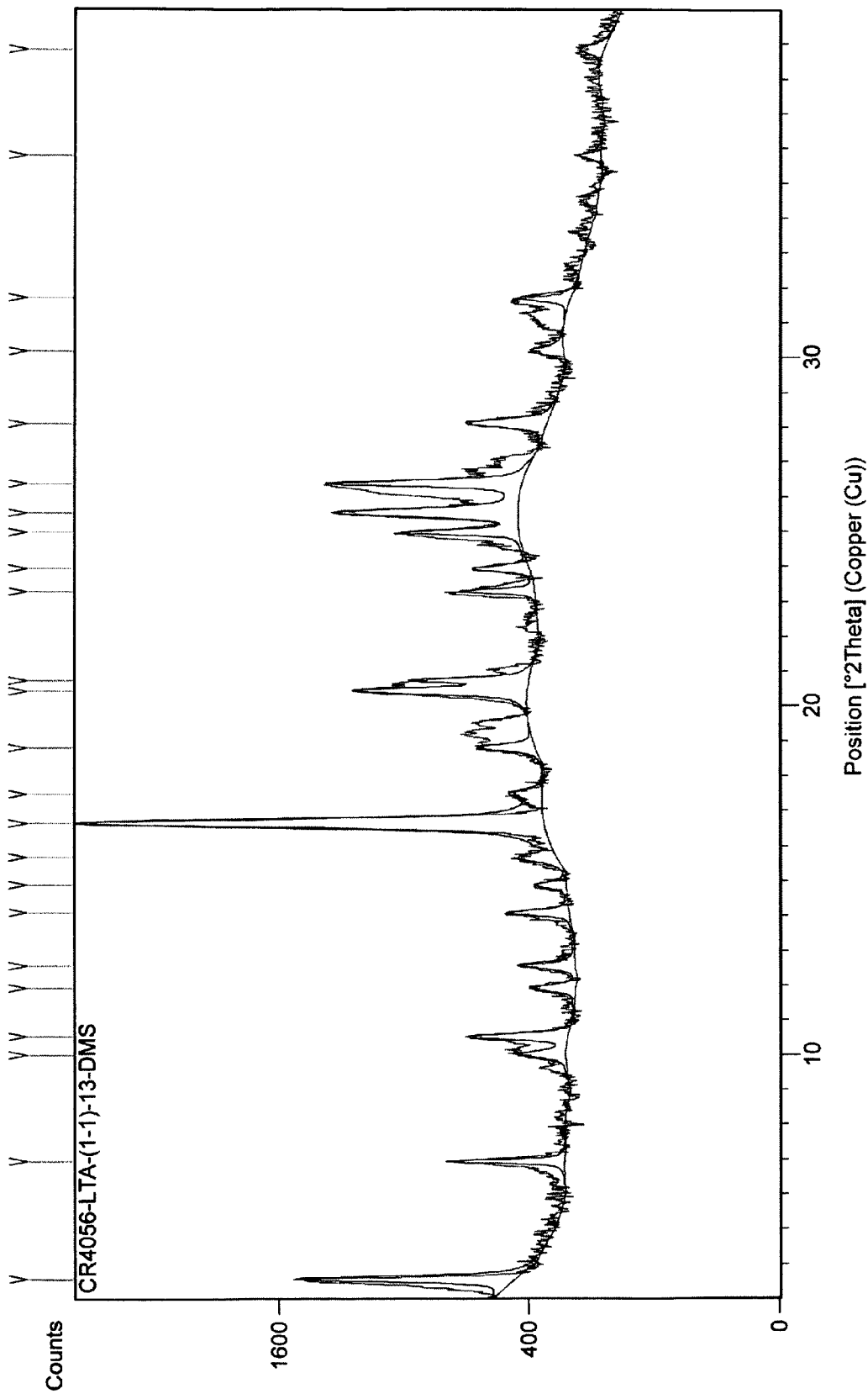
Figure 35: 6-(1H-imidazol-1-yl)-2-phenylquinazoline (L)-tartrate tetrahydrate, Form B, XRPD

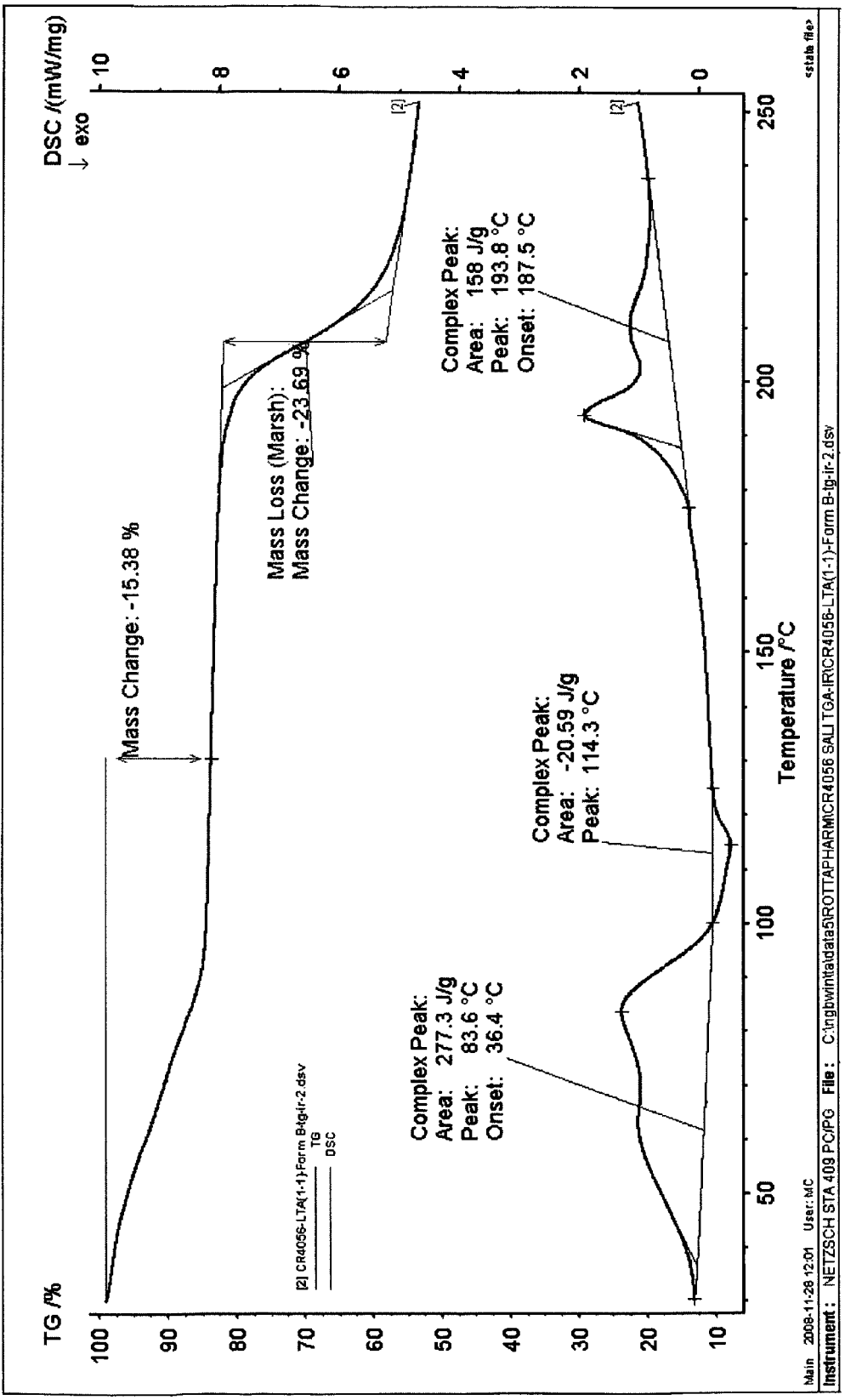
Figure 36: 6-(1H-imidazol-1-yl)-2-phenylquinazoline (L)-tartrate tetrahydrate, Form B, DSC

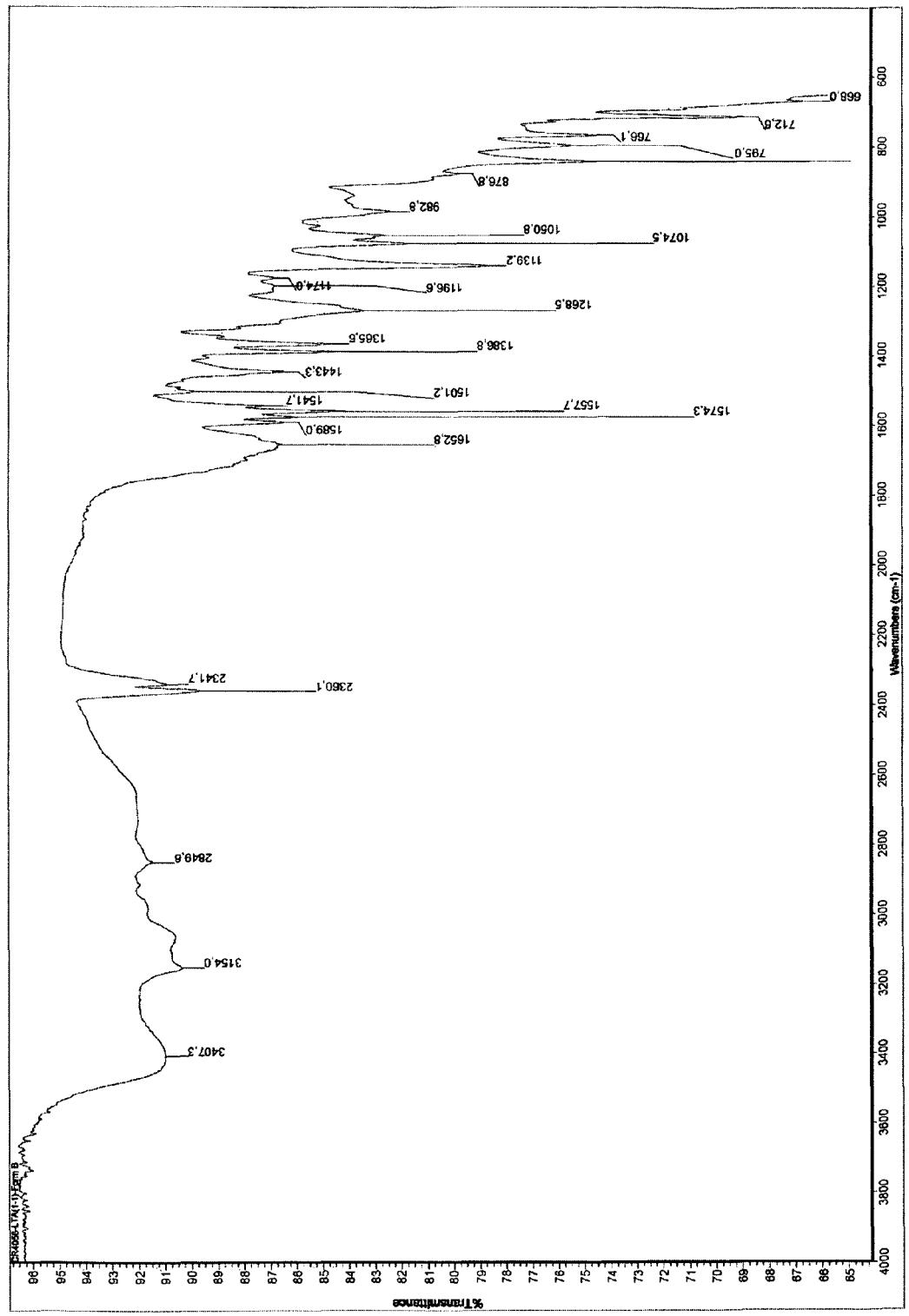
Figure 37: 6-(1H-imidazol-1-yl)-2-phenylquinazoline (L)-tartrate tetrahydrate, Form B, FT-

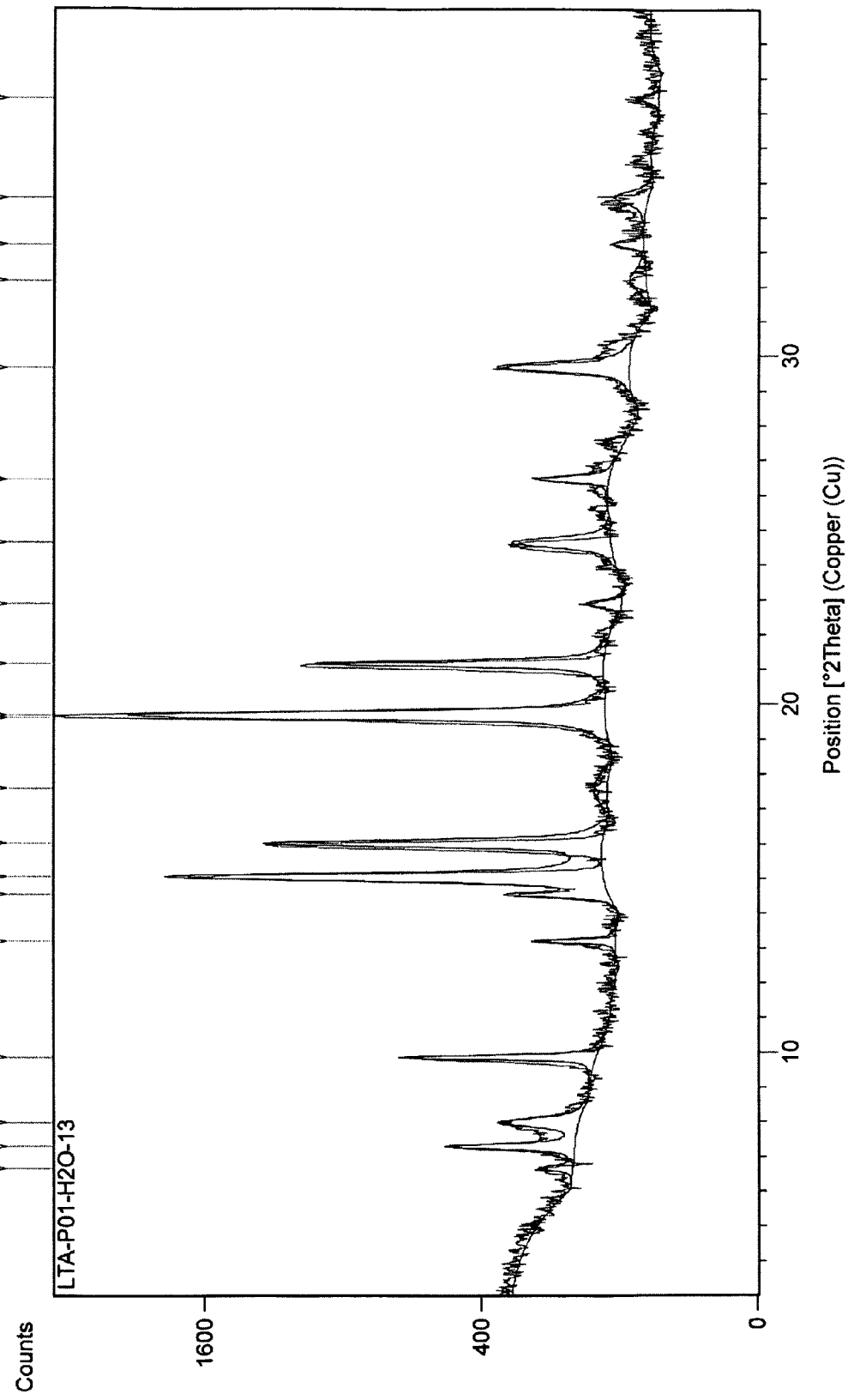
Figure 38: 6-(1H-imidazol-1-yl)-2-phenylquinazoline (L)-tartrate monohydrate, Form C, XRPD

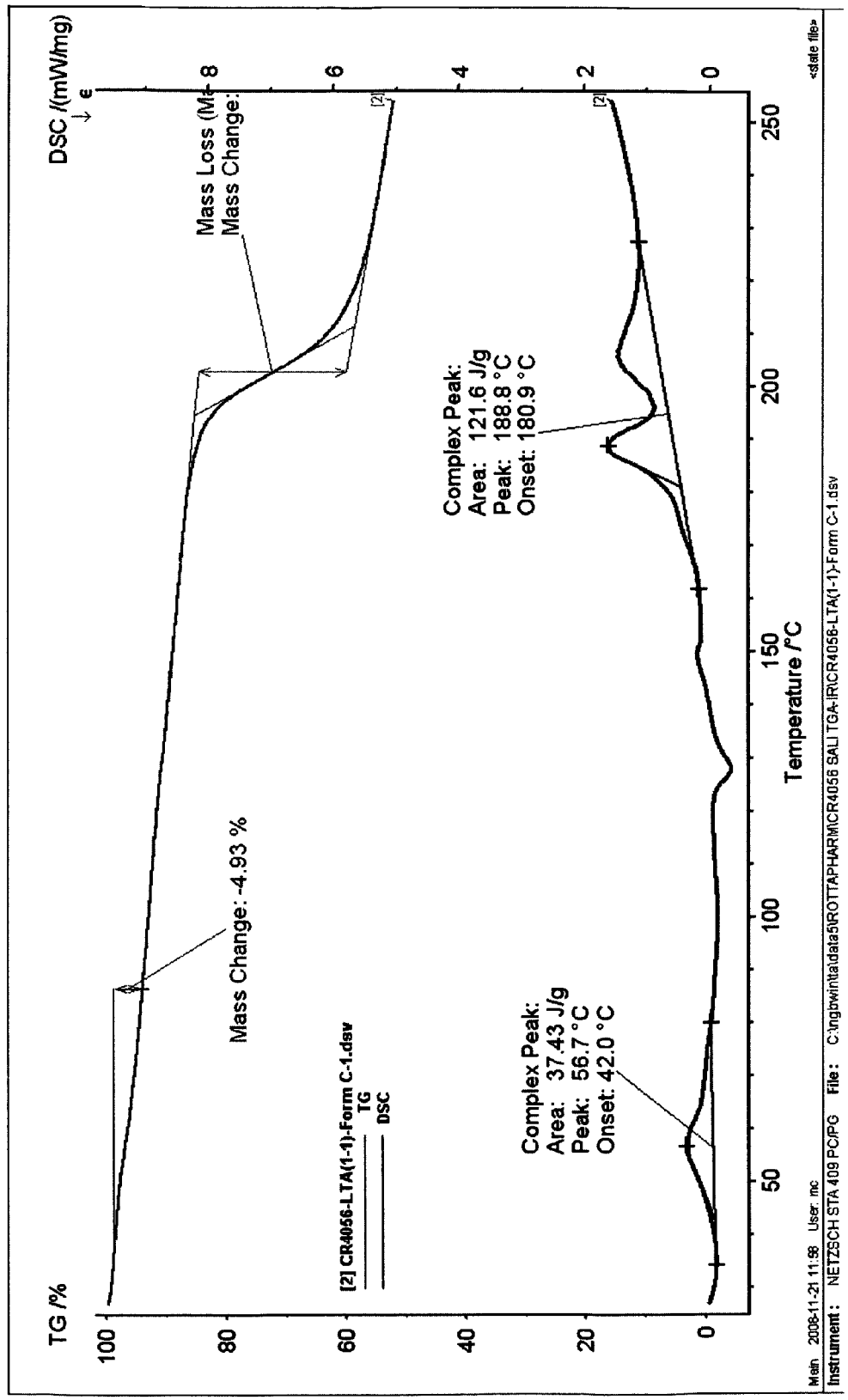
Figure 39: 6-(1H-imidazol-1-yl)-2-phenylquinazoline (L)-tartrate monohydrate, Form C, DSC

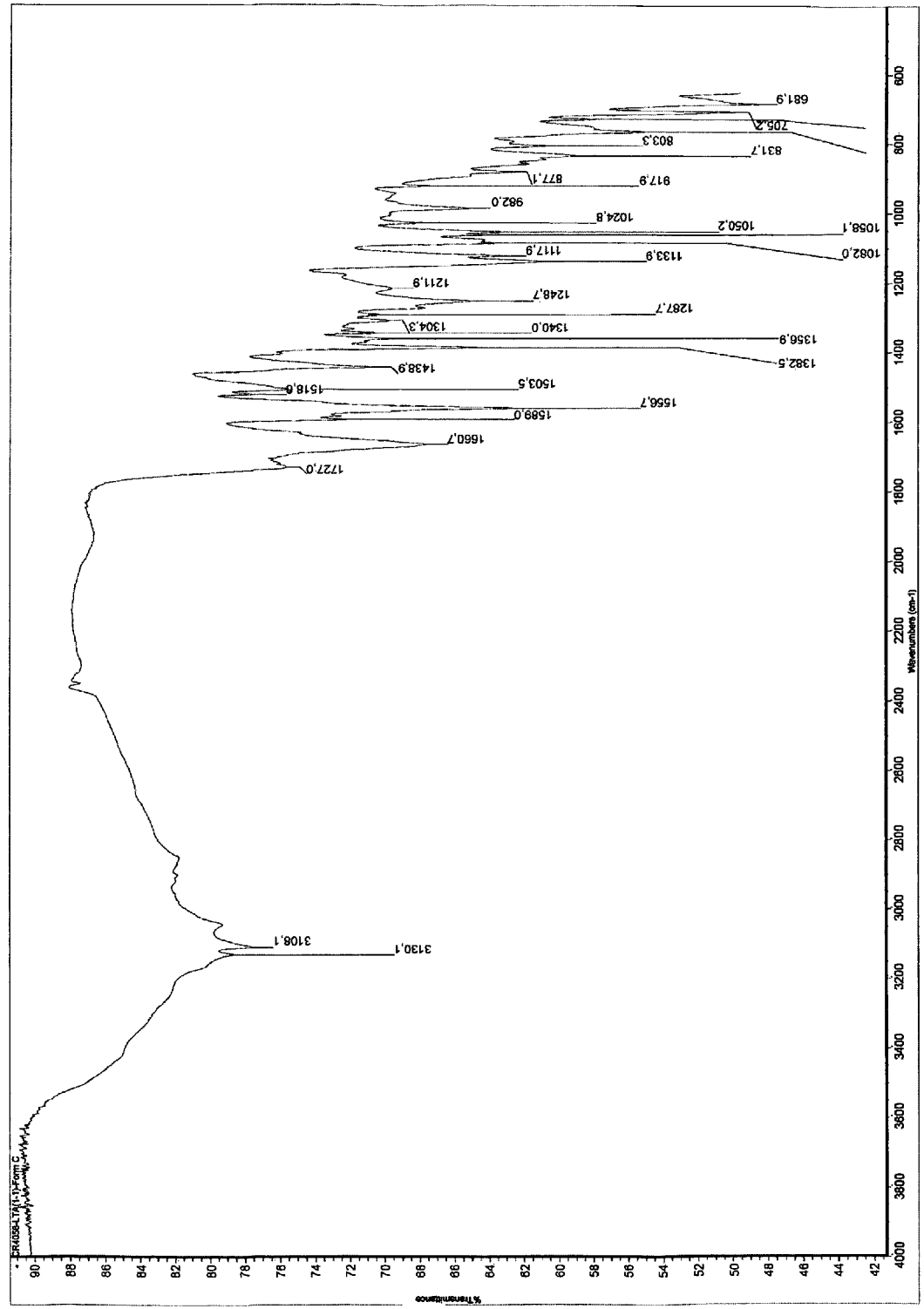

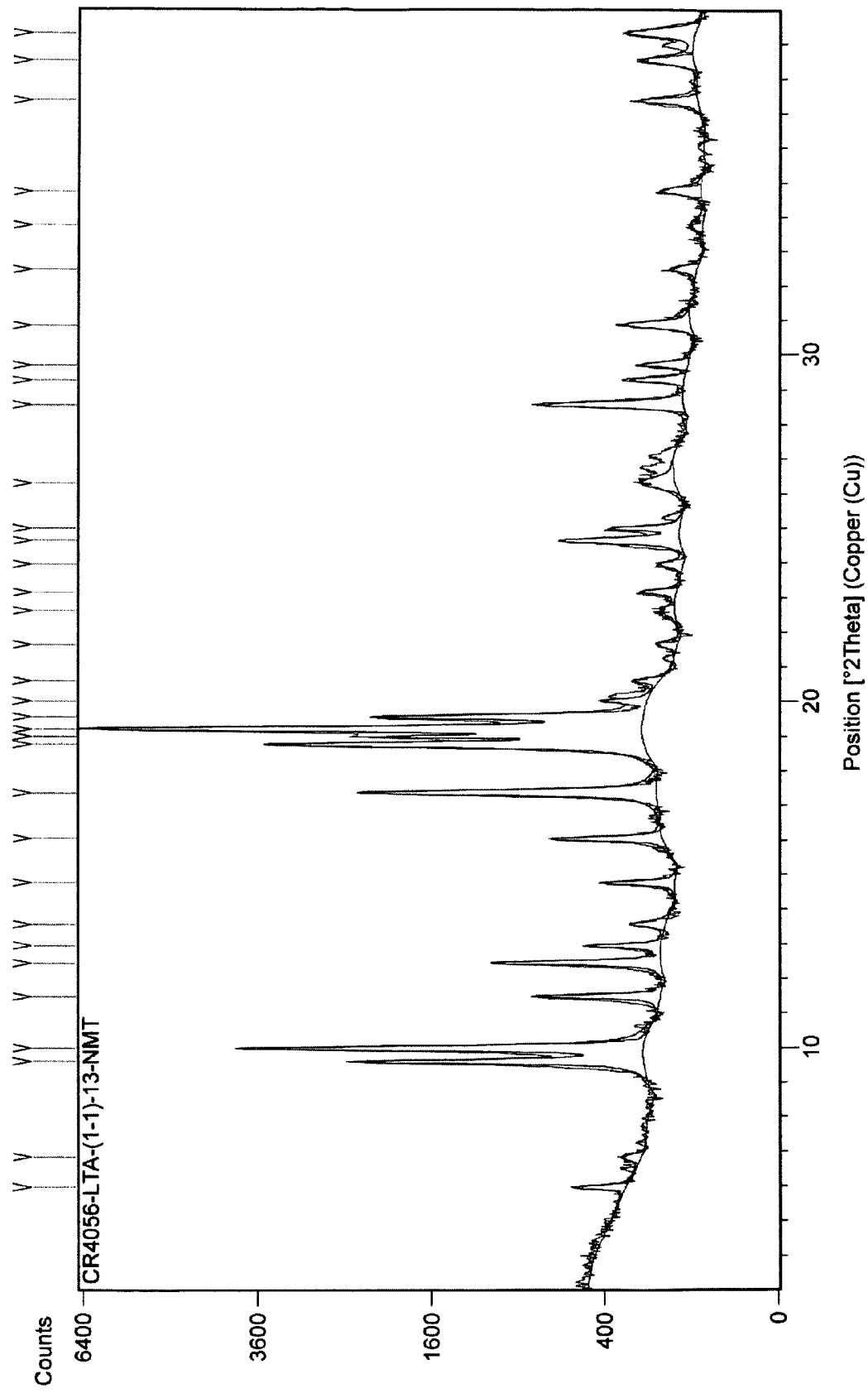

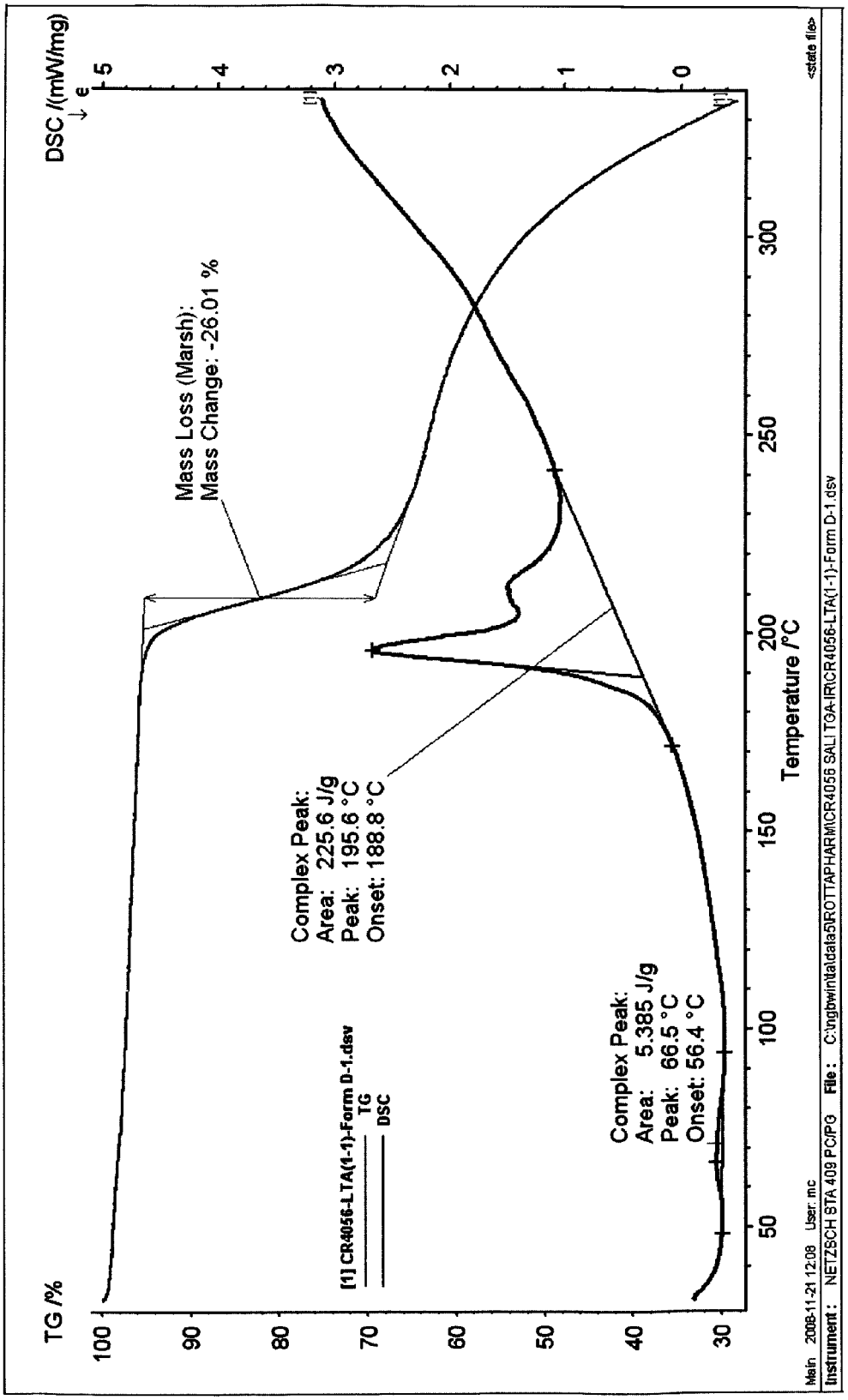
Figure 42: 6-(1H-imidazol-1-yl)-2-phenylquinazoline (L)-tartrate, Form D, DSC

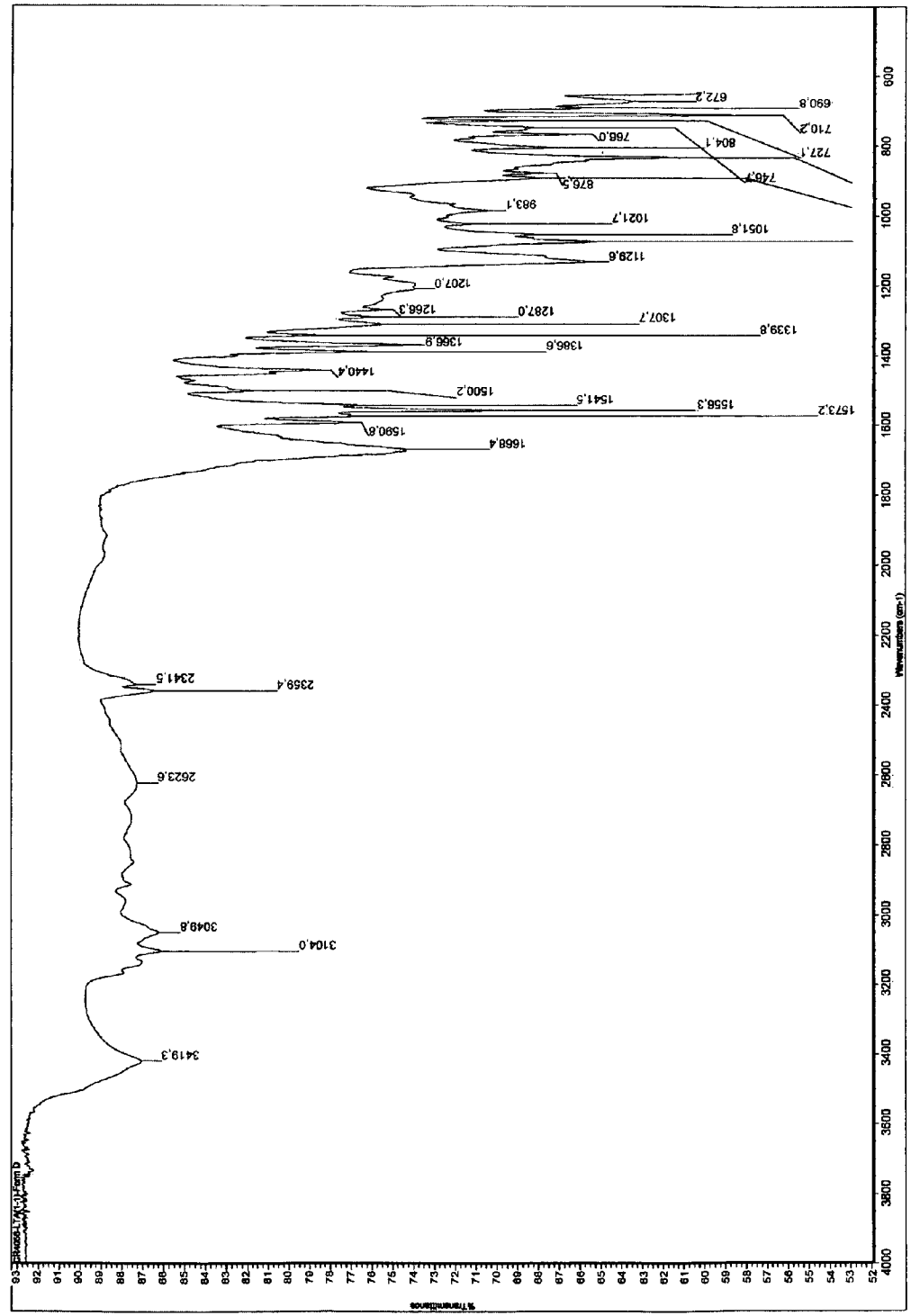
Figure 43: 6-(1H-imidazol-1-yl)-2-phenylquinazoline (L)-tartrate, Form D, FT-IR

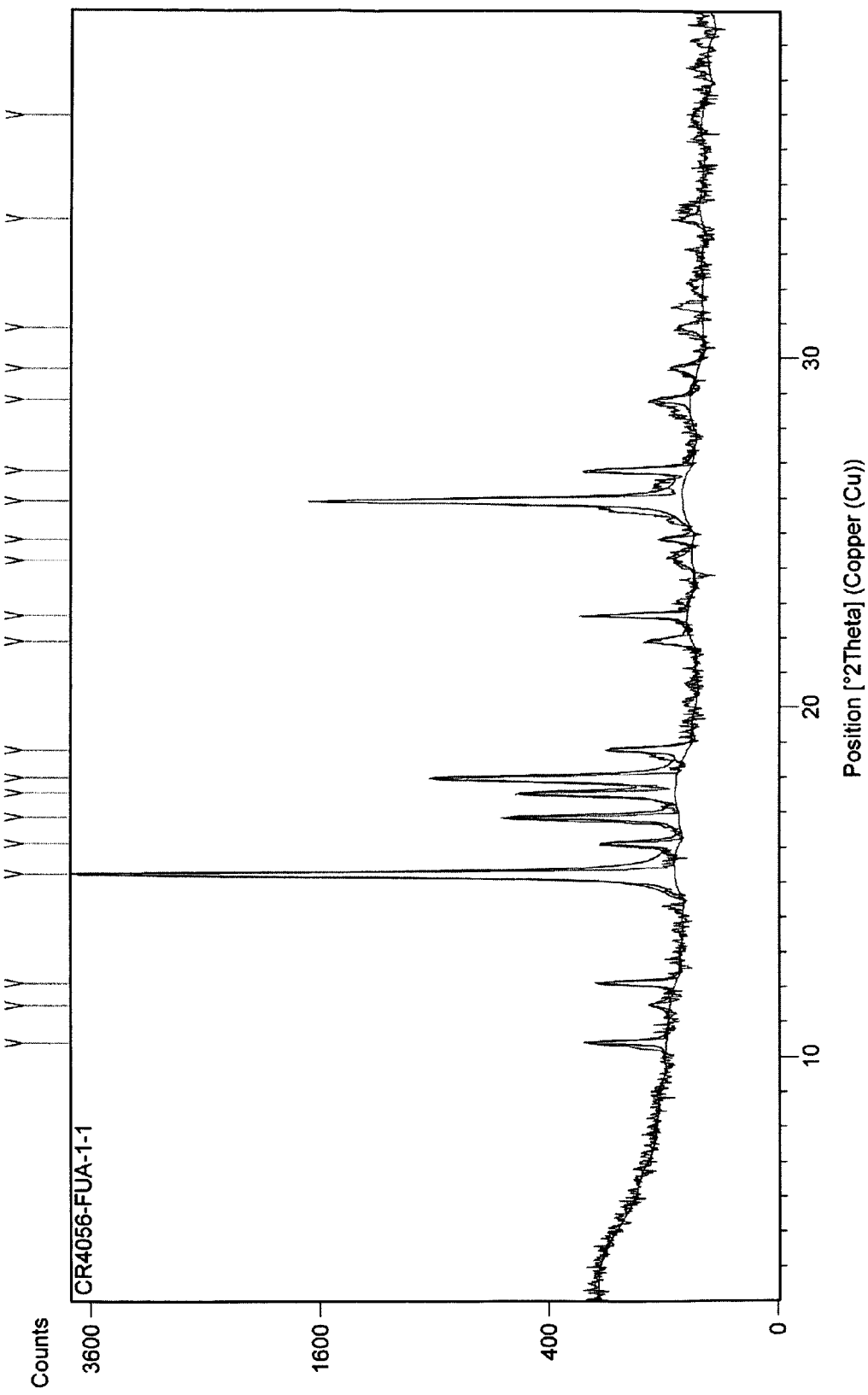

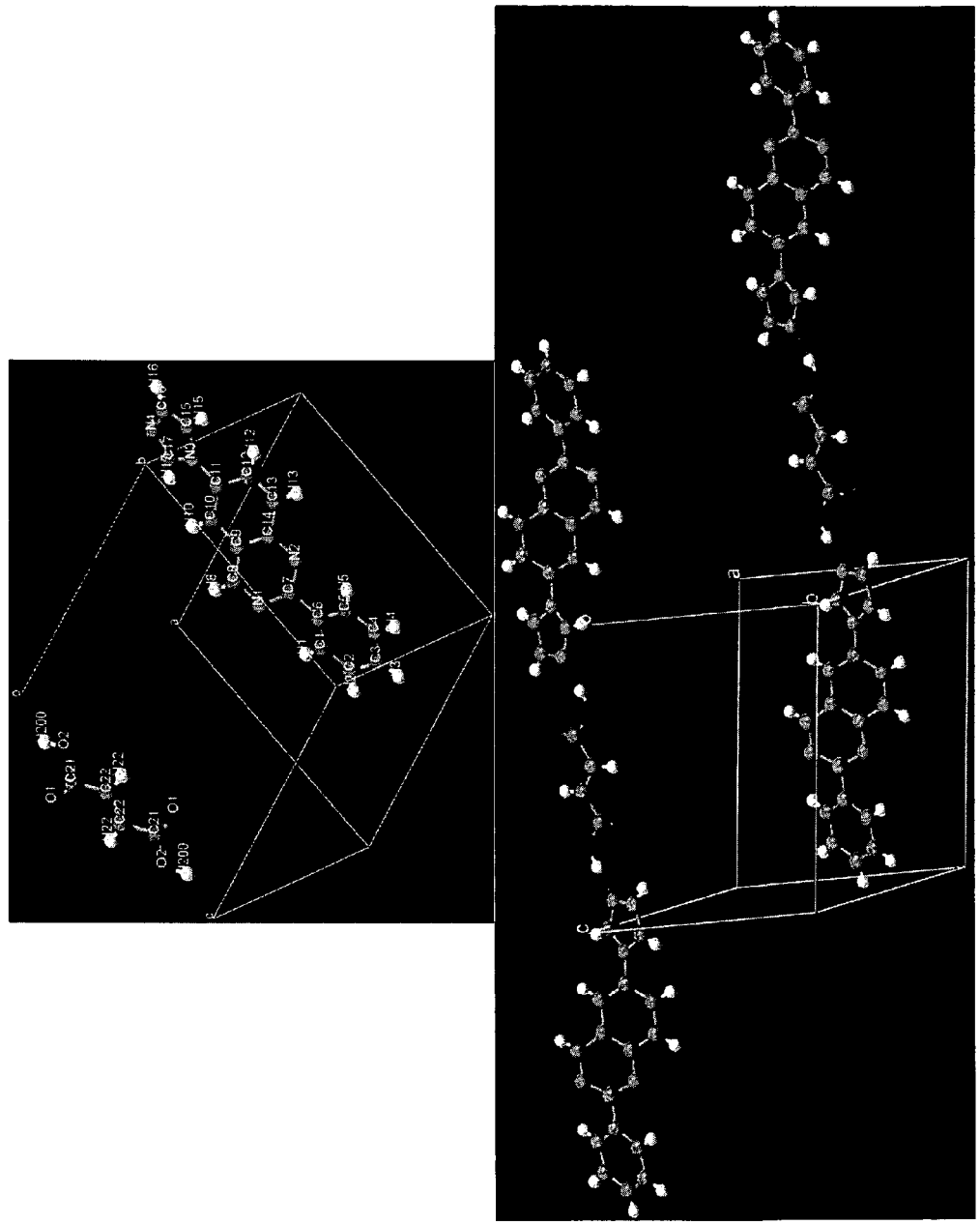
Figure 44a: three-dimensional structure of 6-(1H-imidazol-1-yl)-2-phenylquinazoline fumarate, Form A obtained by SC-RX

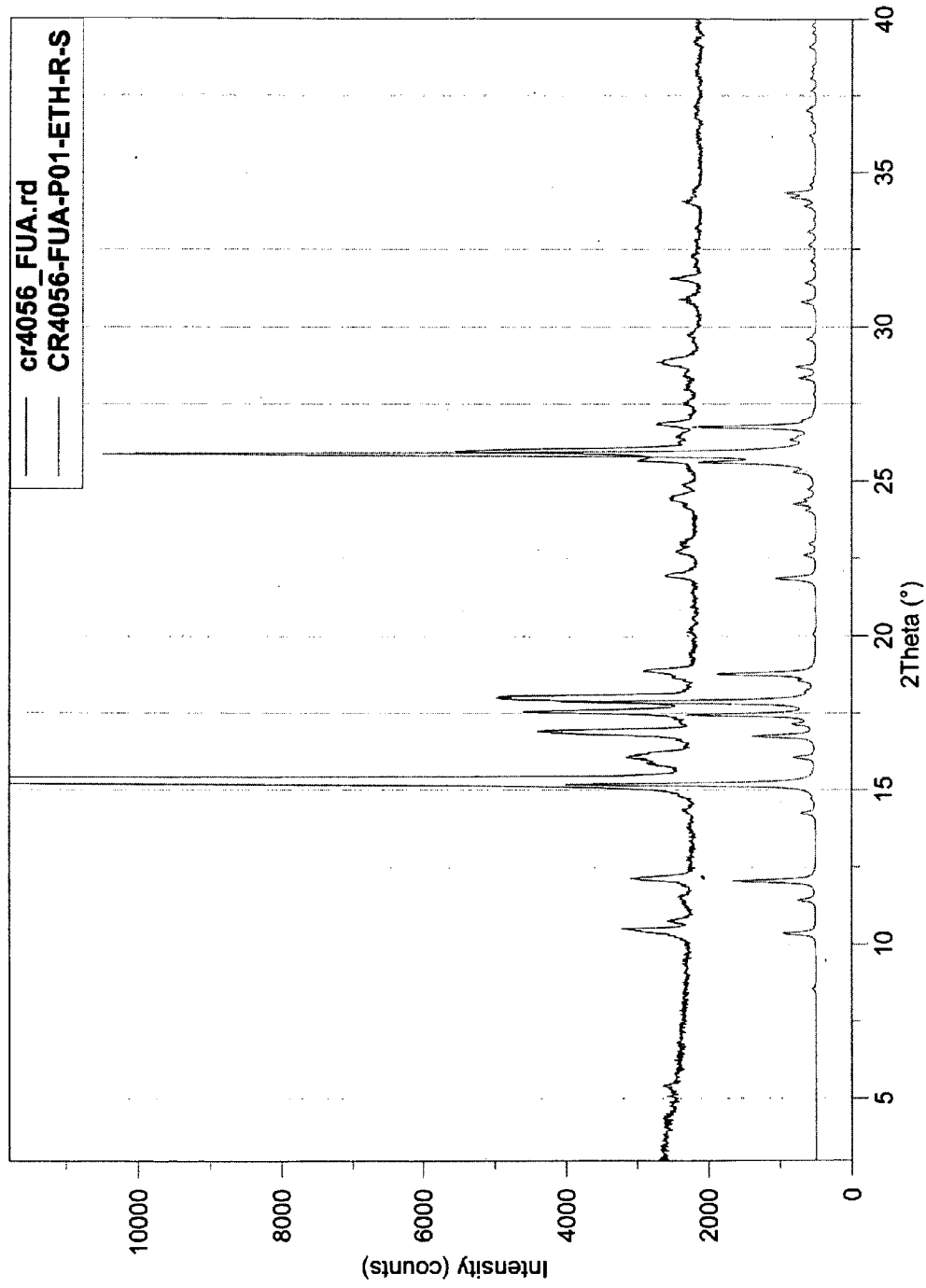
Figure 44b: comparison between the powder diffractogram calculated on the basis of the obtained structure and the experimental XRPD

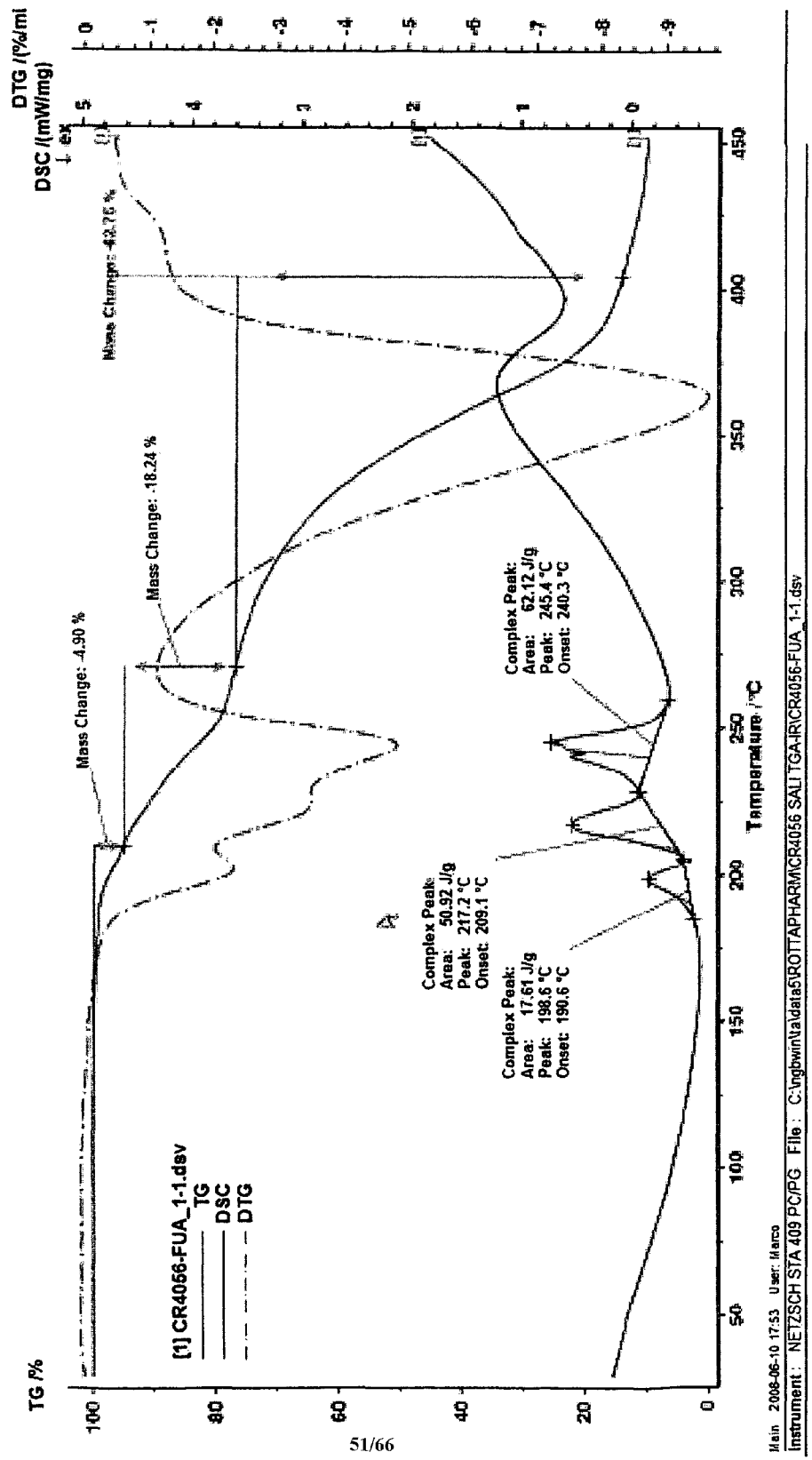
Figure 45: 6-(1H-imidazol-1-yl)-2-phenylquinazoline fumarate, Form A, DSC

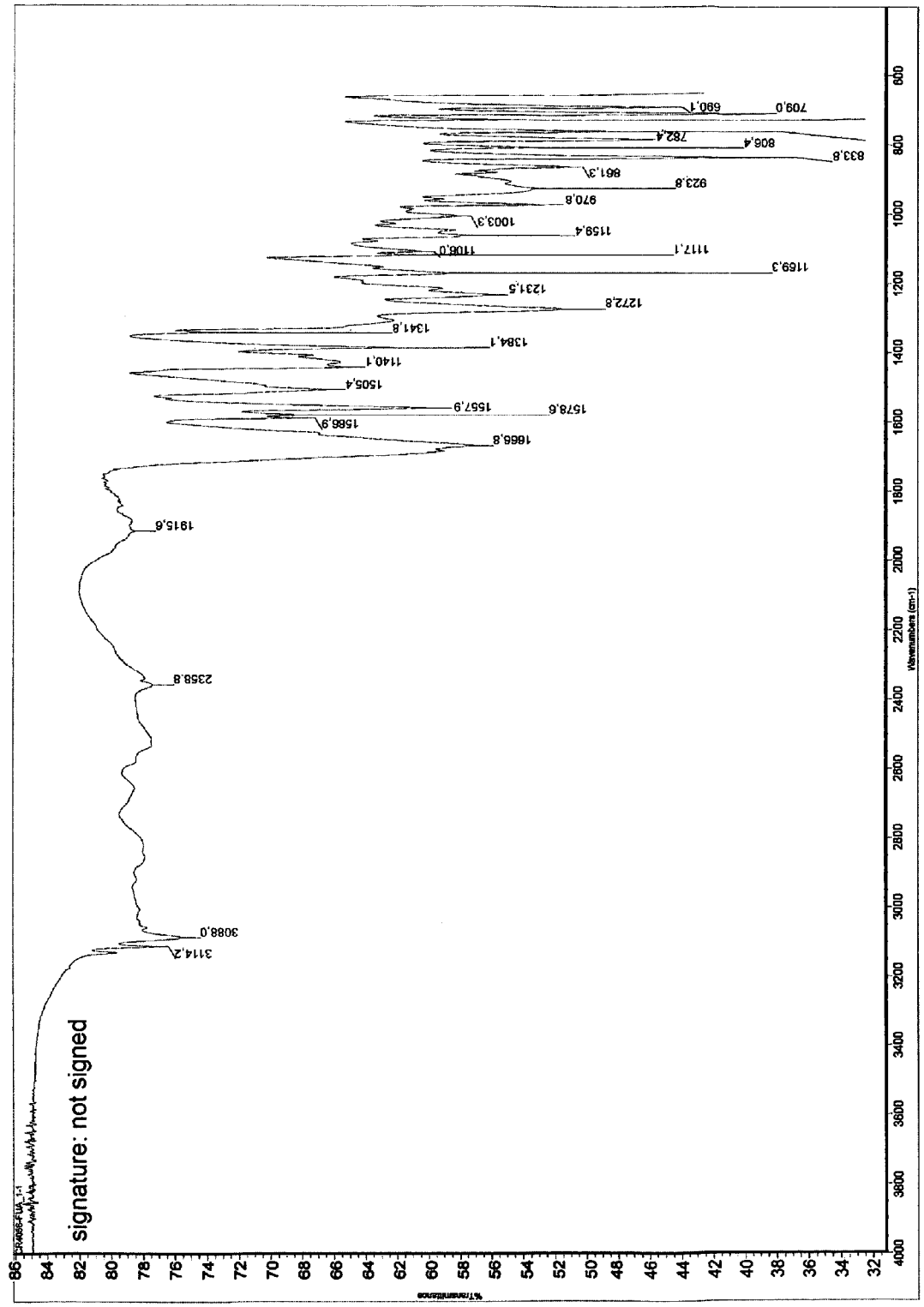
Figure 46: (1H-imidazol-1-yl)-2-phenylquinazoline fumarate, Form A, FT-IR

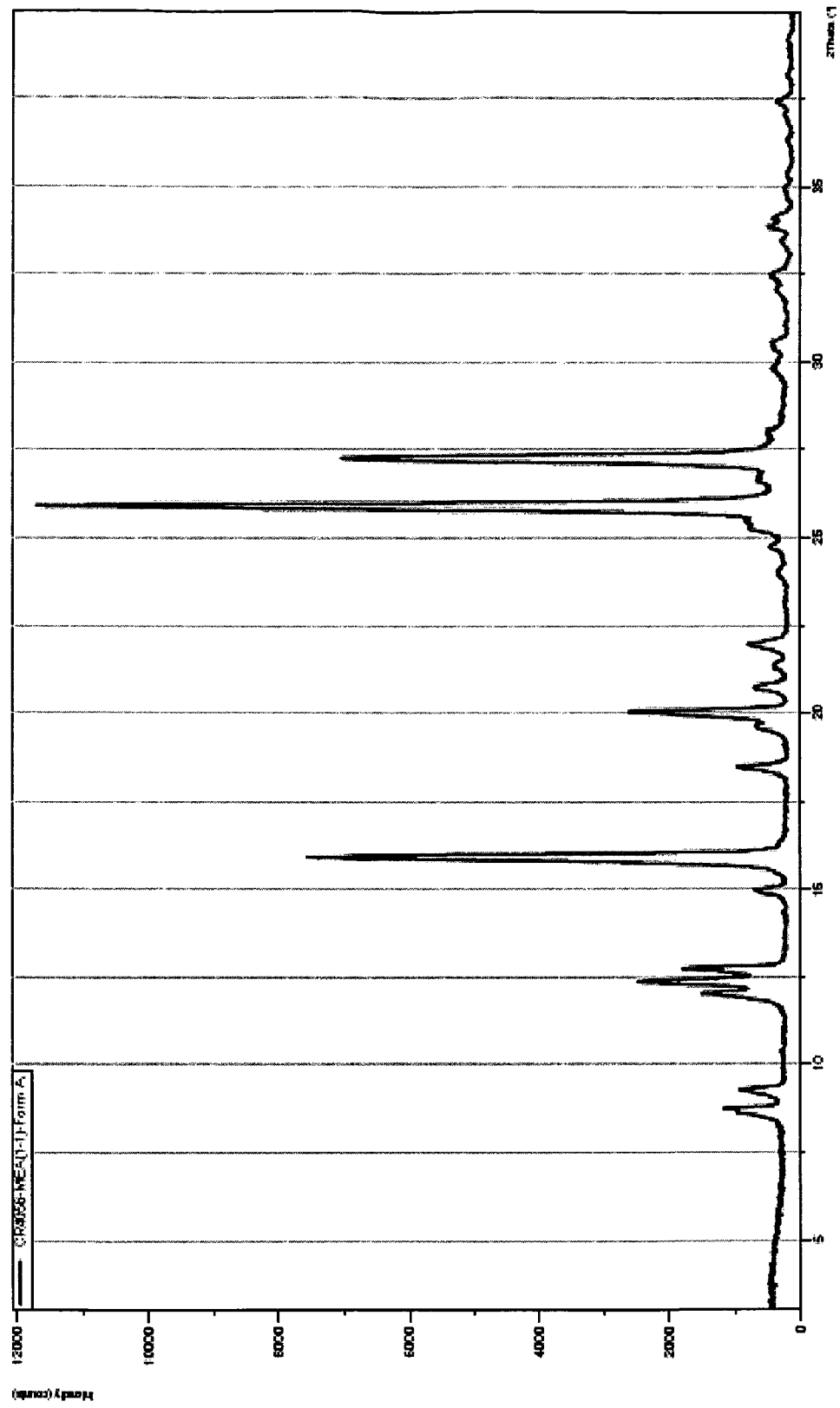
Figure 47: XRPD 6-(1H-imidazol-1-yl)-2-phenylquinazoline maleate, Form A

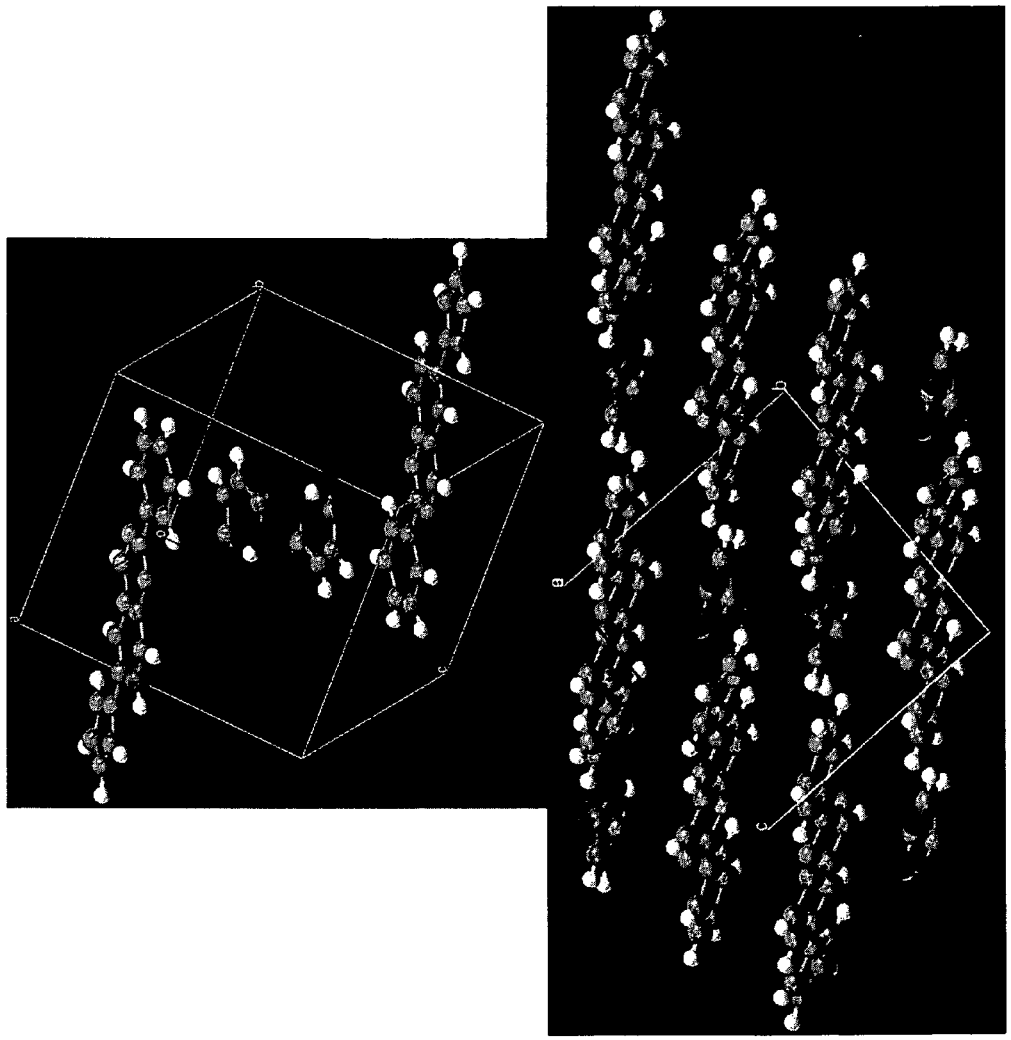
Figure 47a: three-dimensional structure of 6-(1H-imidazol-1-yl)-2-phenylquinazoline maleate, Form A obtained SC-RX

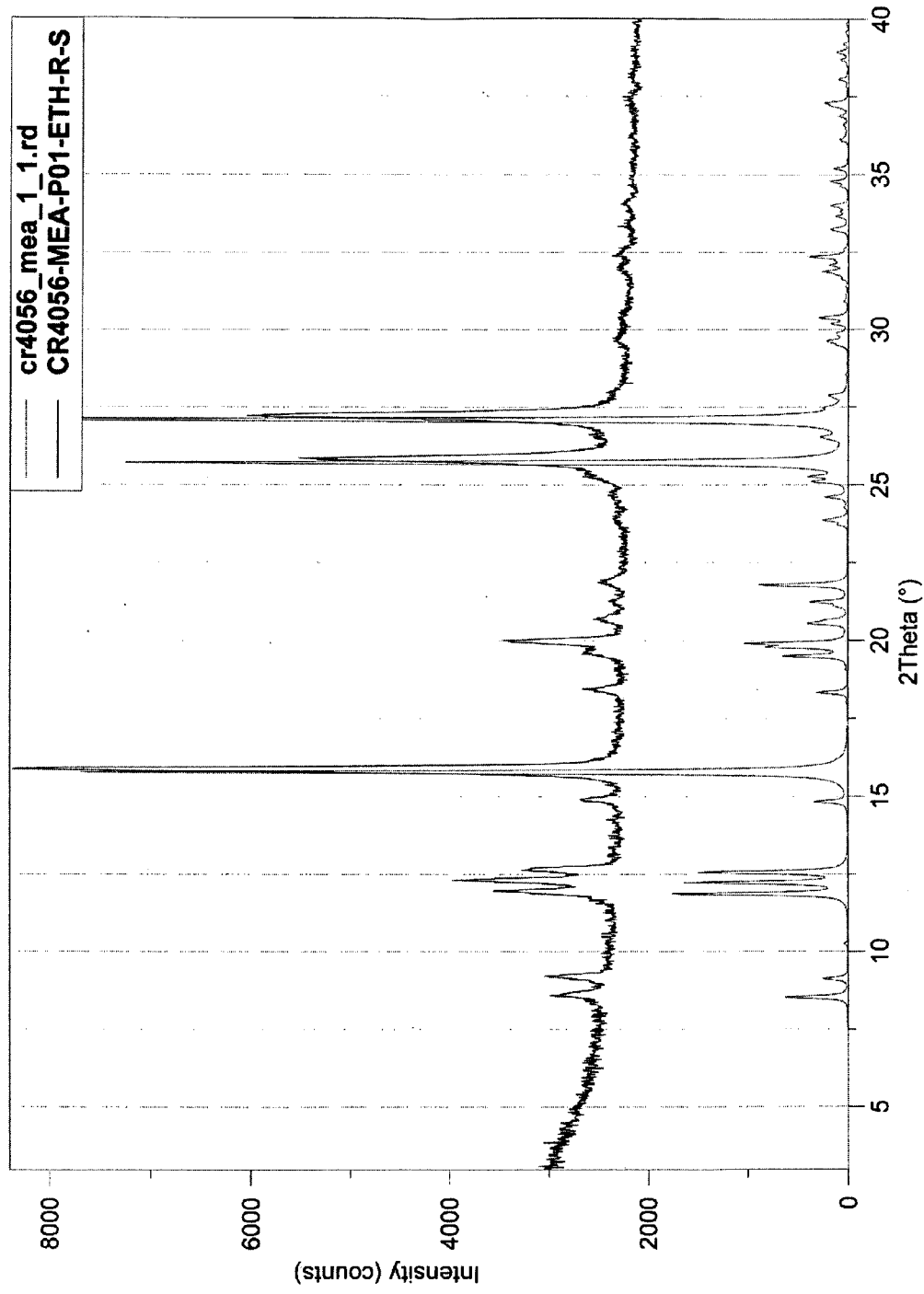
Figure 47b: comparison between the powder diffractogram calculated on the basis of the obtained structure and the experimental XRPD

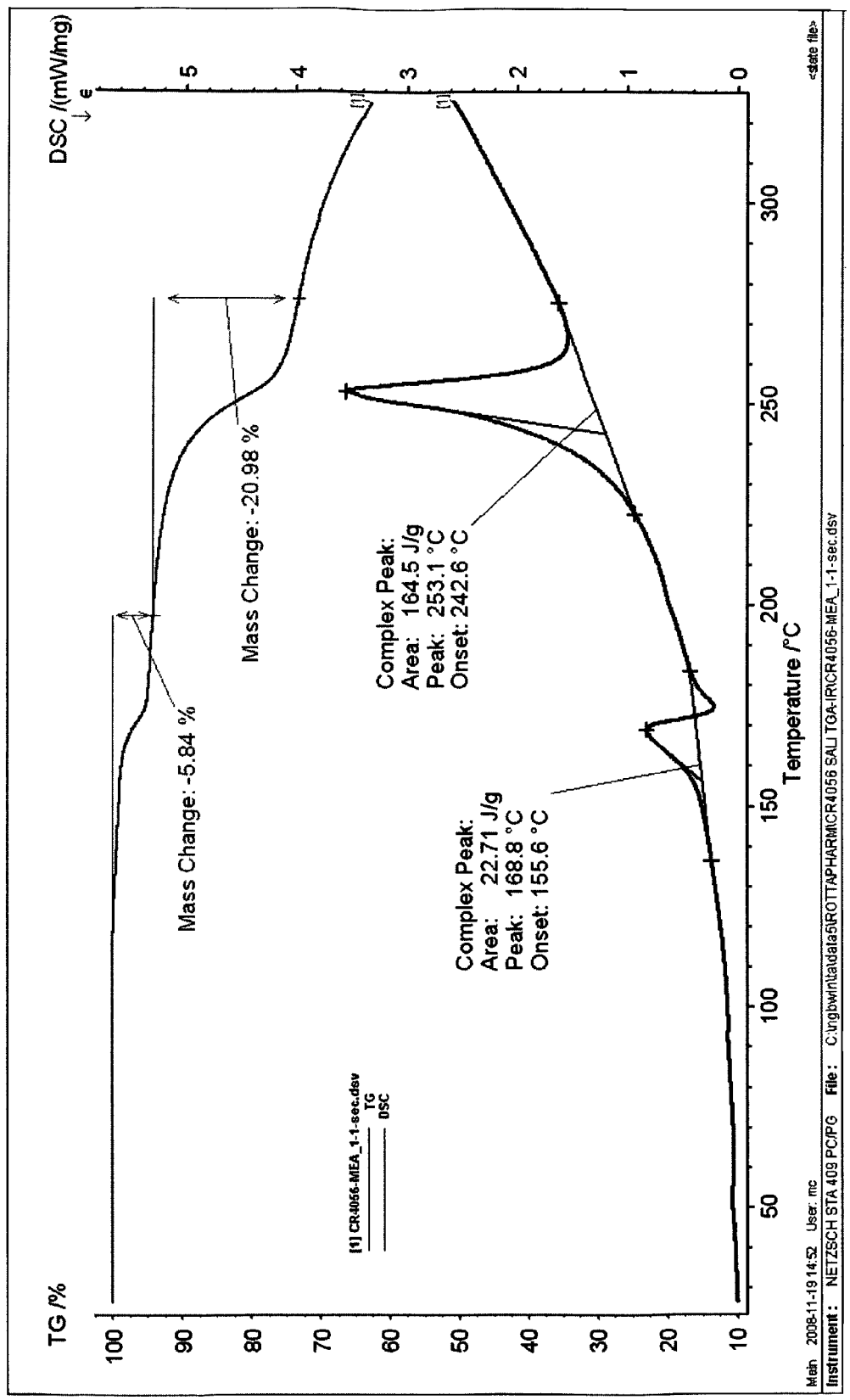
Figure 48: 6-(1H-imidazol-1-yl)-2-phenylquinazoline maleate, Form A, DSC

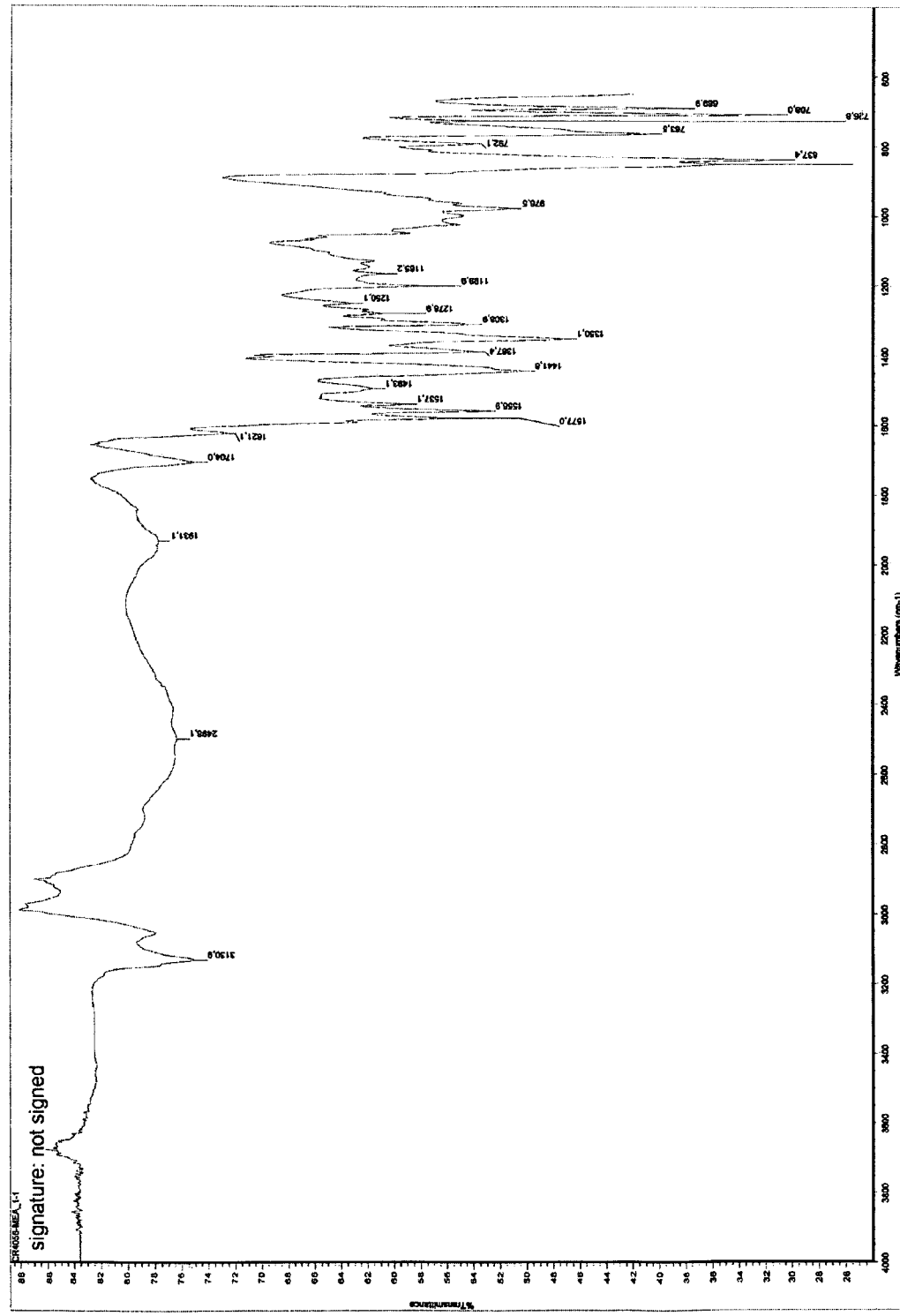
Figure 49: 6-(1H-imidazol-1-yl)-2-phenylquinazoline maleate, Form A, FT-IR

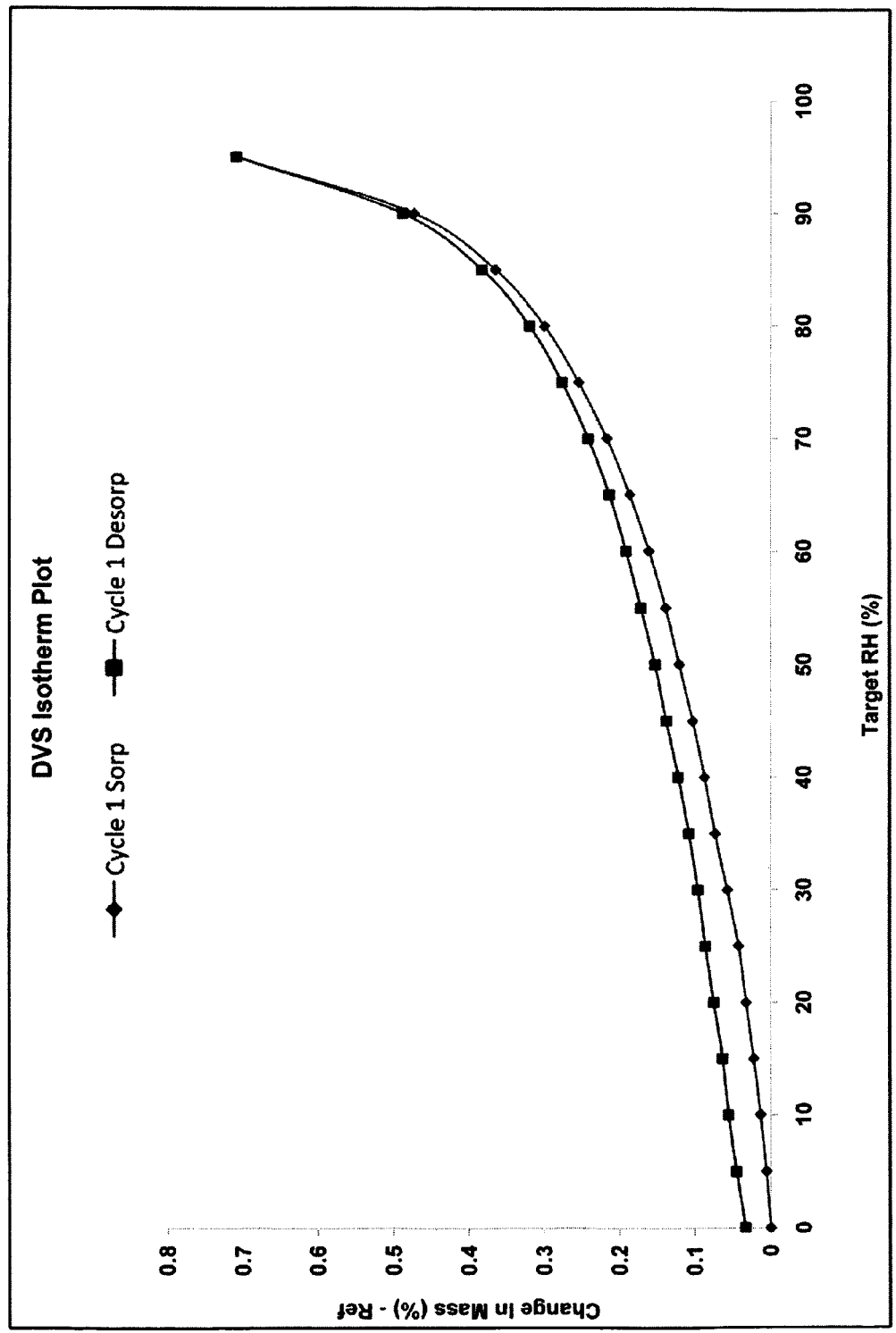
Figure 50a: 6-(1H-imidazol-1-yl)-2-phenylquinazoline maleate, form A, DVS

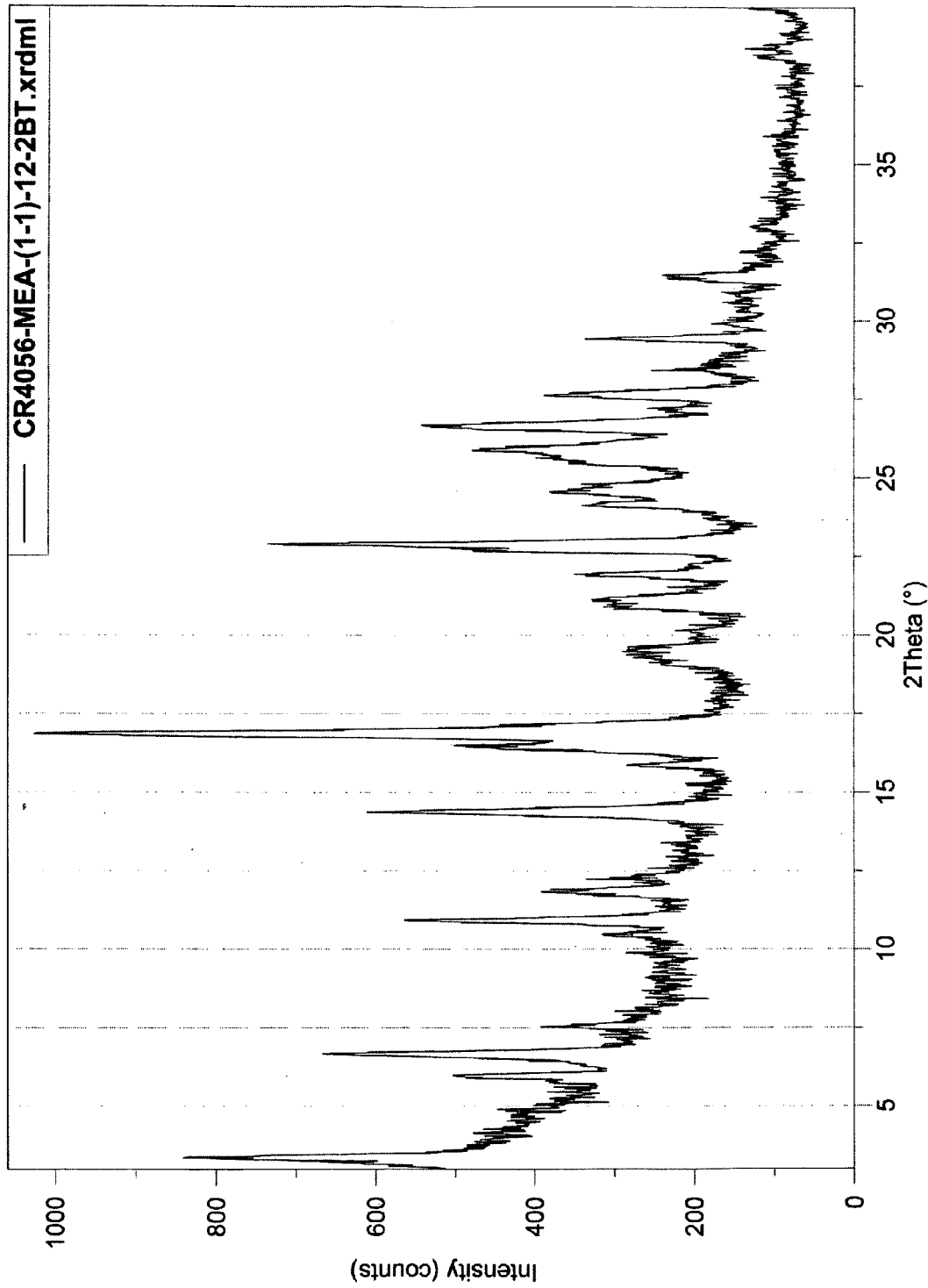
Figure 50b : 6-(1H-imidazol-1-yl)-2-phenylquinazoline maleate, Form A, DVS

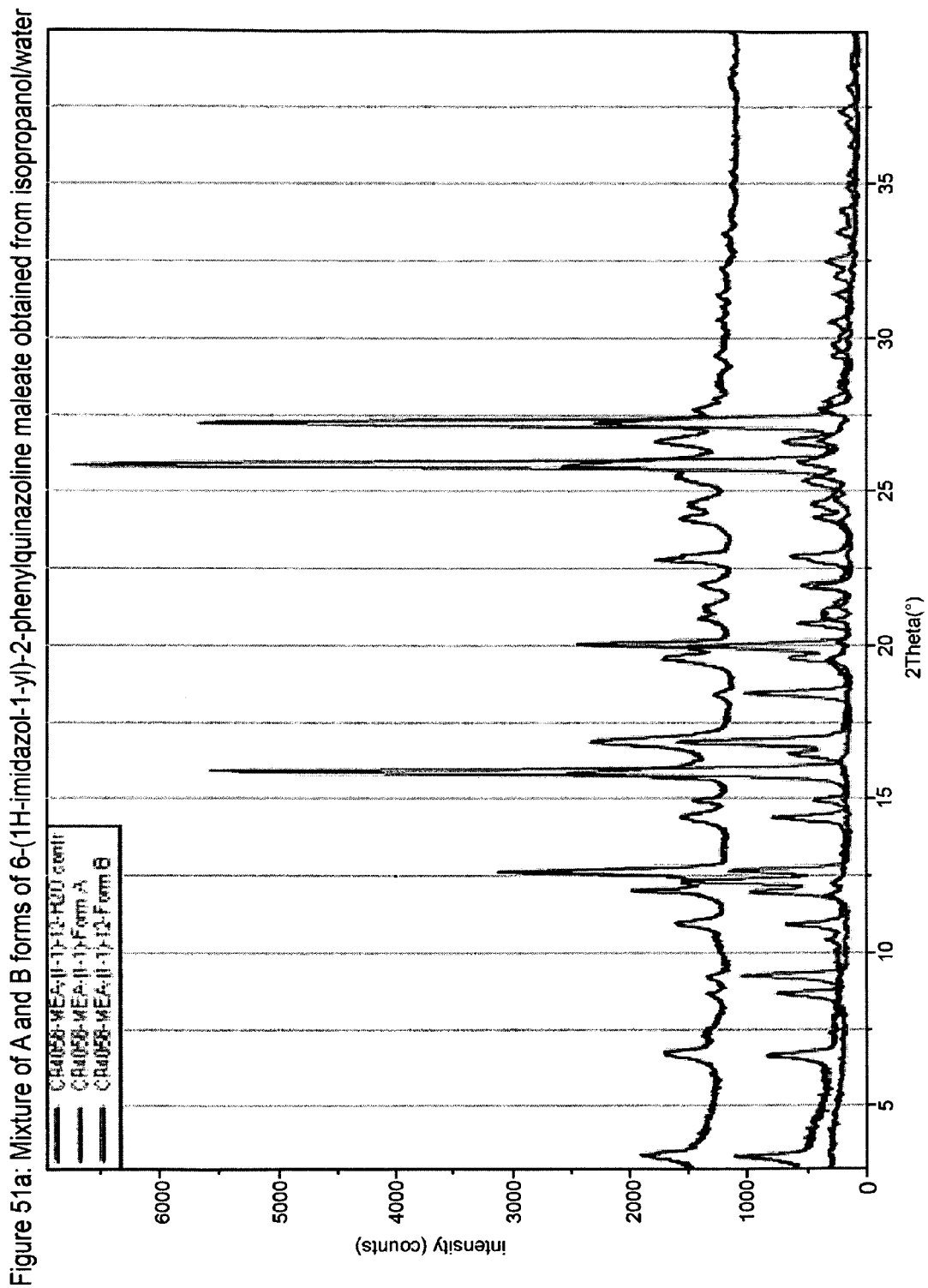

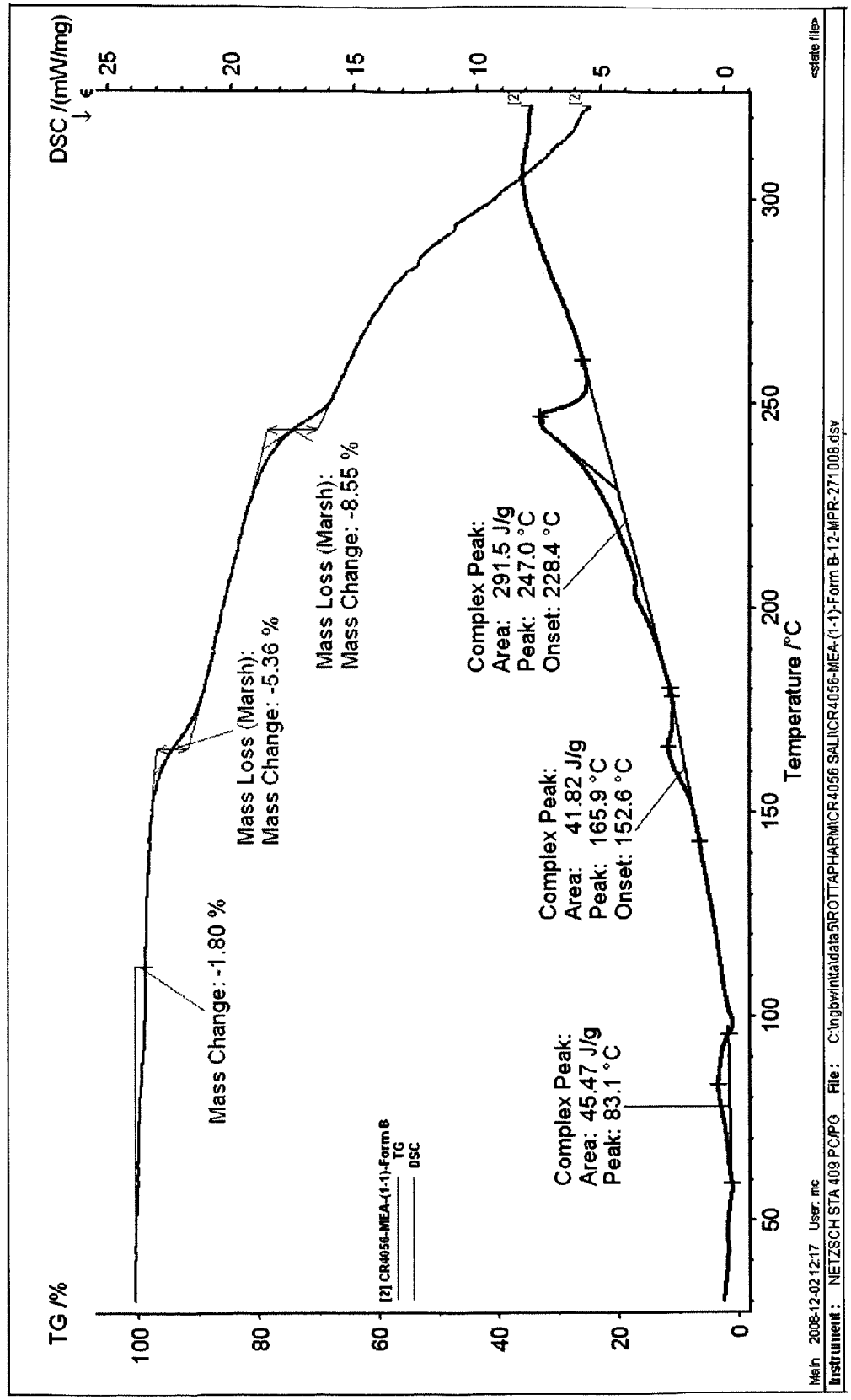
Figure 51b: 6-(1H-imidazol-1-yl)-2-phenylquinazoline maleate, Form B, DSC

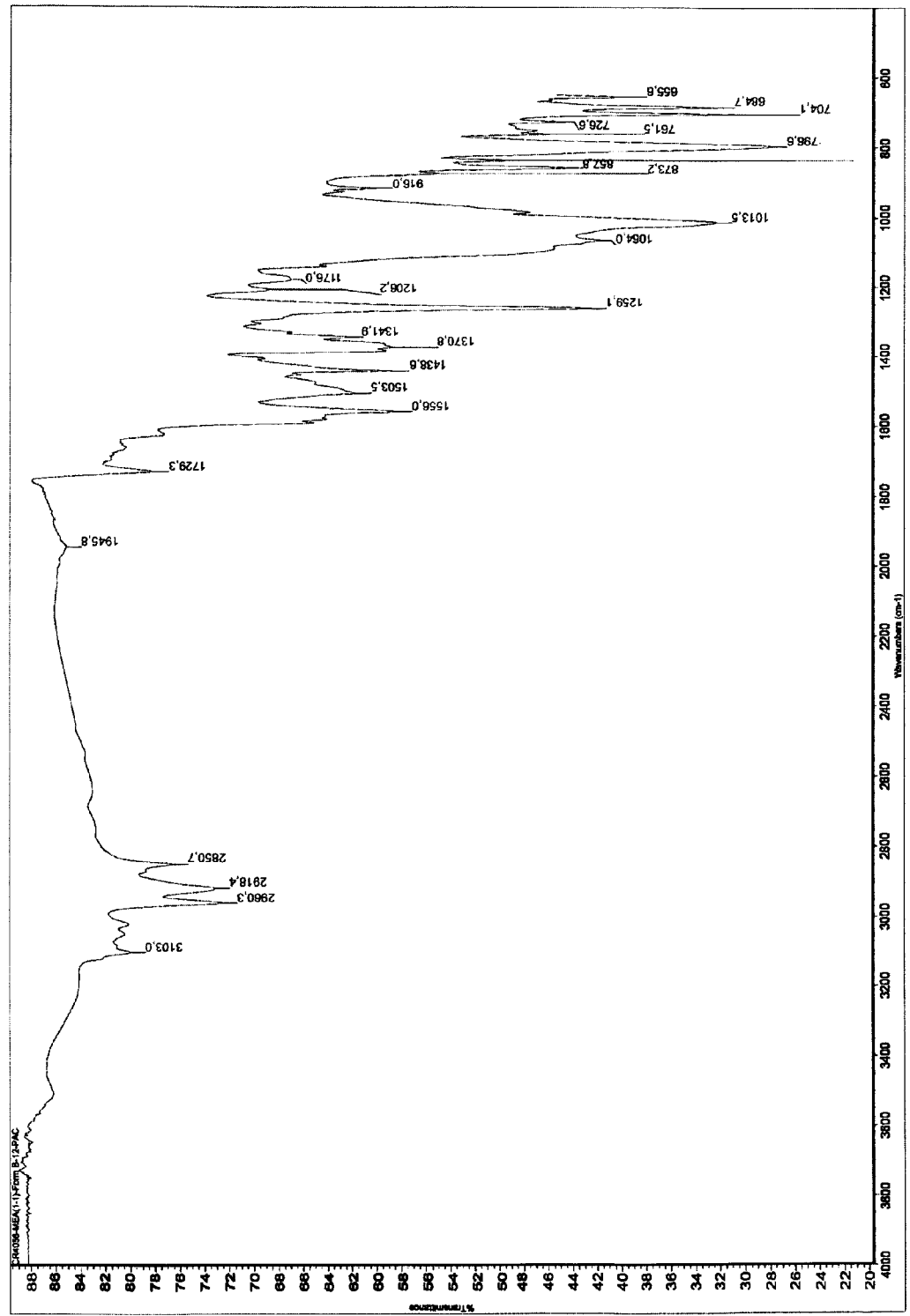
Figure 52: 6-(1H-imidazol-1-yl)-2-phenylquinazoline maleate, Form B, FT-IR

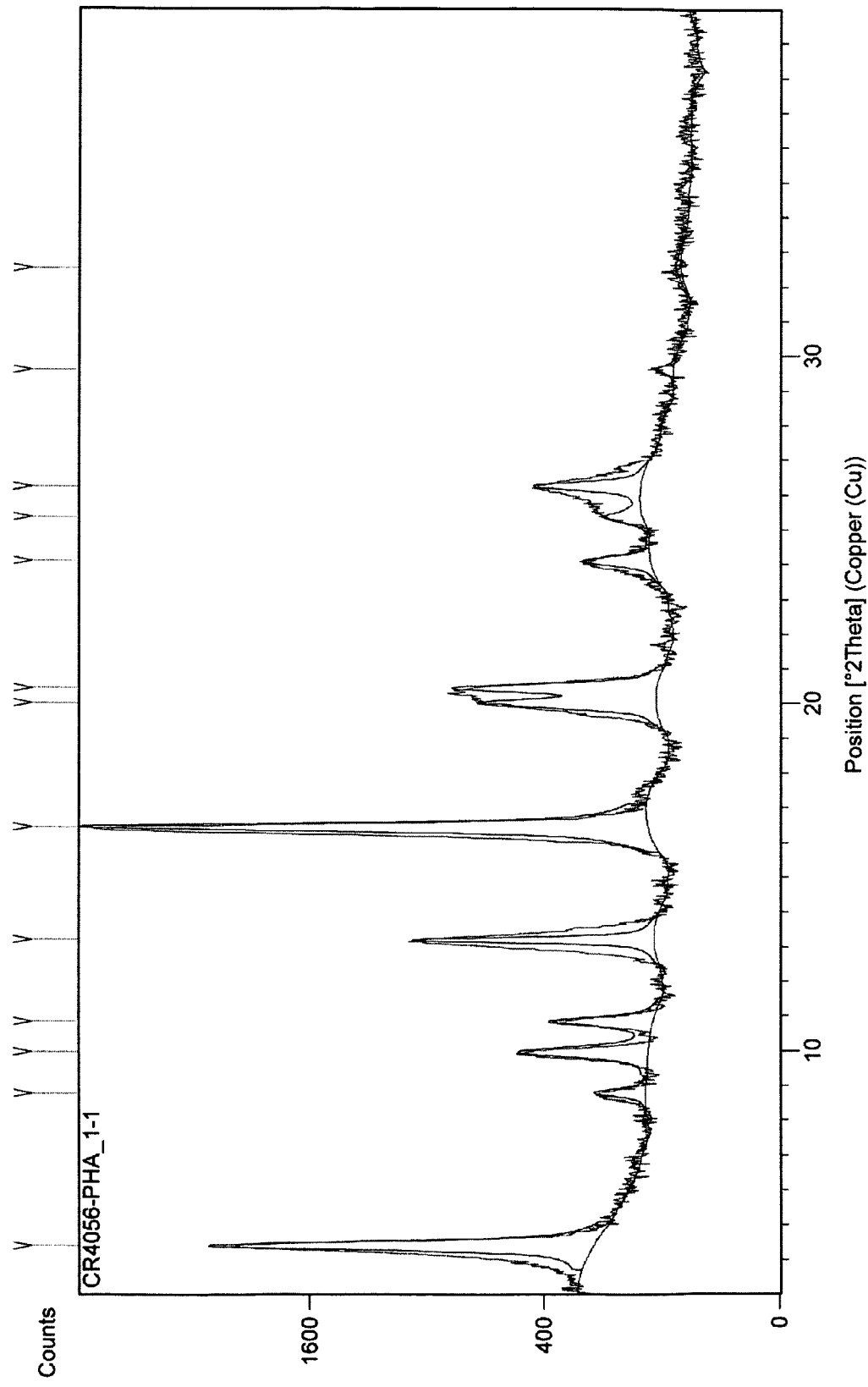
Figure 53: 6-(1H-imidazol-1-yl)-2-phenylquinazoline phosphate, Form A, XRPD

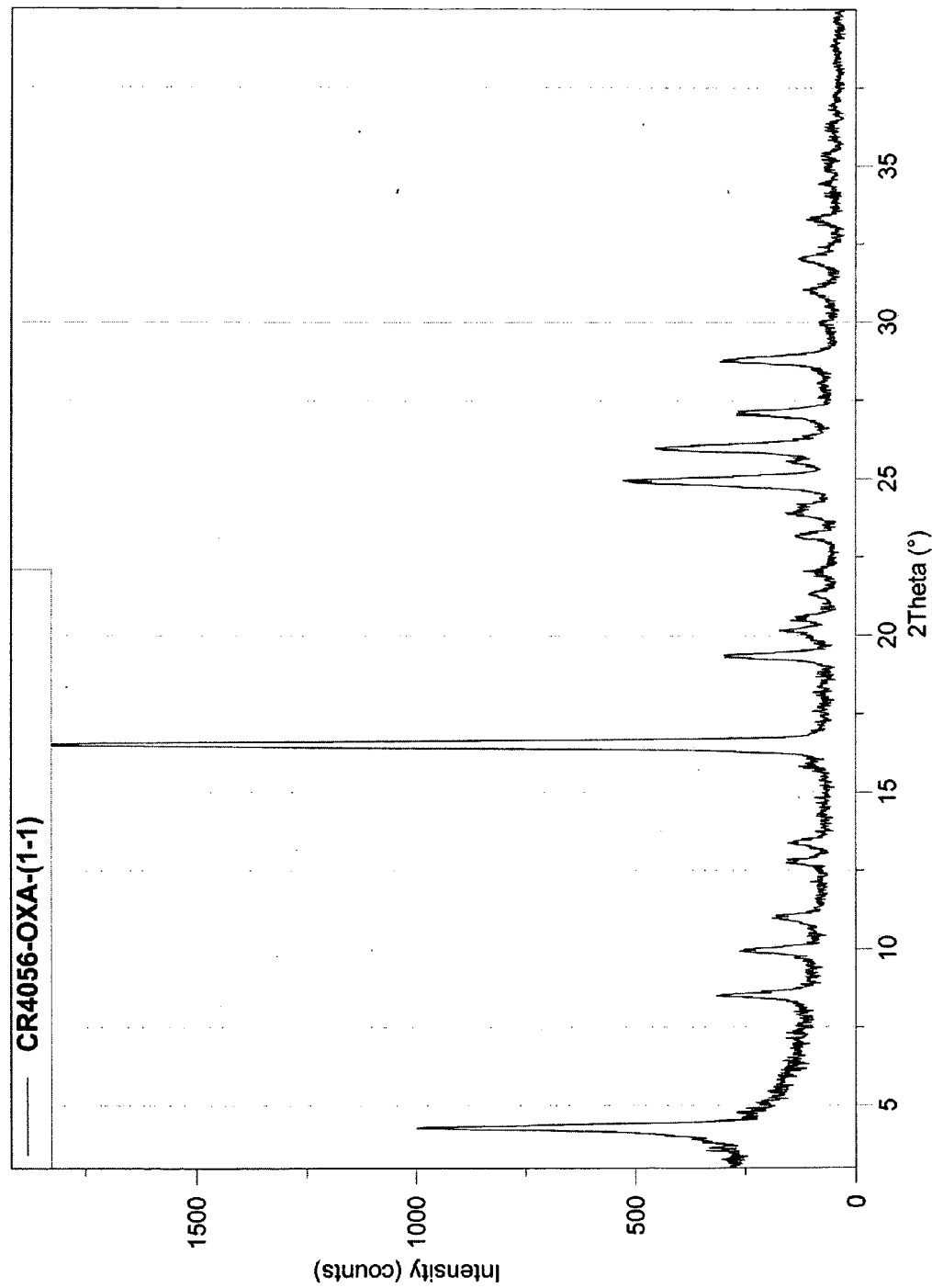

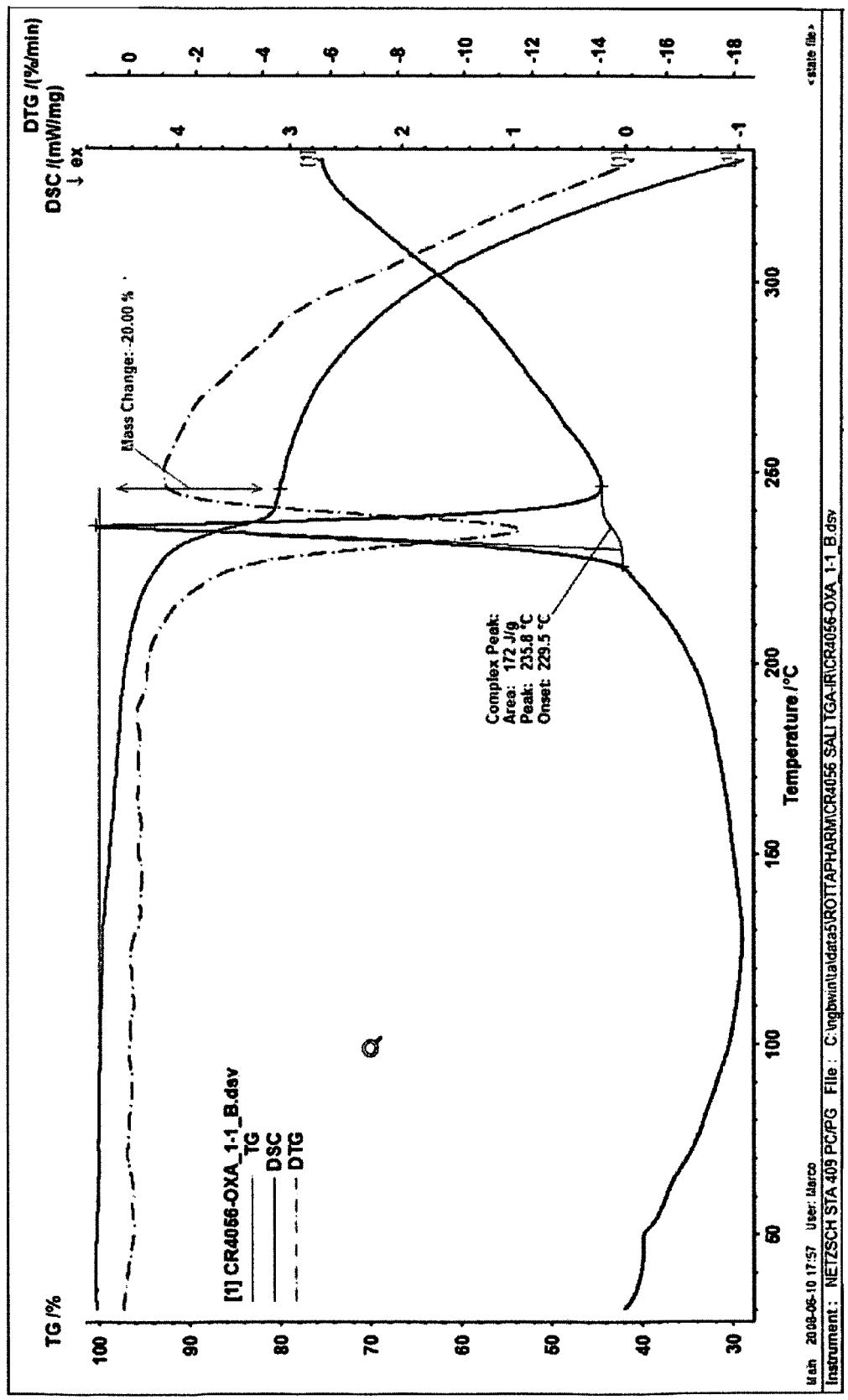
Figure 55: 6-(1H-imidazol-1-yl)-2-phenylquinazoline oxalate, Form A, DSC

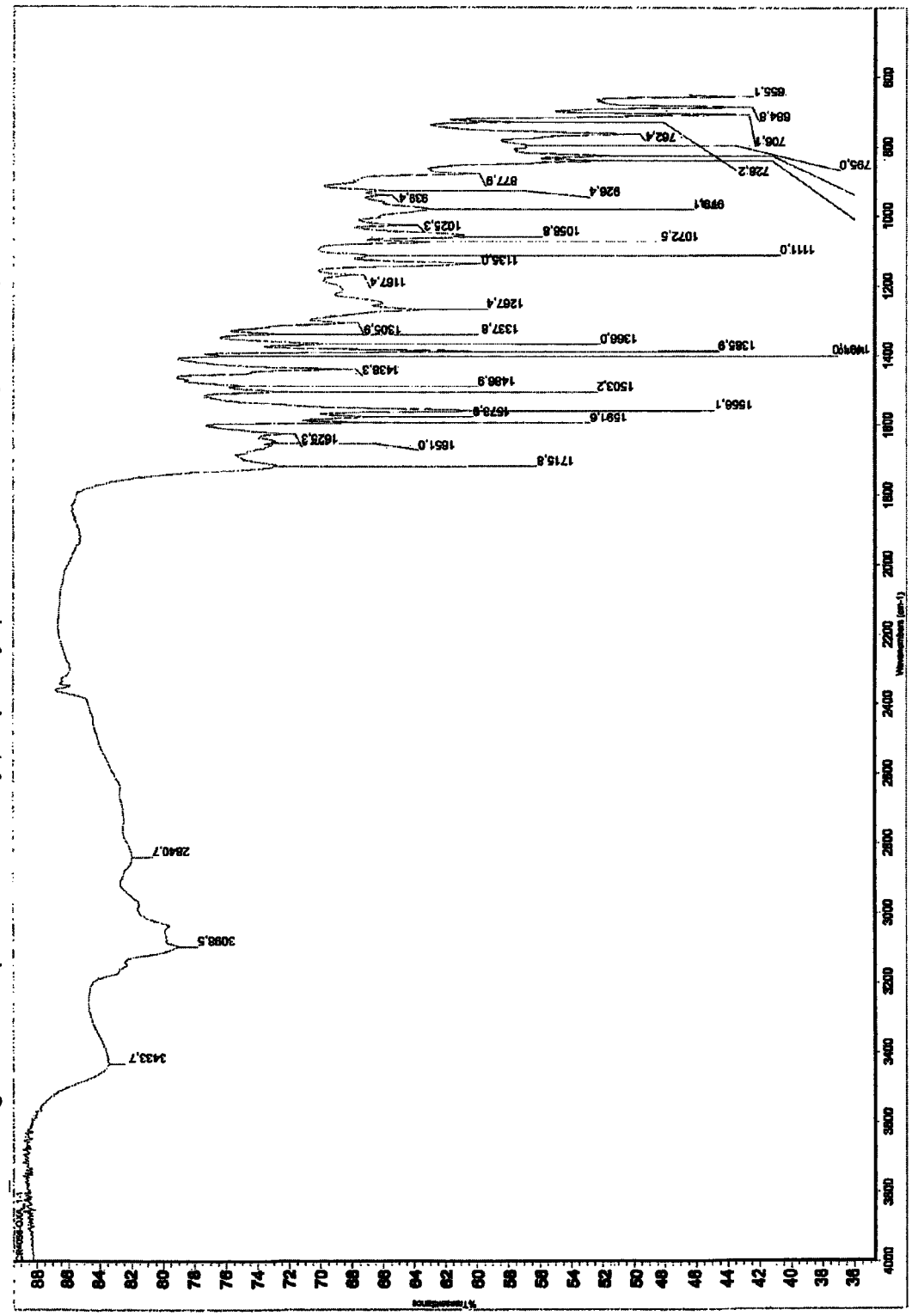
Figure 56: 6-(1H-imidazol-1-yl)-2-phenylquinazoline oxalate, Form A, FT-IR

CRYSTALLINE FORMS OF 6-(1H-IMIDAZOL-1-YL)-2-PHENYLQUINAZOLINE

CROSS-REFERENCE TO RELATED APPLICATIONS

This application is a National Phase Application of PCT International Application No. PCT/IB2010/052496, International Filing Date, 4 Jun. 2010, claiming priority to Italian Patent Application No. TO2009A000424, filed 4 Jun. 2009, both of which are hereby incorporated by reference in their entirety.

The present invention relates to novel crystalline forms of 6-(1H-imidazol-1-yl)-2-phenylquinazoline, CR4056, to pharmaceutically acceptable salts and solvates thereof, and also to methods for preparing it. 6-(1H-Imidazol-1-yl)-2-phenylquinazoline is a novel potent analgesic, anti-inflammatory and antidepressant agent. The present invention thus relates also to pharmaceutical formulations of crystalline forms of CR4056, respective salts and solvates thereof, their preparation and the use of these pharmaceutical forms in the therapy of chronic or acute pain, in the treatment of pathologies of inflammatory nature and in the treatment of depression.

INTRODUCTION

We have previously reported in patent application WO 2008/014 822 (Preparation of 6-(1H-imidazo)-quinazoline and -quinoline derivatives as analgesics and anti-inflammatory agents) a group of 6-(1H-imidazol-1-yl)-2-arylquinazoline derivatives with potent analgesic and anti-inflammatory activity, given that they are optimum pharmacological agents for treating inflammatory pathologies such as rheumatoid arthritis and osteoarthritis, pathologies of inflammatory nature of the respiratory tract, skin pathologies such as lupus erythematosus, eczema and psoriasis, and also inflammatory pathologies of the gastrointestinal tract such as ulcerative colitis, Crohn's disease and post-operative inflammatory complications.

In addition, by virtue of their highly analgesic action, these compounds may be used in the treatment of acute and chronic pain, such as post-operative and post-traumatic pain, muscular pain including fibromyalgia, neuropathic pain and cancer-related pain.

The preceding patent application PCT/EP 2008/057 908 of 20 Jun. 2008 (6-(1H-imidazo)-quinazoline and -quinoline derivatives, New MAO-A inhibitors and Imidazoline receptor ligands) described, for the same group of 6-(1H-imidazol-1-yl)-2-arylquinazoline derivatives, considerable antidepressant activity, which, when combined with the analgesic activity described above, gives these products an advantageous pharmacological profile, since depression is a non-negligible side effect in the chronic pathologies discussed above.

Among the 6-(1H-imidazol-1-yl)-2-arylquinazoline derivatives mentioned above, 6-(1H-imidazol-1-yl)-2-phenylquinazoline, CR4056, proves to be endowed with a considerable overall pharmacological profile.

The physicochemical characteristics of the solid state of pharmaceutical active principles (APIs) are of fundamental importance in the development of a drug product, since they may have an effect on the bioavailability, the stability and the processability both of the active principle and of the corresponding pharmaceutical forms.

It is known that in many cases this active principle may exist in the solid state in crystalline and amorphous forms and that, for the crystalline form, various solvates and polymorphs are possible.

Thus, polymorphism consists of the capacity of a substance to crystallize in more than one form, each form being characterized by a different arrangement of the molecules in the crystal lattice, while the capacity to give rise to solvates consists of the possibility of incorporating, in precise positions and according to a defined stoichiometry, water or solvent molecules into the crystal lattice.

Polymorphism is thus understood herein as described in ICH Q6A (International Conference on Harmonisation, Topic Q6A, May 2000), and thus the term "crystal form of an API" means herein a particular form of the solid state that is either a polymorph or solvate. Different polymorphs and solvates may have different solubilities, different stabilities, different hygroscopicities and different mechanical properties, for instance filterability and flowability.

Whereas the solubility characteristics may be important for the bioavailability of the drug product, the other physicochemical and mechanical characteristics are important in determining the stability and processability both of the active principle and of the pharmaceutical form, and may therefore have a considerable effect on the quality and cost of the product. Depending on the type of therapeutic use, the route of administration and also the formulation, it may be necessary to endow the same active principle with different physicochemical characteristics so as to afford it suitable adaptability to various formulation requirements.

Polymorphism may therefore be an advantageous opportunity for satisfying these requirements. For example, in the case of immediate-release oral formulations or of parenteral formulations, the solubility of the active principle may be fundamental for determining the efficacy of the treatment or even the possibility of using this administration route. 6-(1H-Imidazol-1-yl)-2-phenylquinazoline, CR4056, has shown a surprising capacity to crystallize as the free base in various crystalline forms, including solvates and polymorphs, which, if not adequately controlled, could interfere with the consistency of the physicochemical properties of the active principle, giving rise to the problems discussed above. In particular, crystallization of the product according to the methods reported in WO 2008/014 822 and in PCT/EP 2008/057 908 may give rise to mixtures of polymorphs and solvates.

The absorption of an orally administered drug product is determined by two fundamental factors, the permeability, that is to say the ability to diffuse across the gastrointestinal wall, and the solubility, that is to say its ability to dissolve in the gastrointestinal fluid.

To take these two factors into account, a classification of drug products was introduced, known as BCS (Biopharmaceutical Classification System) (G L Amidon et al., Pharm. Res. 1995, 12: 413-419). Since it is endowed with good permeability and low solubility, 6-(1H-imidazol-1-yl)-2-phenylquinazoline falls into class II (high permeability, low solubility) of the BCS system. For the drug products of this class, the solubility is fundamental in determining their absorption. The preparation of pharmaceutically acceptable salts generally represents a means for increasing the solubility of sparingly soluble products, and, in the case of products endowed with good permeability, is a suitable means for increasing their bioavailability.

However, it is not always possible to obtain salts endowed with suitable properties such as solubility, stability and processability. Since even the salts of organic compounds can give rise to polymorphs and solvates, it is occasionally possible to identify a suitable crystalline form of a salt or solvate having the said properties that would allow a suitable use for the preparation of pharmaceutical formulations that satisfy the need under consideration. For example, the stability of a crystalline form under the various storage conditions, which is necessary during the cycle of manufacture of the active principle and of the corresponding pharmaceutical formulation, is an essential condition for ensuring the quality, uniformity and consistency of the properties of the drug product.

In addition, during the manufacturing cycle, avoiding the use of particular known precautions by means of the hygroscopicity or low stability of the crystalline form can, in the majority of cases, considerably reduce the manufacturing costs. The stability of a crystalline form to mechanical stresses is important for all the processes normally used in the cycle of manufacture of a pharmaceutical specialty, for instance milling, which is necessary to obtain the appropriate particle size both for formulation (flowability) and dissolution requirements, mixing, which is necessary to ensure the uniformity of the active principle in the formulated product, and compression, which is necessary for the preparation of tablets.

The identification and characterization of a crystalline form may often be a non-trivial process (Giron Danielle, Monitoring polymorphism of drugs, an on-going challenge—part 2. American Pharmaceutical Review (2008), 11(3), 86-90). The use of numerous complementary analytical techniques, for instance X-ray diffraction, calorimetry and vibrational spectroscopy methods, makes it possible in the majority of cases to identify and characterize unambiguously a given crystalline form.

Thermogravimetric analysis (TGA), often combined with differential scanning calorimetry (DSC), is very useful for demonstrating the presence of hydrates or solvates. DSC is also a technique that is often essential for demonstrating polymorphs and the relating thermal properties. Among the vibrational spectroscopic techniques, infrared spectroscopy (FT-IR) is often capable of enabling the identification of polymorphs, and when this is not possible, Raman spectroscopy can furnish the desired information.

In the case of hydrates and for studying the hygroscopicity of a compound, DVS (Differential Vapour Sorption) is an important technique. The method of choice for the characterization of a crystalline form, whether it is a polymorph or a solvate, is, however, X-ray spectroscopy. This relatively simple technique, when it is a matter of powder diffraction experiments (XRPD), makes it possible unambiguously to identify a crystalline form and the relative degree of crystallinity in the majority of cases (Harry G. Brittain, X-ray powder diffraction of pharmaceutical materials, American Pharmaceutical Review 2002, 5(1), 74-76).

While XRPD can be used, after suitable calibration, for determining the purity of a polymorphic form with very high sensitivity (Stephen R. Byrn, Regulatory aspects of X-ray powder diffraction, American Pharmaceutical Review 2005, 8(3), 55-59), in its routine use during the process of identification and characterization of polymorphs, this technique is capable of detecting the presence of other crystalline forms with a sensitivity generally of the order of 5-10%.

The best way of identifying and characterizing a crystalline form is single-crystal X-ray diffraction spectroscopy (SC-XR). This makes it possible to identify the type and dimensions of the unit cell, characterizing the type of crystalline form, and is therefore the most suitable way for defining a polymorph or solvate and, as in the case of salts, for elucidating their stoichiometry unambiguously and for understanding their properties.

Despite the fact that considerable technological advances have been made, the major limitation of this technique still lies in the possibility of obtaining a crystal of the form to be analysed, of suitable dimensions and with a limited number of imperfections, this not always being easy or even possible.

BRIEF DESCRIPTION OF THE DRAWINGS

FIG. 1 shows a X-ray powder diffraction (XRPD) spectrum of crystalline 6-(1H-imidazol-1-yl)-2-phenylquinazoline ($C_{17}H_{12}N_4$) (Free Base Polymorph A);

FIG. 2 shows a differential scanning calorimetry (DSC) spectrum of crystalline 6-(1H-imidazol-1-yl)-2-phenylquinazoline (Free Base Polymorph A);

FIG. 3 shows a Fourier Transform Infrared (FT-IR) spectrum of crystalline 6-(1H-imidazol-1-yl)-2-phenylquinazoline (Free Base Polymorph A);

FIG. 4 shows a XRPD spectrum of crystalline 6-(1H-imidazol-1-yl)-2-phenylquinazoline (Free Base Polymorph D);

FIG. 5 shows a DSC spectrum of crystalline 6-(1H-imidazol-1-yl)-2-phenylquinazoline (Free Base Polymorph D);

FIG. 6 shows a FT-IR spectrum of crystalline 6-(1H-imidazol-1-yl)-2-phenylquinazoline (Free Base Polymorph D);

FIG. 7 shows a XRPD spectrum of crystalline 6-(1H-imidazol-1-yl)-2-phenylquinazoline (Free Base Polymorph E);

FIG. 8 shows a DSC spectrum of crystalline 6-(1H-imidazol-1-yl)-2-phenylquinazoline (Free Base Polymorph E);

FIG. 9 shows a FT-IR spectrum of crystalline 6-(1H-imidazol-1-yl)-2-phenylquinazoline (Free Base Polymorph E);

FIG. 10 shows a XRPD spectrum of crystalline 6-(1H-imidazol-1-yl)-2-phenylquinazoline (Free Base Polymorph B);

FIG. 11 shows a DSC spectrum of crystalline 6-(1H-imidazol-1-yl)-2-phenylquinazoline (Free Base Polymorph B);

FIG. 12 shows a FT-IR spectrum of crystalline 6-(1H-imidazol-1-yl)-2-phenylquinazoline (Free Base Polymorph B);

FIG. 13 shows a XRPD spectrum of crystalline 6-(1H-imidazol-1-yl)-2-phenylquinazoline (Free Base Polymorph C);

FIG. 14 shows a DSC spectrum of crystalline 6-(1H-imidazol-1-yl)-2-phenylquinazoline (Free Base Polymorph C);

FIG. 15 shows a FT-IR spectrum of crystalline 6-(1H-imidazol-1-yl)-2-phenylquinazoline (Free Base Polymorph C);

FIG. 16 compares the XRPD spectra of various crystalline forms for 6-(1H-imidazol-1-yl)-2-phenylquinazoline as a non-salified base;

FIG. 17 shows a XRPD spectrum of crystalline 6-(1H-imidazol-1-yl)-2-phenylquinazoline dihydrochloride monohydrate ($C_{17}H_{12}N_4.2HCl.H_2O$) (dihydrochloride salt form A);

FIG. 18 shows a DSC spectrum of crystalline 6-(1H-imidazol-1-yl)-2-phenylquinazoline dihydrochloride monohydrate (hydrochloride salt form A);

FIG. 19 shows a FT-IR spectrum of crystalline 6-(1H-imidazol-1-yl)-2-phenylquinazoline dihydrochloride monohydrate (hydrochloride salt form A);

FIG. 19b shows the thermal stability, using VT-XRPD, of crystalline 6-(1H-imidazol-1-yl)-2-phenylquinazoline dihydrochloride monohydrate (hydrochloride salt form A);

FIG. 19c shows the stability to moisture, using Differential Vapour Sorption (DVS), of crystalline 6-(1H-imidazol-1-yl)-2-phenylquinazoline dihydrochloride monohydrate (hydrochloride salt form A);

FIG. 20 shows a XRPD spectrum of crystalline 6-(1H-imidazol-1-yl)-2-phenylquinazoline hydrochloride ($C_{17}H_{12}N_4.HCl$) (hydrochloride salt form B);

FIG. 21 shows a XRPD spectrum of crystalline 6-(1H-imidazol-1-yl)-2-phenylquinazoline succinate (succinate salt form A);

FIG. 21a shows the three-dimensional crystal structure of 6-(1H-imidazol-1-yl)-2-phenylquinazoline succinate (succinate salt form A);

FIG. 21b compares the powder diffractogram calculated on the basis of the obtained structure (FIG. 21a) and the experimental XRPD (FIG. 21) for succinate salt form A;

FIG. 22 shows a DSC spectrum of crystalline 6-(1H-imidazol-1-yl)-2-phenylquinazoline succinate (succinate salt form A);

FIG. 23 shows a FT-IR spectrum of crystalline 6-(1H-imidazol-1-yl)-2-phenylquinazoline succinate (succinate salt form A);

FIG. 24 shows a XRPD spectrum of crystalline 6-(1H-imidazol-1-yl)-2-phenylquinazoline succinate ($C_{17}H_{12}N_4.C_4H_6O_4$) (succinate salt form B);

FIG. 25 shows a DSC spectrum of crystalline 6-(1H-imidazol-1-yl)-2-phenylquinazoline succinate (succinate salt form B);

FIG. 26 shows a FT-IR spectrum of crystalline 6-(1H-imidazol-1-yl)-2-phenylquinazoline succinate (succinate salt form B);

FIG. 27 shows a XRPD spectrum of crystalline 6-(1H-imidazol-1-yl)-2-phenylquinazoline succinate (succinate salt form C);

FIG. 28 shows a DSC spectrum of crystalline 6-(1H-imidazol-1-yl)-2-phenylquinazoline succinate (succinate salt form C);

FIG. 29 shows a FT-IR spectrum of crystalline 6-(1H-imidazol-1-yl)-2-phenylquinazoline succinate (succinate salt form C);

FIG. 30 shows the stability to moisture, using DVS, of crystalline 6-(1H-imidazol-1-yl)-2-phenylquinazoline succinate (succinate salt form A);

FIG. 31 shows a XRPD spectrum of crystalline 6-(1H-imidazol-1-yl)-2-phenylquinazoline (L)-tartrate dihydrate ($C_{17}H_{12}N_4.C_4H_6O_6.2H_2O$) (tartrate salt form A);

FIG. 32 shows a DSC spectrum of crystalline 6-(1H-imidazol-1-yl)-2-phenylquinazoline (L)-tartrate dihydrate (tartrate salt form A);

FIG. 33 shows a FT-IR spectrum of crystalline 6-(1H-imidazol-1-yl)-2-phenylquinazoline (L)-tartrate dihydrate (tartrate salt form A);

FIG. 34 shows the stability to moisture, using DVS, of crystalline 6-(1H-imidazol-1-yl)-2-phenylquinazoline (L)-tartrate dihydrate (tartrate salt form A);

FIG. 35 shows a XRPD spectrum of crystalline 6-(1H-imidazol-1-yl)-2-phenylquinazoline (L)-tartrate tetrahydrate ($C_{17}H_{12}N_4.C_4H_6O_6.4H_2O$) (tartrate salt form B);

FIG. 36 shows a DSC spectrum of crystalline 6-(1H-imidazol-1-yl)-2-phenylquinazoline (L)-tartrate tetrahydrate (tartrate salt form B);

FIG. 37 shows a FT-IR spectrum of crystalline 6-(1H-imidazol-1-yl)-2-phenylquinazoline (L)-tartrate tetrahydrate (tartrate salt form B);

FIG. 38 shows a XRPD spectrum of crystalline 6-(1H-imidazol-1-yl)-2-phenylquinazoline (L)-tartrate monohydrate ($C_{17}H_{12}N_4.C_4H_6O_6.H_2O$) (tartrate salt form C);

FIG. 39 shows a DSC spectrum of crystalline 6-(1H-imidazol-1-yl)-2-phenylquinazoline (L)-tartrate monohydrate (tartrate salt form C);

FIG. 40 shows a FT-IR spectrum of crystalline 6-(1H-imidazol-1-yl)-2-phenylquinazoline (L)-tartrate monohydrate (tartrate salt form C);

FIG. 41 shows a XRPD spectrum of crystalline 6-(1H-imidazol-1-yl)-2-phenylquinazoline (L)-tartrate dihydrate ($C_{17}H_{12}N_4.C_4H_6O_6$) (tartrate salt form D);

FIG. 42 shows a DSC spectrum of crystalline 6-(1H-imidazol-1-yl)-2-phenylquinazoline (L)-tartrate (tartrate salt form D);

FIG. 43 shows a FT-IR spectrum of crystalline 6-(1H-imidazol-1-yl)-2-phenylquinazoline (L)-tartrate (tartrate salt form D);

FIG. 44 shows a XRPD spectrum of crystalline 6-(1H-imidazol-1-yl)-2-phenylquinazoline fumarate ($C_{17}H_{12}N_4.0.5C_4H_4O_4$) (fumarate salt form A);

FIG. 44a shows the three-dimensional crystal structure of 6-(1H-imidazol-1-yl)-2-phenylquinazoline fumarate (fumarate salt form A);

FIG. 44b compares the powder diffractogram calculated on the basis of the obtained structure (FIG. 44a) and the experimental XRPD (FIG. 44) for fumarate salt form A;

FIG. 45 shows a DSC spectrum of crystalline 6-(1H-imidazol-1-yl)-2-phenylquinazoline fumarate (fumarate salt form A);

FIG. 46 shows a FT-IR spectrum of crystalline 6-(1H-imidazol-1-yl)-2-phenylquinazoline fumarate (fumarate salt form A);

FIG. 47 shows a XRPD spectrum of crystalline 6-(1H-imidazol-1-yl)-2-phenylquinazoline maleate ($C_{17}H_{12}N_4.C_4H_4O_4$) (maleate salt form A);

FIG. 47a shows the three-dimensional crystal structure of 6-(1H-imidazol-1-yl)-2-phenylquinazoline maleate (maleate salt form A);

FIG. 47b compares the powder diffractogram calculated on the basis of the obtained structure (FIG. 47a) and the experimental XRPD (FIG. 47) for maleate salt form A;

FIG. 48 shows a DSC spectrum of crystalline 6-(1H-imidazol-1-yl)-2-phenylquinazoline maleate (maleate salt form A);

FIG. 49 shows a FT-IR spectrum of crystalline 6-(1H-imidazol-1-yl)-2-phenylquinazoline maleate (maleate salt form A);

FIG. 50 shows a XRPD spectrum of crystalline 6-(1H-imidazol-1-yl)-2-phenylquinazoline maleate hemihydrate ($C_{17}H_{12}N_4.C_4H_4O_4.1/2H_2O$), (maleate salt form B);

FIG. 50a shows the stability to moisture, using DVS, of crystalline 6-(1H-imidazol-1-yl)-2-phenylquinazoline maleate (maleate salt form A);

FIG. 51a shows XRPD spectra of a mixture of the A and B forms of 6-(1H-imidazol-1-yl)-2-phenylquinazoline maleate obtained from isopropanol/water;

FIG. 51b shows a DSC spectrum of crystalline 6-(1H-imidazol-1-yl)-2-phenylquinazoline maleate hemihydrate (maleate salt form B);

FIG. 52 shows a FT-IR spectrum of crystalline 6-(1H-imidazol-1-yl)-2-phenylquinazoline maleate hemihydrate (maleate salt form B);

FIG. 53 shows a XRPD spectrum of crystalline 6-(1H-imidazol-1-yl)-2-phenylquinazoline phosphate ($C_{17}H_{12}N_4.H_2PO_4$) (phosphate salt form A);

FIG. 54 shows a XRPD spectrum of crystalline 6-(1H-imidazol-1-yl)-2-phenylquinazoline oxalate ($C_{17}H_{12}N_4.C_2H_2O_4$) (oxalate salt form A);

FIG. 55 shows a DSC spectrum of crystalline 6-(1H-imidazol-1-yl)-2-phenylquinazoline oxalate (oxalate salt form A); and FIG. 56 shows a FT-IR spectrum of crystalline 6-(1H-imidazol-1-yl)-2-phenylquinazoline oxalate (oxalate salt form A).

DESCRIPTION OF THE INVENTION

The present invention relates to the solid state of 6-(1H-imidazol-1-yl)-2-phenylquinazoline both as the free base and in the form of a stable and pharmaceutically acceptable salt. By the appropriate use of the various crystalline forms of the free base and of its salts as described herein, it is possible not only to ensure consistency of the physicochemical properties of the active principle, but also to enable its administration in various forms such as oral and parenteral forms.

In particular, the present invention relates to the solid state of the active principle 6-(1H-imidazol-1-yl)-2-phenylquinazoline (I), CR4056, and more particularly the crystalline forms of the free base, and pharmaceutically acceptable salts and solvates thereof, and also to the method for preparing these polymorphs, salts and solvates, and to the use of the said polymorphs and solvates of the free base or of the salts or corresponding solvates thereof for the preparation of pharmaceutical formulations. The invention also relates to the use of the said pharmaceutical formulations for the pharmacological treatment of pain and of the pathologies of inflammatory nature discussed previously by this compound.

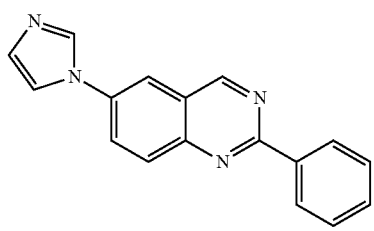 [SMILES: c1ccc(-c2ncc3cc(-n4ccnc4)ccc3n2)cc1]

(I)

In particular, one aspect of the present invention relates to polymorphs of 6-(1H-imidazol-1-yl)-2-phenylquinazoline, as the non-salified base, and in non-solvated form.

More particularly, this aspect includes substantially pure polymorphic crystalline forms of 6-(1H-imidazol-1-yl)-2-phenylquinazoline, which may be prepared reproducibly and which are endowed with bioavailability, stability and hygroscopicity characteristics and mechanical properties, so as to be able to be used for the preparation of suitable pharmaceutical formulations, which can satisfy the regulations in force in terms of quality (ICH Q10, Pharmaceutical Quality System, June 2008).

The expression "substantially pure crystalline form" means here and in the following text a crystalline form characterized by XRPD, which contains at most only traces of the signals relating to other crystalline forms. Preferably, the presence of such signals is less than or equal to the detectability limit of the system (XRPD) and therefore, in the majority of the cases described herein, the term "substantially pure form" means a crystalline form with a purity of not less than 90%.

Crystalline form of 6-(1H-imidazol-1-yl)-2-phenylquinazoline ($C_{17}H_{12}N_4$) (Free Base Polymorph A), characterized by the X-ray powder diffraction (XRPD) spectrum given in FIG. 1, and comprising the main peaks given in Table 1.

The term "main peaks" means here and in the following text those with a relative intensity>5%. The XRPD diffractogram described herein was obtained by irradiation with Cu Kα and using XPERT-PRO for the data processing.

More particularly, the powder diffraction spectra given herein were acquired using an X'Pert PRO diffractometer (PANalytical) and using the following parameters for the data acquisition and processing:

Anode: Cu (type: ceramic diffraction X-ray tube, Long Line Focus, PW3373/00 Cu LFF)
Focus dimension: 12 mm×0.4 mm
Focus quality: to COCIR spec.
Be window diameter: 14 mm, Be window thickness: 300 μm
Generator setting: 40 mA, 40 KV
Wavelength: Kα1=1.54060 Å
  Kα2=1.54443 Å
  Kβ=1.39225 Å
  Kα1/Kα2 ratio: 0.50000
Kα=1.541874 Å
Kβ=1.392250 Å
Incident beam path Radius (mm): 240.0
PW3050/60 X'Pert PRO Standard Resolution Goniometer
Goniometer radius: 240.00 mm (X'Pert PRO MPD systems)
Dist. Focus-diverg. Slit: 91.00 mm
Spinning: 1°/sec
Start position: 2θ°=3.0084
End position: 2θ°=39.9834
Step Size: 2θ°=0.0170
Scan step time (s): 12.9218
Scan Type: continuous
PSD Mode: Scanning
PSD length: 2θ°=2.12
Offset: 2θ°=0.000
Divergence slit size: 0.2393°
Specimen Length: 10.00 mm
face-diffraction plane 150 mm
Filter: Nickel (0.020 mm)
Detector Name: X'Celerator
Type: RTMS detector
PHD—Lower level (%): 39.5
PHD—Upper level (%): 80.0
Mode: Scanning
Active length)(°): 2.122

All the other diffractograms described in the present invention were obtained in the same manner.

TABLE 1

| Diffraction angle (2θ°) | Relative intensity (%) |
|---|---|
| 10.02 | 29.8 |
| 10.21 | 35.0 |
| 11.48 | 14.4 |
| 15.40 | 100 |
| 16.65 | 37.3 |
| 20.07 | 8.53 |
| 21.48 | 31.7 |
| 21.58 | 33.9 |
| 22.06 | 18.38 |
| 23.27 | 5.74 |
| 24.62 | 75.62 |
| 26.78 | 24.29 |
| 29.20 | 24.36 |
| 29.84 | 6.61 |

This crystalline form of 6-(1H-imidazol-1-yl)-2-phenylquinazoline, (Free base Polymorph A), is also characterized by the differential scanning calorimetry (DSC) given in FIG. 2, which shows an endothermic event corresponding to melting with an onset at about 180° C.

All the DSC spectra reported herein were acquired at a scanning rate of 10°/min.

This crystalline form of 6-(1H-imidazol-1-yl)-2-phenylquinazoline, (Free base Polymorph A), is also characterized by the FT-IR spectrum (ATR), (FT-IR/ATR: Fourier Transform Infrared Spectroscopy in the attenuated total reflection mode) given in FIG. 3, which shows characteristic absorptions at 3086, 1587, 1155, 1169, 1185, 851 and 836 $cm^{-1}$.

The crystalline form of 6-(1H-imidazol-1-yl)-2-phenylquinazoline ($C_{17}H_{12}N_4$), (Free base Polymorph A), is the thermodynamically more stable form of this product; this is obvious by comparison of the DSC spectra of form A, FIG. 2, with those of the corresponding polymorphs D and E, with respect to FIGS. 5 and 8. It is noted that form A is characterized by a higher melting point (about 180° C.) while the other two forms melt at lower temperatures (at about 160 and about 162° C., respectively); in addition, from the DSC spectra, it is noted both that the heat of fusion of the other forms are lower than that of form A, and that both the forms D and E recrystallize into form A. The greater stability of form A relative to forms D and E is also evidenced by the experiments reported in Examples 21 and 26. In addition, the experiment in Example 3 clearly shows that it is possible to transform a mixture of forms into the more stable form A.

In the development of an oral drug product, the choice of the appropriate crystalline form is usually fundamental for optimizing both the efficacy and processability properties of the active principle.

Form A, although not characterized by optimum solubility at neutral pH, shows acceptable solubility at the gastric pH (Example 7) and acceptable bioavailability (Example 8). Since polymorph A is the thermodynamically more stable one, it is endowed with greater stability both chemically and with regard to conversion into other forms. In addition, this polymorph is particularly stable with respect to mechanical stresses (Example 6), not giving rise to conversion into other forms or to the formation of amorphous material, which often impairs the flowability and hygroscopicity properties of the product, which are harmful during the formulation process. Thus, form A is particularly indicated for preparations of pharmaceutical formulations of 6-(1H-imidazol-1-yl)-2-phenylquinazoline such as immediate-release tablets and capsules.

In the development of an oral drug product, it is absolutely essential that the active principle be administered in a definite and consistent crystalline form (ICH, Q6A: Test Procedures and Acceptance Criteria for New Drug substances and New Drug products, May 2000) so as to ensure consistency of bioavailability, of the physicochemical and mechanical properties such as flowability and density, and also the stability of the active principle in order consequently to ensure the properties of the drug product.

6-(1H-Imidazol-1-yl)-2-phenylquinazoline has shown a surprising propensity to crystallize as mixtures of polymorphic and hydrate forms when the crystallization process is not performed according to appropriate and defined procedures, thus giving rise to an active principle characterized by properties that differ as a function of the composition of polymorphs and hydrates. This is in contrast with that discussed hereinabove and may lead to considerable problems of processability and consistency in the preparation of the drug product.

The crystallization of 6-(1H-imidazol-1-yl)-2-phenylquinazoline as described in Examples 1, 2 and 3 makes it possible to obtain form A in high purity and consistently. In addition, on account of its thermal stability, the process for drying this product requires minor precautions and is therefore easier and less expensive than those of the other described forms.

Crystalline form of 6-(1H-imidazol-1-yl)-2-phenylquinazoline ($C_{17}H_{12}N_4$) (Free base Polymorph D), characterized by the XRPD spectrum given in FIG. 4 and comprising the main peaks given in Table 2.

TABLE 2

| Diffraction angle (2θ°) | Relative intensity (%) |
|---|---|
| 4.18 | 5.0 |
| 5.41 | 37.14 |
| 8.25 | 6.13 |
| 10.83 | 60.0 |
| 14.15 | 7.12 |
| 16.01 | 12.20 |
| 16.44 | 84.42 |
| 16.54 | 100 |
| 16.98 | 30.11 |
| 20.39 | 80.43 |
| 23.24 | 40.81 |
| 25.01 | 30.0 |
| 26.40 | 78.64 |
| 30.26 | 16.87 |

This crystalline form of 6-(1H-imidazol-1-yl)-2-phenylquinazoline (Free base Polymorph D), is also characterized by the DSC spectrum given in FIG. 5, which shows an endothermic event corresponding to melting with an onset at about 160° C., an exothermic event corresponding to the crystallization of form A, an endothermic event corresponding to the melting of form A, with onset at about 180° C.

This crystalline form of 6-(1H-imidazol-1-yl)-2-phenylquinazoline (Free base Polymorph D), is also characterized by the FT-IR spectrum (ATR) given in FIG. 6, which shows characteristic absorptions at 3096, 1579, 1586, 1556 and 1247 $cm^{-1}$.

The crystalline form A does not show good solubility at a pH that is not strongly acidic. In certain cases, it is necessary for the absorption of the drug product to take place in the intestinal tract where the pH is neutral or basic. Enteric formulations are often used to do this. In some cases, the solubility of a sparingly soluble active principle may be increased by amorphization of the active principle and dispersion of the amorphous product in suitable excipients that do not increase the wettability and which have a dispersing and disintegrating action. Processes in which this amorphization takes place by milling the active principle with the excipients are particularly advantageous. Considering its stability characteristics, the polymorphic form D is, among the 6-(1H-imidazol-1-yl)-2-phenylquinazoline forms, the one which lends itself best to this type of use.

Crystalline form of 6-(1H-imidazol-1-yl)-2-phenylquinazoline ($C_{17}H_{12}N_4$), (Free base Polymorph E), characterized by the XRPD spectrum given in FIG. 7 and comprising the main peaks given in Table 3.

TABLE 3

| Diffraction angle (2θ°) | Relative intensity (%) |
|---|---|
| 4.18 | 12.87 |
| 8.28 | 59.59 |
| 10.97 | 13.69 |
| 11.90 | 15.24 |
| 13.11 | 11.49 |
| 14.50 | 91.14 |

TABLE 3-continued

| Diffraction angle (2θ°) | Relative intensity (%) |
|---|---|
| 16.04 | 100 |
| 17.69 | 43.42 |
| 19.42 | 20.59 |
| 20.77 | 38.83 |
| 22.84 | 7.75 |
| 23.87 | 9.03 |
| 24.92 | 5.94 |

This crystalline form of 6-(1H-imidazol-1-yl)-2-phenylquinazoline (Free base Polymorph E), is also characterized by the DSC spectrum given in FIG. 8, which shows an endothermic event corresponding to melting with an onset at about 162° C., an exothermic event corresponding to the crystallization of form A, and an endothermic event corresponding to the melting of form A, with onset at about 181° C.

This crystalline form of 6-(1H-imidazol-1-yl)-2-phenylquinazoline (Free base Polymorph E), is also characterized by the FT-IR spectrum (ATR) given in FIG. 9, which shows characteristic absorptions at 3122, 1577, 1338, 1174, 1146, 1071 and 1057 cm$^{-1}$.

The crystalline form A does not show good solubility at a pH that is not strongly acidic. In certain cases, it is necessary for the absorption of the drug product to take place in the intestinal tract where the pH is neutral or basic. The crystalline form E at non-acidic pH is endowed with solubility that is twice that of form A, is more stable than form D, and is therefore the best candidate for pharmaceutical formulations of 6-(1H-imidazol-1-yl)-2-phenylquinazoline in enteric capsules.

In addition, form E, on account of its lower crystallinity and plasticity, may be used in the preparation of slow-release pharmaceutical formulations and, as described for form D, in the preparation of pharmaceutical forms in which amorphization of the active principle and dispersion of the amorphous product are obtained by milling with excipients.

Polymorph E may be consistently obtained in high yields according to the method given in Example 25.

In another aspect thereof, the present invention relates to polymorphs of 6-(1H-imidazol-1-yl)-2-phenylquinazoline, as non-salified base, and in solvated form. More particularly, this aspect comprises substantially pure polymorphic crystalline forms of 6-(1H-imidazol-1-yl)-2-phenylquinazoline hydrate, which may be prepared in a reproducible manner and which are endowed with bioavailability, stability and hygroscopicity characteristics and mechanical properties, such that they can be used for the preparation of suitable pharmaceutical formulations as discussed hereinabove.

Crystalline form of 6-(1H-imidazol-1-yl)-2-phenylquinazoline monohydrate ($C_{17}H_{12}N_4 \cdot H_2O$) (free base form B), characterized by the XRPD spectrum given in FIG. 10 and comprising the main peaks given in Table 4.

TABLE 4

| Diffraction angle (2θ°) | Relative intensity (%) |
|---|---|
| 6.01 | 100 |
| 6.10 | 88.93 |
| 11.84 | 24.41 |
| 14.54 | 9.53 |
| 17.31 | 12.74 |
| 19.17 | 22.68 |

TABLE 4-continued

| Diffraction angle (2θ°) | Relative intensity (%) |
|---|---|
| 21.46 | 11.95 |
| 25.84 | 14.22 |
| 26.89 | 7.36 |
| 27.89 | 7.89 |

This crystalline form of 6-(1H-imidazol-1-yl)-2-phenylquinazoline monohydrate (free base form B), is also characterized by the DSC spectrum given in FIG. 11, which shows an endothermic event corresponding to desolvatation in the range from about 40-100° C., an endothermic event corresponding to melting with an onset at about 156° C., an exothermic event corresponding to the crystallization of form A, and an endothermic event corresponding to the melting of form A, with onset at about 178° C.

This crystalline form of 6-(1H-imidazol-1-yl)-2-phenylquinazoline monohydrate (free base form B), is also characterized by the FT-IR spectrum (ATR) given in FIG. 12, which shows characteristic absorptions at 1327, 1310, 1174, 1146, 1103, 901 and 878 cm$^{-1}$.

Crystalline form of 6-(1H-imidazol-1-yl)-2-phenylquinazoline monohydrate ($C_{17}H_{12}N_4 \cdot H_2O$) (free base form C), characterized by the XRPD spectrum given in FIG. 13 and comprising the main peaks given in Table 5.

TABLE 5

| Diffraction angle (2θ°) | Relative intensity (%) |
|---|---|
| 7.75 | 100 |
| 11.87 | 19.4 |
| 14.21 | 25.46 |
| 17.14 | 32.23 |
| 19.24 | 12.77 |
| 20.08 | 6.48 |
| 25.23 | 10.71 |
| 25.68 | 26.06 |
| 27.61 | 8.24 |

This crystalline form of 6-(1H-imidazol-1-yl)-2-phenylquinazoline monohydrate (free base form C), is also characterized by the DSC spectrum given in FIG. 14, which shows an endothermic event corresponding to desolvatation in the range from about 30-80° C., an endothermic event corresponding to melting with an onset at about 163° C., an exothermic event corresponding to the crystallization of form A, and an endothermic event corresponding to the melting of form A, with onset at about 179° C.

This crystalline form of 6-(1H-imidazol-1-yl)-2-phenylquinazoline monohydrate (free base form C), is also characterized by the FT-IR spectrum (ATR) given in FIG. 15, which shows characteristic absorptions at 1566, 1520, 1323, 1175, 1146 and 1110 cm$^{-1}$.

While it is usually preferred not to develop hydrated forms of active principles for stability reasons, in the case of 6-(1H-imidazol-1-yl)-2-phenylquinazoline, the hydrated forms and in particular form C have shown surprising stability under ambient conditions and may be prepared in optimum yields and impurities according to the methods given, respectively, in Examples 10 to 14.

Although characterized by solubilities similar to those of the polymorphs of 6-(1H-imidazol-1-yl)-2-phenylquinazoline, the wettability of the hydrated forms is greater than that of the polymorphs, and these hydrated forms are therefore useful in the preparation of pharmaceutical formulations that do not involve the use of excipients liable to increase the wettability of the active principle. In addition, since the treatment of the polymorphs of 6-(1H-imidazol-1-yl)-2-phenylquinazoline with water gives rise to these hydrated forms, they are useful in all pharmaceutical processes involving the use of water either in the granulation process or in other operations.

The XRPD spectra of the various crystalline forms reported for 6-(1H-imidazol-1-yl)-2-phenylquinazoline, including polymorphs and hydrates and relating to the non-salified base, are compared in FIG. 16. It is gathered that, even in this case, the XRPD method is sufficient per se to identify these forms, since they are always the most intense peaks and are well separated in the various forms, which is also a guarantee of suitable purity, as may be found from the XRPD spectra of the individual forms.

Another aspect of the present invention relates to the crystalline forms, in anhydrous or solvated form, of 6-(1H-imidazol-1-yl)-2-phenylquinazoline, which may be obtained by salification with organic or mineral acids. More particularly, this aspect includes substantially pure crystalline forms of salts of 6-(1H-imidazol-1-yl)-2-phenylquinazoline, which may be prepared in a reproducible manner and which are endowed with consistent bioavailability, stability and hygroscopicity characteristics and mechanical properties, such that they can be used for the preparation of suitable pharmaceutical formulations as discussed hereinabove.

Crystalline form of 6-(1H-imidazol-1-yl)-2-phenylquinazoline dihydrochloride monohydrate ($C_{17}H_{12}N_4 \cdot 2HCl \cdot H_2O$) (dihydrochloride salt form A), characterized by the XRPD spectrum given in FIG. 17 and comprising the main peaks given in Table 6.

TABLE 6

| Diffraction angle (2θ°) | Relative intensity (%) |
| --- | --- |
| 6.63 | 100 |
| 11.31 | 25.0 |
| 12.55 | 11.0 |
| 14.37 | 55.4 |
| 16.88 | 5.9 |
| 19.29 | 28.13 |
| 19.73 | 18.32 |
| 23.09 | 85.31 |
| 23.82 | 11.59 |
| 25.02 | 56.61 |
| 26.34 | 76.96 |
| 26.81 | 93.83 |
| 27.65 | 15.34 |
| 28.55 | 12.13 |
| 29.88 | 19.0 |
| 30.80 | 13.35 |
| 31.44 | 15.87 |
| 33.0 | 19.98 |
| 34.12 | 7.54 |
| 37.8 | 7.78 |

This crystalline form of 6-(1H-imidazol-1-yl)-2-phenylquinazoline dihydrochloride monohydrate (hydrochloride salt form A), is also characterized by the DSC spectrum given in FIG. 18, which shows an endothermic event with onset at about 144° C. and a second endothermic event with onset at about 226° C.

This crystalline form of 6-(1H-imidazol-1-yl)-2-phenylquinazoline dihydrochloride monohydrate, (hydrochloride salt form A), is also characterized by the FT-IR spectrum (ATR) given in FIG. 19.

Solubility is a fundamental factor in determining the absorption of a drug product endowed with good permeability such as 6-(1H-imidazol-1-yl)-2-phenylquinazoline. Despite the fact that the base has demonstrated acceptable bioavailability, the sparing solubility gives rise to a good margin for increasing its bioavailability. In general, the formation of salts is used for this purpose, but often the salts of weak bases such as 6-(1H-imidazol-1-yl)-2-phenylquinazoline are unstable, hygroscopic and have poor mechanical properties. Unlike the monohydrochloride, which is thus found to be hygroscopic, giving rise to isolation problems, 6-(1H-imidazol-1-yl)-2-phenylquinazoline dihydrochloride monohydrate proves to be non-hygroscopic (Example 32), thermally stable under suitable storage and drying conditions (Example 30), stable with respect to mechanical stresses (Example 31) and highly soluble and bioavailable (Examples 33 and 34).

This salt is therefore suitable for the preparation of immediate-release pharmaceutical formulations in the form of tablets and capsules. In addition, this salt is suitable for pharmaceutical formulations of the active principle such as syrups and parenteral formulations in which it is necessary to ensure high solubility of the active principle.

Crystalline form of 6-(1H-imidazol-1-yl)-2-phenylquinazoline hydrochloride ($C_{17}H_{12}N_4 \cdot HCl$) (hydrochloride salt form B), characterized by the XRPD spectrum given in FIG. 20 and comprising the main peaks given in Table 7.

TABLE 7

| Diffraction angle (2θ°) | Relative intensity (%) |
| --- | --- |
| 4.72 | 16.90 |
| 9.36 | 17.64 |
| 10.37 | 45.43 |
| 14.69 | 100 |
| 18.34 | 9.33 |
| 20.76 | 30.54 |
| 21.87 | 7.18 |

This crystalline form of 6-(1H-imidazol-1-yl)-2-phenylquinazoline monohydrochloride (hydrochloride salt form B), is also characterized by melting with decomposition at about 240° C.

Crystalline form of 6-(1H-imidazol-1-yl)-2-phenylquinazoline succinate ($C_{17}H_{12}N_4 \cdot 0.5C_4H_6O_4$) (succinate salt form A), characterized by a monoclinic system with cell parameters a=8.0152 (6) Å, b=5.9038 (4) Å, c=33.127 (3) Å, α: 90°, β=93.280° (8), γ=90°, V=1565.0 (2) Å$^3$, space group P2$_1$/c, with the XRPD spectrum given in FIG. 21 and comprising the main peaks given in Table 8. The three-dimensional structure of this crystalline form obtained via SC-XR is given in FIG. 21a, and the comparison between the powder diffractogram calculated on the basis of the obtained structure and the experimental XRPD is given in FIG. 21b.

TABLE 8

| Diffraction angle (2θ°) | Relative intensity (%) |
| --- | --- |
| 5.47 | 17.06 |
| 10.83 | 20.3 |
| 11.07 | 6.73 |
| 15.89 | 100 |
| 20.12 | 6.75 |
| 22.03 | 20.57 |
| 24.39 | 26.52 |

TABLE 8-continued

| Diffraction angle (2θ°) | Relative intensity (%) |
|---|---|
| 26.20 | 22.82 |
| 27.25 | 11.97 |
| 27.79 | 9.62 |
| 28.22 | 9.24 |
| 32.39 | 5.0 |

This crystalline form of 6-(1H-imidazol-1-yl)-2-phenylquinazoline succinate (succinate salt form A), is also characterized by the DSC spectrum given in FIG. 22, which shows an endothermic event, with onset at about 150° C., and a second endothermic event corresponding to melting, with onset at about 183° C.

This crystalline form of 6-(1H-imidazol-1-yl)-2-phenylquinazoline succinate, (succinate salt form A) is also characterized by the FT-IR spectrum (ATR) given in FIG. 23.

Crystalline form of 6-(1H-imidazol-1-yl)-2-phenylquinazoline succinate ($C_{17}H_{12}N_4 \cdot C_4H_6O_4$) (succinate salt form B), characterized by the XRPD spectrum given in FIG. 24 and comprising the main peaks given in Table 9.

TABLE 9

| Diffraction angle (2θ°) | Relative intensity (%) |
|---|---|
| 5.05 | 51.45 |
| 5.23 | 75.59 |
| 10.10 | 34.36 |
| 10.26 | 45.36 |
| 11.26 | 7.86 |
| 17.10 | 100 |
| 17.61 | 8.31 |
| 22.03 | 22.41 |
| 24.27 | 16.46 |
| 24.94 | 6.81 |
| 25.66 | 20.75 |
| 27.20 | 7.83 |
| 28.36 | 8.22 |

This crystalline form of 6-(1H-imidazol-1-yl)-2-phenylquinazoline succinate (succinate salt form B), is also characterized by the DSC spectrum given in FIG. 25, which shows an endothermic event, with onset at about 108° C., and a second endothermic event corresponding to melting with an onset at about 181° C.

This crystalline form of 6-(1H-imidazol-1-yl)-2-phenylquinazoline succinate, (succinate salt form B), is also characterized by the FT-IR spectrum (ATR) given in FIG. 26.

Crystalline form of 6-(1H-imidazol-1-yl)-2-phenylquinazoline succinate, (succinate salt form C), characterized by the XRPD spectrum given in FIG. 27 and comprising the main peaks given in Table 10.

TABLE 10

| Diffraction angle (2θ°) | Relative intensity (%) |
|---|---|
| 5.15 | 100 |
| 5.24 | 60.74 |
| 10.27 | 64.65 |
| 11.17 | 12.39 |
| 16.57 | 69.02 |
| 22.06 | 34.94 |
| 25.06 | 50.72 |

TABLE 10-continued

| Diffraction angle (2θ°) | Relative intensity (%) |
|---|---|
| 25.55 | 21.68 |
| 27.11 | 9.09 |

This crystalline form of 6-(1H-imidazol-1-yl)-2-phenylquinazoline succinate (succinate salt form C), is also characterized by the DSC spectrum given in FIG. 28, which shows an endothermic event, with onset at about 119° C., and a second endothermic event corresponding to melting with an onset at about 184° C.

This crystalline form of 6-(1H-imidazol-1-yl)-2-phenylquinazoline succinate, (succinate salt form C), is also characterized by the FT-IR spectrum (ATR) given in FIG. 29.

Although the salt 6-(1H-imidazol-1-yl)-2-phenylquinazoline succinate, in particular form A, is not excessively soluble, it is more soluble than the corresponding base, and is also characterized by good mechanical stability due to the absence of hygroscopicity even under more drastic conditions. This salt in its crystalline form A is therefore useful in the preparation of pharmaceutical formulations involving particular mechanical stresses or excessive exposure to moisture.

Crystalline form of 6-(1H-imidazol-1-yl)-2-phenylquinazoline (L)-tartrate dihydrate ($C_{17}H_{12}N_4 \cdot C_4H_6O_6 \cdot 2H_2O$) (tartrate salt form A), characterized by the XRPD spectrum given in FIG. 31 and comprising the main peaks given in Table 11.

TABLE 11

| Diffraction angle (2θ°) | Relative intensity (%) |
|---|---|
| 3.53 | 46.04 |
| 6.94 | 12.81 |
| 7.25 | 11.60 |
| 9.81 | 9.39 |
| 10.52 | 13.32 |
| 14.97 | 17.18 |
| 15.94 | 19.56 |
| 16.63 | 100 |
| 19.59 | 31.14 |
| 20.39 | 30.03 |
| 21.02 | 18.00 |
| 23.19 | 9.05 |
| 24.92 | 17.28 |
| 25.54 | 33.40 |
| 26.37 | 33.21 |

This crystalline form of 6-(1H-imidazol-1-yl)-2-phenylquinazoline (L)-tartrate dihydrate (tartrate salt form A), is also characterized by the DSC spectrum given in FIG. 32, which shows an endothermic event in the range from about 60-95° C., an exothermic event corresponding to crystallization with onset at about 103° C. and a second endothermic event corresponding to melting with decomposition, with onset at about 190° C.

This crystalline form of 6-(1H-imidazol-1-yl)-2-phenylquinazoline (L)-tartrate dihydrate (tartrate salt form A), is also characterized by the FT-IR spectrum (ATR) given in FIG. 33.

Crystalline form of 6-(1H-imidazol-1-yl)-2-phenylquinazoline (L)-tartrate tetrahydrate ($C_{17}H_{12}N_4 \cdot C_4H_6O_6 \cdot 4H_2O$) (tartrate salt form B), characterized by the XRPD spectrum given in FIG. 35 and comprising the main peaks given in Table 12.

TABLE 12

| Diffraction angle (2θ°) | Relative intensity (%) |
| --- | --- |
| 3.57 | 36.66 |
| 6.93 | 14.67 |
| 10.52 | 12.01 |
| 12.57 | 5.88 |
| 14.08 | 6.93 |
| 16.62 | 100 |
| 20.43 | 27.21 |
| 20.74 | 16.80 |
| 23.92 | 7.62 |
| 24.96 | 18.25 |
| 25.53 | 30.53 |
| 26.36 | 33.88 |
| 28.10 | 10.48 |

This crystalline form of 6-(1H-imidazol-1-yl)-2-phenylquinazoline (L)-tartrate tetrahydrate (tartrate salt form B), is also characterized by the DSC spectrum given in FIG. 36, which shows an endothermic event in the range from about 36-100° C., with loss of four molecules of $H_2O$, an exothermic event corresponding to crystallization with a peak at about 114° C., and a second endothermic event corresponding to melting with decomposition, with onset at about 187° C.

This crystalline form of 6-(1H-imidazol-1-yl)-2-phenylquinazoline (L)-tartrate tetrahydrate (tartrate salt form B), is also characterized by the FT-IR spectrum (ATR) given in FIG. 37.

Crystalline form of 6-(1H-imidazol-1-yl)-2-phenylquinazoline (L)-tartrate monohydrate ($C_{17}H_{12}N_4 \cdot C_4H_6O_6 \cdot H_2O$) (tartrate salt form C), characterized by the XRPD spectrum given in FIG. 38 and comprising the main peaks given in Table 13.

TABLE 13

| Diffraction angle (2θ°) | Relative intensity (%) |
| --- | --- |
| 3.12 | 45.38 |
| 7.24 | 12.72 |
| 10.01 | 6.12 |
| 11.21 | 11.48 |
| 16.28 | 9.33 |
| 17.40 | 100 |
| 18.65 | 12.30 |
| 19.33 | 11.20 |
| 21.13 | 29.16 |
| 23.83 | 9.62 |
| 25.0 | 10.40 |
| 26.61 | 24.54 |
| 27.08 | 25.70 |

This crystalline form of 6-(1H-imidazol-1-yl)-2-phenylquinazoline (L)-tartrate monohydrate (tartrate salt form C), is also characterized by the DSC spectrum given in FIG. 39, which shows an endothermic event with onset at about 42° C., an exothermic event at about 130° C., and a second endothermic event with onset at about 180° C.

This crystalline form of 6-(1H-imidazol-1-yl)-2-phenylquinazoline (L)-tartrate monohydrate (tartrate salt form C), is also characterized by the FT-IR spectrum (ATR) given in FIG. 40.

Crystalline form of 6-(1H-imidazol-1-yl)-2-phenylquinazoline (L)-tartrate ($C_{17}H_{12}N_4 \cdot C_4H_6O_6$) (tartrate salt form D), characterized by the XRPD spectrum given in FIG. 41 and comprising the main peaks given in Table 14.

TABLE 14

| Diffraction angle (2θ°) | Relative intensity (%) |
| --- | --- |
| 9.60 | 32.56 |
| 9.98 | 54.23 |
| 11.47 | 9.46 |
| 12.44 | 13.89 |
| 17.37 | 33.24 |
| 18.75 | 50.07 |
| 18.99 | 33.90 |
| 19.21 | 100 |
| 19.56 | 30.16 |

This crystalline form of 6-(1H-imidazol-1-yl)-2-phenylquinazoline (L)-tartrate, form D, is also characterized by the DSC spectrum given in FIG. 42, which shows an endothermic event corresponding to melting with decomposition, with onset at about 189° C.

This crystalline form of 6-(1H-imidazol-1-yl)-2-phenylquinazoline (L)-tartrate, form D, is also characterized by the FT-IR spectrum (ATR) given in FIG. 43.

The salt of 6-(1H-imidazol-1-yl)-2-phenylquinazoline tartrate monohydrate (form A) is not hygroscopic (Example 45), is stable with respect to mechanical stresses (Example 44), and has good solubility (Example 46) and optimum bioavailability (Example 47). Not only can this salt be used for oral formulations such as capsules and tables, since it has suitable solubility, stability and processability characteristics, but, on account of its good solubility, it may also be used in parenteral formulations since the pH of its solutions, even highly concentrated solutions, is much more physiologically compatible than that of the corresponding hydrochloride or dihydrochloride.

Crystalline form of 6-(1H-imidazol-1-yl)-2-phenylquinazoline fumarate ($C_{17}H_{12}N_4 \cdot 0.5 C_4H_4O_4$) (fumarate salt form A), characterized by a monoclinic system with cell parameters a=10.7980 (8) Å, b=11.6643 (7) Å, c=13.0888 (11) Å, α: 90°, β=106.842° (8), γ=90°, V=1577.8 (2) Å$^3$, space group P21/c, with the XRPD spectrum given in FIG. 44 and comprising the main peaks given in Table 15.

TABLE 15

| Diffraction angle (2θ°) | Relative intensity (%) |
| --- | --- |
| 15.22 | 100 |
| 16.85 | 13.05 |
| 17.54 | 11.14 |
| 17.96 | 22.50 |
| 22.64 | 6.11 |
| 25.90 | 44.92 |
| 26.72 | 6.34 |

The three-dimensional structure of this crystalline form obtained via SC-XR is given in FIG. 44a, and the comparison between the powder diffractogram calculated on the basis of the obtained structure and the experimental XRPD is given in FIG. 44b.

This crystalline form of 6-(1H-imidazol-1-yl)-2-phenylquinazoline fumarate (fumarate salt form A), is also characterized by the DSC spectrum given in FIG. 45, which shows an endothermic event with onset at about 190° C., a second endothermic event with onset at about 209° C., and a third endothermic event with onset at about 240° C. (the weight loss corresponding to these events corresponds to the loss of maleic anhydride, TGA-FT-IR).

This crystalline form of 6-(1H-imidazol-1-yl)-2-phenylquinazoline fumarate, (fumarate salt form A), is also characterized by the FT-IR spectrum (ATR) given in FIG. 46.

Crystalline form of 6-(1H-imidazol-1-yl)-2-phenylquinazoline maleate ($C_{17}H_{12}N_4.C_4H_4O_4$) (maleate salt form A), characterized by a triclinic system with cell parameters a=8.9412 (5) Å, b=9.8081 (5) Å, c=10.5922 (6) Å, α: 90.517° (4), β=101.969° (5), γ=99.132° (4), V=896.34 (8) Å$^3$, space group P-1, with the XRPD spectrum given in FIG. 47 and comprising the main peaks given in Table 16. The three-dimensional structure of this crystalline form obtained via SC-XR is given in FIG. 47a, and the comparison between the powder diffractogram calculated on the basis of the obtained structure and the experimental XRPD is given in FIG. 47b.

TABLE 16

| Diffraction angle (2θ°) | Relative intensity (%) |
| --- | --- |
| 8.77 | 7.48 |
| 9.31 | 5.48 |
| 12.05 | 10.50 |
| 12.38 | 19.38 |
| 12.75 | 13.37 |
| 15.89 | 61.96 |
| 18.49 | 6.18 |
| 20.05 | 19.84 |
| 25.91 | 100 |
| 27.29 | 57.48 |

This crystalline form of 6-(1H-imidazol-1-yl)-2-phenylquinazoline maleate (maleate salt form A), is also characterized by the DSC spectrum given in FIG. 48, which shows an endothermic event with onset at about 156° C., and a second endothermic event with onset at about 243° C. (the weight loss corresponding to these events corresponds to the loss of maleic anhydride, TGA-FT-IR).

This crystalline form of 6-(1H-imidazol-1-yl)-2-phenylquinazoline maleate (maleate salt form A), is also characterized by the FT-IR spectrum (ATR) given in FIG. 49.

Crystalline form of 6-(1H-imidazol-1-yl)-2-phenylquinazoline maleate ($C_{17}H_{12}N_4.C_4H_4O_4.\ 1/2H_2O$), (maleate salt form B), characterized by the XRPD spectrum given in FIG. 50 and comprising the main peaks given in Table 17.

TABLE 17

| Diffraction angle (2θ°) | Relative intensity (%) |
| --- | --- |
| 8.77 | 7.48 |
| 9.31 | 5.48 |
| 12.05 | 10.50 |
| 12.38 | 19.38 |
| 12.75 | 13.37 |
| 15.89 | 61.96 |
| 18.49 | 6.18 |
| 20.05 | 19.84 |
| 25.91 | 100 |
| 27.29 | 57.48 |

This crystalline form of 6-(1H-imidazol-1-yl)-2-phenylquinazoline maleate hemihydrate (maleate salt form B), is also characterized by the DSC spectrum given in FIG. 51, which shows an endothermic event with a peak at about 83° C., an endothermic event with onset at about 153° C. and an endothermic event with onset at about 228° C.

This crystalline form of 6-(1H-imidazol-1-yl)-2-phenylquinazoline maleate hemihydrate (maleate salt form B), is also characterized by the FT-IR spectrum (ATR) given in FIG. 52.

The maleate of 6-(1H-imidazol-1-yl)-2-phenylquinazoline and in particular its crystalline form A, among the stable salts obtained for this product, is the one which, although not endowed with excessive solubility (Example 58), showed the best bioavailability (Example 59). In addition, 6-(1H-imidazol-1-yl)-2-phenylquinazoline maleate form A was found to be entirely non-hygroscopic (Example 57) and relatively stable with respect to mechanical stress (Example 56). This form is therefore very useful for the preparation of immediate-release oral pharmaceutical forms such as tablets and capsules, since it has suitable solubility, stability and processability characteristics. In addition, on account of its good solubility, it can also be used in injectable formulations, since the pH of its solutions, even highly concentrated solutions, is physiologically much more compatible than that of the corresponding hydrochloride or dihydrochloride.

Crystalline form of 6-(1H-imidazol-1-yl)-2-phenylquinazoline phosphate ($C_{17}H_{12}N_4.H_2PO_4$) (phosphate salt form A), characterized by the XRPD spectrum given in FIG. 53 and comprising the main peaks given in Table 18.

TABLE 18

| Diffraction angle (2θ°) | Relative intensity (%) |
| --- | --- |
| 4.40 | 59.84 |
| 9.96 | 10.52 |
| 10.82 | 7.62 |
| 13.18 | 25.36 |
| 16.43 | 100 |
| 19.98 | 15.26 |
| 20.42 | 18.82 |
| 26.22 | 9.00 |

This crystalline form of 6-(1H-imidazol-1-yl)-2-phenylquinazoline phosphate (phosphate salt form A) is also characterized by a melting point 242-246° C.

Crystalline form of 6-(1H-imidazol-1-yl)-2-phenylquinazoline oxalate ($C_{17}H_{12}N_4.C_2H_2O_4$) (oxalate salt form A), characterized by the XRPD spectrum given in FIG. 54 and comprising the main peaks given in Table 19.

TABLE 19

| Diffraction angle (2θ°) | Relative intensity (%) |
| --- | --- |
| 4.26 | 39.40 |
| 8.50 | 11.09 |
| 9.91 | 10.85 |
| 16.45 | 100 |
| 16.60 | 68.72 |
| 19.27 | 13.10 |
| 24.90 | 32.66 |

This crystalline form of 6-(1H-imidazol-1-yl)-2-phenylquinazoline oxalate (oxalate salt form A), is also characterized by the DSC spectrum given in FIG. 55, which shows an endothermic event with onset at about 229° C.

This crystalline form of 6-(1H-imidazol-1-yl)-2-phenylquinazoline oxalate, (oxalate salt form A), is also characterized by the FT-IR spectrum (ATR) given in FIG. 56.

Representative examples of preparation of the compounds of the invention and determination of their properties are given hereinbelow.

EXAMPLE 1

Preparation of 6-(1H-imidazol-1-yl)-2-phenylquinazoline, (C$_{17}$H$_{12}$N$_4$), Polymorph A, (method A)

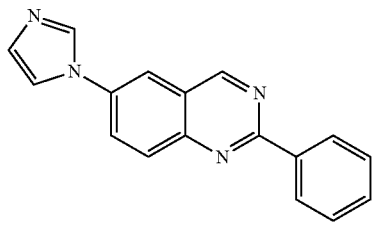

6-(1H-Imidazol-1-yl)-2-phenylquinazoline (2.7 g) is suspended in acetonitrile (300 mL), the suspension is heated to reflux, the mixture is filtered while hot, the filtrate is cooled to 40° C., about half the solvent is distilled off under a gentle vacuum, and ethyl acetate is slowly added (150 mL). The mixture is allowed to cool to room temperature, it is stirred at this temperature for 3 hours, filtered and dried at 50° C., 25 mmHg for 6 hours. 2.1 g (78%) of an ochre-yellow product are obtained, KF<0.5%, XRPD: polymorph A. m.p.: 180.4° C. (DSC), TGA: no weight loss is observed in the range 40-180° C. Calculated for C$_{17}$H$_{12}$N$_4$: C, 74.98; H, 4.44; N, 20.57. found: C, 74.82; H, 4.41; N, 20.68. $^1$H NMR (DMSO-d$_6$) 9.72 (s, 1H), 8.39-8.63 (m, 5H), 8.23 (d, 1H), 8.00 (s, 1H), 7.58-7.62 (m, 3H), 7.23 (s, 1H). Polymorph A may similarly be obtained from dimethylformamide (DMF)/ethyl acetate, DMF/acetone, DMF/methyl ethyl ketone, dichloromethane (DCM)/ethyl acetate or DCM/acetone.

EXAMPLE 2

Preparation of 6-(1H-imidazol-1-yl)-2-phenylquinazoline, (C$_{17}$H$_{12}$N$_4$), Polymorph A, (method B)

6-(1H-Imidazol-1-yl)-2-phenylquinazoline, 236 g, is dissolved in 250 mL of refluxing methanol, the hot solution is filtered and is added, with stirring, to 1.5 L of acetone at 40°-50° C., and the resulting suspension is concentrated at 30°-40° C., under a gentle vacuum to about half its volume, and then allowed to cool to room temperature and stirred overnight at this temperature. The mixture is filtered and the product is washed with acetone and dried at 50° C., 25 mmHg, for 12 hours. 208 g (88%) of an ochre-yellow product are obtained, KF<0.5%, XRPD: polymorph A. Polymorph A may similarly be obtained from methanol/ethyl acetate.

EXAMPLE 3

Preparation of 6-(1H-imidazol-1-yl)-2-phenylquinazoline, (C$_{17}$H$_{12}$N$_4$), Polymorph A, (by conversion of other crystalline forms into form A)

6-(1H-Imidazol-1-yl)-2-phenylquinazoline (2.6 g), is dissolved in 250 mL of refluxing DCM, the hot solution is filtered and added, with stirring, to 1.5 L of acetone at 40°-50° C., the resulting suspension is concentrated at 30°-40° C., under a gentle vacuum to about half its volume, and then cooled to +5° C. and stirred at this temperature for one hour. The mixture is filtered and the product is washed with acetone and dried at 40° C., 20 mmHg, for 8 hours. 2.08 g (80%) of an ochre-yellow product are obtained, XRPD: mixture of polymorphs A+C. The mixture thus obtained is suspended at room temperature in 100 mL of ethyl acetate and stirred at this temperature for 3 days, filtered and dried at 40° C., 20 mmHg, for 8 hours. 1.73 g (83%) of an ochre-yellow product are obtained, KF<0.5%, XRPD: polymorph A. In a manner analogous to that described, the binary or ternary mixtures of the crystalline forms A, B, C, D, E may be converted into polymorph A, by stirring the suspension in one of the following solvents: acetonitrile, tert-butyl methyl ether (TBME), diethyl ether, ethyl acetate, isopropyl acetate, isopropyl ether, hexane. The stirring in suspension must also be continued for 7 days, depending on the solvent used and on the composition of the mixture of polymorphs to be converted.

EXAMPLE 4

Stability of Form A in Suspension 6-(1H-Imidazol-1-yl)-2-phenylquinazoline polymorph A (150 mg) was suspended in 5 mL of solvent and stirred at 25±5° C. for 7 days, and then filtered, and the filtrate was subjected to XRPD analysis.

Form A is found to be stable when stirred in suspension at room temperature, in the following solvents: DCM, propanol, ethyl ether, tert-butyl methyl ether, acetone, ethyl acetate, isopropyl acetate, toluene, hexane.

EXAMPLE 5

Thermal Stability

Polymorph A, when heated, proves to be stable at 40° C., RH 85%, for at least 5 days, and is also stable when heated at 90° C. for at least 12 hours; in point of fact no formation of the other forms (XRPD) and no peaks foreign to polymorph A are found in any case.

EXAMPLE 6

Stability of Form a to Mechanical Stress (Milling)

6-(1H-Imidazol-1-yl)-2-phenylquinazoline, polymorph A, was subjected to milling by means of a Retsch MM 200 mill, at 50 Hz for 5 min., and the product thus obtained was analysed by XRPD. The diffractogram of Form A was obtained without any contamination with other crystalline forms, and no appreciable formation of amorphous material during milling is detected.

EXAMPLE 7

Solubility of Form A

A sample of 6-(1H-imidazol-1-yl)-2-phenylquinazoline, polymorph A (150 mg), is stirred in a phosphate buffer solution at pH 7.4 (8 mL), at 500 rpm, so as to obtain a suspension, for 24 hours at 37° C. The suspension is then filtered and the concentration of the dissolved product is measured by reading the UV absorbance at 260 nm. The solubility is less than 0.1 mg/mL (0.02-0.06 mg/mL). A sample of 6-(1H-imidazol-1-yl)-2-phenylquinazoline, polymorph A (250 mg), is stirred in a phosphate buffer solution at pH 2 (2 mL), at 500 rpm, so as to obtain a suspension, for 24 hours at 37° C. The suspension is then filtered and the concentration of the dissolved product is measured by reading the UV absorbance at 260 nm. The solubility is 1.8 mg/mL.

EXAMPLE 8

Bioavailability of Polymorph A

The pharmacokinetics of 6-(1H-imidazol-1-yl)-2-phenylquinazoline, polymorph A, were evaluated in rats, by comparing the oral administration (10 mg/Kg, Hypromellose 0.5%, Tween 80 0.4%, benzyl alcohol 0.9%, sodium chloride 0.9%, in distilled water) with the intravenous administration (5 mg/kg, DMSO/Tween 80/0.9% NaCl 10:10:80), blood samples being collected at times: 5, 15, 30, 60, 120, 240, 360, 480 and 720 min. The samples are analysed by HPLC-MS to determine the content of 6-(1H-imidazol-1-yl)-2-phenylquinazoline, using diphenylhydramine hydrochloride as internal standard. The pharmacokinetic parameters measured are summarized hereinbelow: it is noted that, despite the fact that the polymorph under consideration is of low solubility, the bioavailability (F %) is entirely acceptable.

| PK parameters for 6-(1H-imidazol-1-yl)-2-phenylquinazoline, polymorph A | | | | |
|---|---|---|---|---|
| Route | T½ (min). | V L/Kg | CL (L/Kg/min) | F (%) |
| IV | 42.1 | 1.28 | 0.021 | — |
| OS | 45.40 ($T_{max}$: 100 min) | 1.60 | 0.022 | 50.3 |

EXAMPLE 9

Preparation of 6-(1H-imidazol-1-yl)-2-phenylquinazoline monohydrate ($C_{17}H_{12}N_4.H_2O$), form B (method A)

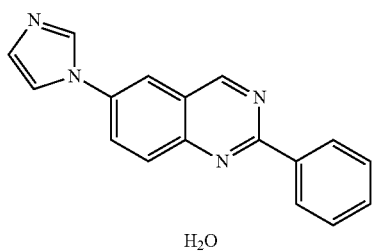 [SMILES: c1ccc(-c2ncc3cc(-n4ccnc4)ccc3n2)cc1 ; O]

H₂O 50 mg of 6-(1H-imidazol-1-yl)-2-phenylquinazoline are suspended in 4 mL of isopropanol, the suspension is heated at 70° C. for a few minutes, and then filtered and left to evaporate slowly at room temperature, at rest. The crystals obtained are analysed. XRPD: Form B. TGA: weight loss: 6.8% (theoretical value for $C_{17}H_{12}N_4.H_2O$: 6.2%), TGA-IR in accordance with the spectrum of $H_2O$ for the released vapours. Form B may be obtained analogously from n-propanol and from ethanol.

EXAMPLE 10

Preparation of 6-(1H-imidazol-1-yl)-2-phenylquinazoline monohydrate ($C_{17}H_{12}N_4.H_2O$), form B (method B)

2.5 g of 6-(1H-imidazol-1-yl)-2-phenylquinazoline are suspended in 200 mL of isopropanol, the suspension is heated at reflux, with stirring, for 30 minutes, and the mixture is then filtered while hot, the solvent is evaporated off at 75° C. under a gentle vacuum down to a volume of about 50-80 mL, and the resulting mixture is then cooled with gentle stirring at +5° C., for about 2 hours. The solid obtained is filtered off, washed with cold isopropanol and dried at 40° C., 20 mmHg, for 12 hours. 2.2 g (88%) of an ochre-yellow product are obtained, XRPD: Form B. KF: 6.5%, Calculated for $C_{17}H_{12}N_4.H_2O$: C, 70.33; H, 4.86; N, 19.30. found C, 70.22; H, 4.91; N, 19.25. $^1$H NMR (DMSO-$d_6$) 9.72 (s, 1H), 8.39-8.63 (m, 5H), 8.23 (d, 1H), 8.00 (s, 1H), 7.58-7.62 (m, 3H), 7.23 (s, 1H); form B may similarly be prepared from n-propanol, butanol, t-butanol.

EXAMPLE 11

Thermal Stability

Form B is heated at 40° C., RH 85%, for 7 days: the appearance of the signals of form E in the XRPD spectrum is noted. In a variable temperature experiment (VT-XRPD), form B, when heated to between 40° C. and 180° C., shows conversion into form E, before reaching a temperature of 180° C. The conversion takes place without passing through melting, but it is already very pronounced in the range 40-80° C. and is already virtually complete at 120-130° C. On cooling to room temperature, polymorph E thus formed is stable.

EXAMPLE 12

Solubility of Form B

A sample of 6-(1H-imidazol-1-yl)-2-phenylquinazoline, form B, (50 mg), is stirred in a phosphate buffer solution at pH 7.4 (2 mL), at 500 rpm, so as to obtain a suspension, for 24 hours at 37° C. The suspension is then filtered and the concentration of the dissolved product is measured by reading the UV absorbance at 260 nm. The solubility is about 0.1 mg/mL (0.08-0.12 mg/mL).

EXAMPLE 13

Preparation of 6-(1H-imidazol-1-yl)-2-phenylquinazoline monohydrate ($C_{17}H_{12}N_4.H_2O$), form C (method A)

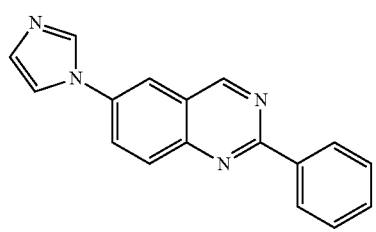 [SMILES: c1ccc(-c2ncc3cc(-n4ccnc4)ccc3n2)cc1]

H₂O 50 mg of 6-(1H-imidazol-1-yl)-2-phenylquinazoline are suspended in 2 mL of methanol, the suspension is heated at reflux for a few minutes, and then filtered and left to evaporate slowly at room temperature, at rest. The crystals obtained are analysed. XRPD: Form C. TGA: weight loss: 6.32% (theoretical value for $C_{17}H_{12}N_4.H_2O$: 6.2%), TGA-IR in agreement with the IR spectrum of $H_2O$ for the released vapours.

EXAMPLE 14

Preparation of 6-(1H-imidazol-1-yl)-2-phenylquinazoline monohydrate ($C_{17}H_{12}N_4.H_2O$), form C (method B)

1.5 g of 6-(1H-imidazol-1-yl)-2-phenylquinazoline are suspended in 15 mL of methanol, the suspension is heated at reflux for 5 minutes, it is then filtered and cooled with stirring to 0° C., 10 mL of tert-butyl methyl ether are added with stirring, stirring is continued at 0° C. for a further 5 min and the product is then filtered off and dried at 40° C., 20 mmHg, for 12 hours. 1 g (68%) of product is obtained in the form of yellow crystals. The crystals obtained are analysed. XRPD: Form C. KF: 6.4%, Calculated for $C_{17}H_{12}N_4.H_2O$: C, 70.33; H, 4.86; N, 19.30. found C, 70.29; H, 4.88; N, 19.31. $^1$H NMR (DMSO-d6) 9.72 (s, 1H), 8.39-8.63 (m, 5H), 8.23 (d, 1H), 8.00 (s, 1H), 7.58-7.62 (m, 3H), 7.23 (s, 1H); form C is obtained in a similar manner using ethyl ether or tetrahydrofuran as anti-solvent.

EXAMPLE 15

Preparation of 6-(1H-imidazol-1-yl)-2-phenylquinazoline monohydrate ($C_{17}H_{12}N_4.H_2O$), form C (method C)

3 g of 6-(1H-imidazol-1-yl)-2-phenylquinazoline are suspended in 80 mL of ethanol, the suspension is heated at reflux for 10 minutes, and then filtered while hot, the resulting solution is added at room temperature to 80 mL of water, with stirring, stirring is continued for a further 5 min and the mixture is then filtered and dried at 20° C., 10 mmHg, for 12 hours. 2.3 g (75%) of product are obtained in the form of a yellow powder. The crystals obtained are analysed. XRPD: Form C. Form C is similarly obtained by precipitating the product from methanol/$H_2O$.

EXAMPLE 16

Stability of Form C in Suspension 6-(1H-Imidazol-1-yl)-2-phenylquinazoline polymorph C (150 mg) is suspended in 5 mL of solvent and stirred at 25±5° C. for 7 days and then filtered, and the filtrate was subjected to XRPD analysis, which reveals the stability from the consistency of the spectrum. Form C is stable when stirred in suspension at room temperature, in $H_2O$, whereas, in the following solvents: ethyl ether, dimethyl tert-butyl ether, DCM, acetone, ethyl acetate, isopropyl acetate, it is converted into form A. Forms A, B, D and E are converted into form C when suspended with stirring in $H_2O$, at 25±5° C. for 7 days.

EXAMPLE 17

Thermal Stability

Form C is heated at 40° C., RH 85%, for 5 days, and form C is stable under these conditions since no appearance of other signals in the XRPD spectrum is noted. Form C heated at 90° C. for 3 hours shows complete conversion into form E (XRPD). On cooling to room temperature, the polymorph E thus formed is stable.

EXAMPLE 18

Solubility of Form C

A sample of 6-(1H-imidazol-1-yl)-2-phenylquinazoline, form C (30 mg), is stirred in a phosphate buffer solution at pH 7.4 (2 mL), at 500 rpm, so as to obtain a suspension, for 24 hours at 37° C. The suspension is then filtered and the concentration of the dissolved product is measured by reading the UV absorbance at 260 nm. The solubility is about 0.1 mg/mL (0.06-0.10 mg/mL).

EXAMPLE 19

Preparation of 6-(1H-imidazol-1-yl)-2-phenylquinazoline ($C_{17}H_{12}N_4$), polymorph D (method A)

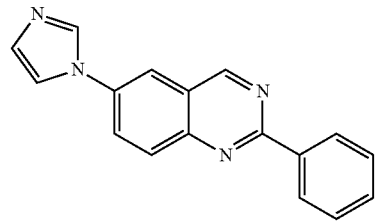 [SMILES: c1ccc(-c2ncc3cc(-n4ccnc4)ccc3n2)cc1]

50 mg of 6-(1H-imidazol-1-yl)-2-phenylquinazoline are suspended in 15 mL of tert-butyl methyl ether, the suspension is heated at reflux for a few minutes, and then filtered and left to evaporate slowly at room temperature, at rest. The crystals obtained are analysed: XRPD: polymorph D, TGA: no weight loss is observed in the range 40-180° C.

EXAMPLE 20

Preparation of 6-(1H-imidazol-1-yl)-2-phenylquinazoline ($C_{17}H_{12}N_4$), polymorph D (method B)

1.2 g of 6-(1H-imidazol-1-yl)-2-phenylquinazoline are suspended in 150 mL of isopropyl acetate, the suspension is heated at reflux, with stirring for 30 minutes, and then filtered while hot and concentrated at 70° C. under a gentle vacuum. When the volume is about 50 mL, the distillation is stopped and the mixture is stirred at 70-60° C. for a further 5 min., and then filtered and dried at 40° C., 20 mmHg, for 6 hours. 560 mg (47%) of product are obtained in the form of pale yellow crystals. The crystals obtained are analysed. XRPD: Polymorph D. $^1$H NMR (DMSO-d6) 9.72 (s, 1H), 8.39-8.63 (m, 5H), 8.23 (d, 1H), 8.00 (s, 1H), 7.58-7.62 (m, 3H), 7.23 (s, 1H); by working in a similar manner, but cooling to +5° C. and filtering at this temperature, a mixture of polymorph D and form C is obtained. This mixture of crystalline forms, suspended in dry ethyl ether and stirred at room temperature for 6 days, converts into pure polymorph D. Pure form D is also obtained by working as described above, cooling to room temperature over about two hours and filtering at room temperature. Pure form D is also obtained by working as described above but using methyl ethyl ketone (MEK) as solvent.

EXAMPLE 21

Thermal Stability

Form D is heated at 40° C., RH 85%, for 7 days, and form D is stable under these conditions, since no appearance of other signals in the XRPD spectrum is noted. Form D heated at 90° C. for 3 hours proves to be stable (XRPD). On further heating to 160° C., form D melts and recrystallizes into form A (XRPD).

EXAMPLE 22

Solubility of Form D

A sample of 6-(1H-imidazol-1-yl)-2-phenylquinazoline, form D, (50 mg), is stirred in a phosphate buffer solution at pH 7.4 (2 mL), at 500 rpm, so as to obtain a suspension, for 24 hours at 37° C. The suspension is then filtered and the concentration of the dissolved product is measured by reading the UV absorbance at 260 nm. The solubility is about 0.1 mg/mL (0.04-0.06 mg/mL).

EXAMPLE 23

Preparation of 6-(1H-imidazol-1-yl)-2-phenylquinazoline ($C_{17}H_{12}N_4$), polymorph E (method A)

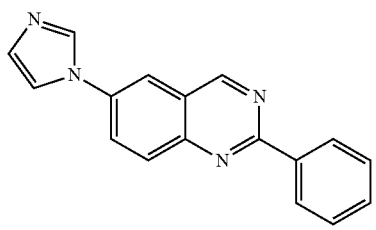

50 mg of 6-(1H-imidazol-1-yl)-2-phenylquinazoline are suspended in 6 mL of p-xylene, the suspension is heated at reflux for a few minutes, and then filtered and left to evaporate slowly at room temperature, at rest. The crystals obtained are analysed. XRPD: Polymorph E. TGA: no weight loss is observed in the range 40-180° C.

EXAMPLE 24

Preparation of 6-(1H-imidazol-1-yl)-2-phenylquinazoline, polymorph E (method B)

250 mg of 6-(1H-imidazol-1-yl)-2-phenylquinazoline are suspended in 20 mL of DCM, the suspension is heated at reflux for a few minutes, and then filtered and allowed to evaporate slowly at room temperature, under a gentle vacuum. The crystals obtained are analysed. XRPD: Polymorph E.

EXAMPLE 25

Preparation of 6-(1H-imidazol-1-yl)-2-phenylquinazoline, polymorph E (method C)

1.5 g of 6-(1H-imidazol-1-yl)-2-phenylquinazoline are suspended in 15 mL of methanol, the suspension is heated at reflux for 5 minutes, and then filtered while hot and added slowly, with stirring, to 150 mL of p-xylene heated to 120° C., the methanol is then allowed to evaporate off, the mixture is cooled with stirring to 50-60° C., the volume is reduced to about 100 mL by applying a gentle vacuum, the resulting mixture is stirred slowly for a further 30 min., and is then filtered, and washed with xylene and dried at 60° C., 10 mmHg, for 24 hours. 1.4 g (98%) of product are obtained in the form of yellow crystals. The crystals obtained are analysed, XRPD: polymorph E. $^1$H NMR (DMSO-d6) 9.72 (s, 1H), 8.39-8.63 (m, 5H), 8.23 (d, 1H), 8.00 (s, 1H), 7.58-7.62 (m, 3H), 7.23 (s, 1H). By working in a similar manner, but using toluene and p-xylene, a mixture of polymorphs A+E is obtained.

EXAMPLE 26

Thermal Stability

Form E heated at 40° C., RH 85%, for 7 days, is stable under these conditions, since no appearance of other signals is noted (XRPD). Form E heated at 90° C. for 3 hours proves to be stable (XRPD). On further heating to 162-165° C., form E melts and recrystallizes into form A (XRPD).

EXAMPLE 27

Solubility of Form E

A sample of 6-(1H-imidazol-1-yl)-2-phenylquinazoline, form E, (80 mg), is stirred in a phosphate buffer solution at pH 7.4 (3 mL), at 500 rpm, so as to obtain a suspension, for 24 hours at 37° C. The suspension is then filtered and the concentration of the dissolved product is measured by reading the UV absorbance at 260 nm. The solubility is about 0.2 mg/mL (0.24-0.21 mg/mL).

EXAMPLE 28

Preparation of 6-(1H-imidazol-1-yl)-2-phenylquinazoline dihydrochloride monohydrate (hydrochloride salt form A)

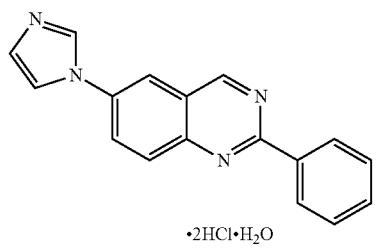 [SMILES: c1ccc(-c2ncc3cc(-n4ccnc4)ccc3n2)cc1]

·2HCl·H$_2$O 6-(1H-Imidazol-1-yl)-2-phenylquinazoline, 500 mg (1.8 mmol), is suspended in 20 mL of ethanol, the mixture is heated to 60° C., with stirring, 4.5 mL of 1N hydrochloric acid are added, the mixture is stirred for a few minutes, concentrated to half its volume and then allowed to cool to room temperature, the resulting suspension is stirred at +5° C. overnight, and the mixture is then filtered and the product is washed with acetone and dried at 20° C., 20 mmHg, for 12 hours. 660 mg (97%) of non-hygroscopic yellow crystals are obtained, XRPD form A. KF: 4.7% $^1$H NMR (d$_6$-DMSO+ D$_2$O) δ: 9.96 (d, 1H), 9.83 (m, 1H), 8.72 (d, 1H), 8.5 (m, 1H), 8.30-7.92 (m, 3H), 7.60-7.25 (m, 5H). Calculated for $C_{17}H_{12}N_4 \cdot 2HCl \cdot H_2O$: C, 56.21; H, 4.44; N, 15.42; Cl, 19.52. Found, C, 56.18; H, 4.53; N, 15.48; Cl, 19.48. Form A may be obtained in a similar manner from: methanol, isopropanol, water (10 mL/g), and ethanol/H$_2$O or methanol/H$_2$O mixtures or mixtures of methanol or ethanol with acetone, dioxane or tetrahydrofuran (THF).

EXAMPLE 29

Stability of Form A in Suspension 6-(1H-Imidazol-1-yl)-2-phenylquinazoline dihydrochloride monohydrate, form A (60 mg), was suspended in 1 mL of solvent and stirred at 25±5° C. for 7 days and then filtered and the filtrate is subjected to XRPD analysis. Form A is stable when stirred in suspension at room temperature, for seven days, in the following solvents: DCM, ethyl ether, tert-butyl methyl ether, acetone, ethyl acetate, isopropyl acetate, THF, hexane.

EXAMPLE 30

Thermal Stability

Form A is stable at 40° C., RH 85%, for 7 days; in addition, it is stable at 90° C. for several hours. In point of fact, the formation of the monohydrochloride is noted only after 36 hours, and complete conversion into the monohydrochloride is noted only after 48 hours at 90° C., as may be seen in FIG. 19b (VT-XRPD).

EXAMPLE 31

Stability of Form A to Mechanical Stress (Milling)

6-(1H-Imidazol-1-yl)-2-phenylquinazoline dihydrochloride monohydrate form A was subjected to milling by means of a Retsch MM 200 mill, at 50 Hz for 5 min., and the product thus obtained was subjected to XRPD analysis. No increase in the amount of amorphous product present relative to the reference example, as well as no foreign signals attributable to other forms, is revealed in the spectrum of form A.

EXAMPLE 32

Stability of Form A to Moisture

The sample of 6-(1H-imidazol-1-yl)-2-phenylquinazoline dihydrochloride monohydrate form A was subjected to DVS analysis (Differential Vapour Sorption). The sample placed on a microbalance is subjected, in a chamber of controlled humidity, at 25° C., to a cycle of hydration (increasing humidity, red line) and of dehydration (decreasing humidity, blue line). The change is given in FIG. 19c. It is noted that, in the range 30-80% relative humidity (RH), the product is not particularly hygroscopic, since the water content remains at about 5% (value corresponding to the monohydrate).

EXAMPLE 33

Solubility of Form A

The sample of 6-(1H-imidazol-1-yl)-2-phenylquinazoline dihydrochloride monohydrate, form A (450 mg), is stirred in an aqueous solution of NaCl 0.9% (2 mL), at 500 rpm, so as to obtain a suspension, for 24 hours at 37° C. The suspension is then filtered and the concentration of the dissolved product is measured by reading the UV absorbance at 260 nm. The solubility is 138 mg/mL. The dissolution rate is measured by adding 2 mg of product to 40 mL of water at 37° C., stirring at 500 rpm, and measuring the absorbance at 260 nm every 0.05 min; the dissolution rate is found to be $2.17 \times 10^{-3}$ gr/min.

EXAMPLE 34

Bioavailability of Form A

The pharmacokinetics of 6-(1H-imidazol-1-yl)-2-phenylquinazoline dihydrochloride monohydrate, form A, were evaluated in rats by working as described in Example 8. The pharmacokinetic parameters measured are summarized hereinbelow: it is noted that the salt under consideration has optimum bioavailability (F %).

| PK parameters for 6-(1H-imidazol-1-yl)-2-phenylquinazoline dihydrochloride monohydrate form A | | | | |
|---|---|---|---|---|
| Route | T½ (min). | V L/Kg | CL (L/Kg/min) | F (%) |
| IV | 46.6 | 1.26 | 0.024 | — |
| OS | 59.9 (T$_{max}$: 80 min) | 2.96 | 0.018 | 90.0 |

EXAMPLE 35

Preparation of 6-(1H-imidazol-1-yl)-2-phenylquinazoline hydrochloride (hydrochloride salt form B)

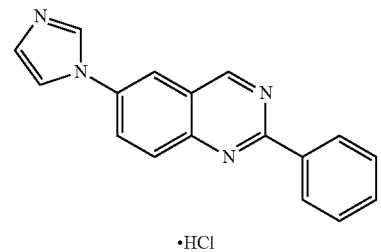 [SMILES: c1ccc(-c2ncc3cc(-n4ccnc4)ccc3n2)cc1 ; Cl]

·HCl 6-(1H-Imidazol-1-yl)-2-phenylquinazoline, 500 mg (1.8 mmol), is suspended in 20 mL of acetonitrile, the mixture is then heated at 50° C., with stirring for 10 min., it is cooled to room temperature and 4 mL of HCl-saturated isopropyl ether are added, the mixture is stirred for a few minutes, it is concentrated to dryness, the residue is taken up in 10 mL of acetonitrile with stirring at room temperature for 2 hours, and the mixture is then filtered and the product is washed with acetone and dried at 20° C., 20 mmHg, for 12 hours. 730 mg (99%) of hygroscopic product are obtained in the form of yellow crystals, XRPD form B. KF: 1.2%. $^1$H NMR (200 MHz, $d_6$-DMSO+$D_2$O) δ: 9.96 (d, 1H), 9.83 (m, 1H), 8.72 (d, 1H), 8.5 (m, 1H), 8.30-7.92 (m, 3H), 7.60-7.25 (m, 5H). Calculated for $C_{17}H_{12}N_4$.: C, 66.13; H, 4.24; N, 18.14; Cl, 11.48. Found, C, 60.38; H, 4.48; N, 17.98; Cl, 11.26.

EXAMPLE 36

Preparation of
6-(1H-imidazol-1-yl)-2-phenylquinazoline succinate
(succinate salt form A)

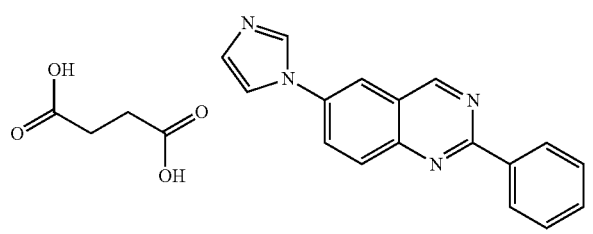

6-(1H-Imidazol-1-yl)-2-phenylquinazoline, 500 mg (1.8 mmol), is suspended in 40 mL of ethanol (EtOH), the mixture is heated to 60° C. with stirring, 220 mg of succinic acid are added, the mixture is stirred for a few minutes, 20 mL of ethyl acetate (EtOAc) are added slowly, the mixture is allowed to cool to room temperature, the resulting suspension is stirred at +25° C. overnight, and then filtered, washed with EtOAc and dried at 25° C., 20 mmHg, for 8 hours. 670 mg (95%) of non-hygroscopic yellow crystals are obtained, KF<0.5%, XRPD: Form A. Form A may be obtained in a similar manner from methanol or isopropanol as a mixture with acetone or isopropyl acetate. The crystal for determination of the cell structure (SC-XR) was obtained by dissolving 50 mg of 6-(1H-imidazol-1-yl)-2-phenylquinazoline succinate in boiling EtOH (2 mL), and then leaving to stand at room temperature, to give a few crystals. The one used for SC-XR hand dimensions of about 0.4×0.4×0.02 mm Form A was found to be stable (consistent XRPD) by heating at 40° C., 85% RH, for 7 days, and is stable by heating at 90° C. for at least 12 hours. The SC-XR determination was performed at room temperature, using an Oxford Xcalibur S radiation Mo-K refractometer, λ=0.71073 Å with a graphite monochromator and a Sapphire CCD detector.

EXAMPLE 37

Stability of Form A to Mechanical Stress (Milling)

6-(1H-Imidazol-1-yl)-2-phenylquinazoline succinate form A, was subjected to milling by means of a Retsch MM 200 mill, at 50 Hz for 5 min., and the product thus obtained was subjected to XRPD analysis. The diffractogram obtained shows that form A has not undergone any changes of crystalline form and no presence of amorphous product is revealed.

EXAMPLE 38

Stability of Form A to Moisture

The sample of 6-(1H-imidazol-1-yl)-2-phenylquinazoline succinate form A was subjected to DVS analysis (as described in Example 32). The change is given in FIG. 30. It is noted that the product is not entirely hygroscopic and only at about 90% RH is there a significant minimum absorption of water.

EXAMPLE 39

Solubility of Form A

The sample of 6-(1H-imidazol-1-yl)-2-phenylquinazoline succinate form A is stirred in an aqueous solution of NaCl 0.9%, at 500 rpm, so as to obtain a suspension, for 24 hours at 37° C. The suspension is then filtered and the concentration of the dissolved product is measured by reading the UV absorbance at 260 nm. The solubility is 0.6 mg/mL. The dissolution rate is measured by adding 2 mg of product to 40 mL of water at 37° C., stirring at 500 rpm, and measuring the absorbance at 260 nm every 0.05 min; the dissolution rate is found to be $3.53 \times 10^{-5}$ gr/min.

EXAMPLE 40

Bioavailability of Form A

The pharmacokinetics of 6-(1H-imidazol-1-yl)-2-phenylquinazoline succinate, form A, were evaluated in rats as described in Example 8, and the pharmacokinetic parameters measured are summarized hereinbelow: it is noted that, despite the fact that the salt under consideration does not have optimum solubility, the bioavailability (F %) is better than that of the free base.

| PK parameters for 6-(1H-imidazol-1-yl)-2-phenylquinazoline succinate form A | | | | |
|---|---|---|---|---|
| Route | T½ (min). | V L/Kg | CL (L/Kg/min) | F (%) |
| IV | 48.9 | 1.1 | 0.018 | — |
| OS | 48.57 ($T_{max}$: 60 min) | 3.74 | 0.019 | 65.0 |

EXAMPLE 41

Preparation of
6-(1H-imidazol-1-yl)-2-phenylquinazoline succinate
(succinate salt form B)

6-(1H-Imidazol-1-yl)-2-phenylquinazoline, 500 mg (1.8 mmol), is suspended in 40 mL of EtOH, the mixture is then heated at reflux, with stirring, 280 mg of succinic acid are added, the mixture is stirred at reflux for a further 30 min., dioxane (200 mL) is added while distilling off the solvent (150 mL), and the suspension thus obtained is cooled in an ice bath, filtered, washed with dioxane and dried at 25° C., 20 mmHg, for 20 hours. 580 mg (865%) of non-hygroscopic yellow crystals are obtained, KF<0.5%, XRPD: Form B. Calculated for $C_{17}H_{12}N_4.C_4H_6O_4$: C, 64.61; H, 4.65; N, 14.35. found: C, 64.02; H, 4.67; N, 14.44; H-NMR ($d_6$-DMSO) δ: 9.75 (s, 1H), 8.58 (m, 2H), 8.46 (d, 2H), 8.38 (d, 1H), 8.21 (d, 1H), 8.0 (s, 1H), 7.59 (m, 3H), 7.21 (s, 1H), 2.40 (s, 4H). Form B may be converted into form A by heating at 90° C.

EXAMPLE 42

Preparation of
6-(1H-imidazol-1-yl)-2-phenylquinazoline succinate
(succinate salt form C)

6-(1H-Imidazol-1-yl)-2-phenylquinazoline succinate form A, 250 mg, is dissolved in 40 mL of n-propanol, and the solution is allowed to evaporate at room temperature under a gentle vacuum, 50 mmHg. The resulting product, yellow crystals, is not hygroscopic and the XRPD analysis shows it to be form C. A similar result is obtained using EtOH instead of n-propanol. Form C is stable on heating to 90° C.

EXAMPLE 43

Preparation of 6-(1H-imidazol-1-yl)-2-phenylquinazoline (L) tartrate dihydrate (tartrate salt form A)

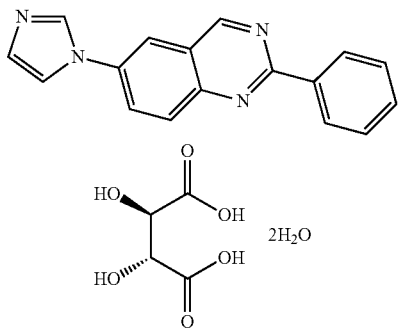

6-(1H-Imidazol-1-yl)-2-phenylquinazoline, 500 mg (1.8 mmol), is suspended in 40 mL of EtOH, the suspension is heated to reflux, with stirring, it is cooled to 50° C. and 300 mg of L-tartaric acid are added, the mixture is stirred for a few minutes, 20 mL of MEK are added slowly, the mixture is then allowed to cool to room temperature, and the resulting suspension is stirred at 0° C. overnight, and then filtered, washed with MEK and dried at 20° C., 20 mmHg, for 12 hours. 730 mg (96%) of non-hygroscopic yellow crystals are obtained, XRPD form A. KF=8.25% Calculated. $C_{17}H_{12}N_4.C_4H_6O_6$: C, 55.02; H, 4.84; N, 12.22. Found: C, 54.78; H, 4.92; N, 12.18. Form A may be obtained in a similar manner from methanol or isopropanol or water, as a mixture with acetone or dioxane or THF. Form A heated at 40° C., 70% RH for 7 days is stable, but gives rise to the amorphous form if it is heated at 90° C. for 12 hours (XRPD).

EXAMPLE 44

Stability of Form A to Mechanical Stress (Milling)

6-(1H-Imidazol-1-yl)-2-phenylquinazoline L-tartrate dihydrate, form A, was subjected to milling by means of a Retsch MM 200 mill, at 50 Hz for 5 min., and the product thus obtained was subjected to XRPD analysis. The diffractogram obtained shows that form A has not undergone any changes of crystalline form, and a slight increase in the presence of amorphous product is revealed.

EXAMPLE 45

Stability of Form A to Moisture

The sample of 6-(1H-imidazol-1-yl)-2-phenylquinazoline L-tartrate dihydrate, form A, was subjected to DVS analysis. The change is given in FIG. 34. It is noted that the product is not hygroscopic in the range 25-70% RH, whereas it shows a point of inflection at 75% RH and becomes highly hygroscopic only at values of greater than 80% RH.

EXAMPLE 46

Solubility of Form A

The sample of 6-(1H-imidazol-1-yl)-2-phenylquinazoline L-tartrate dihydrate, form A, is stirred in an aqueous solution of NaCl 0.9%, at 500 rpm, so as to obtain a suspension (85 mg in 8 mL), for 24 hours at 37° C. The suspension is then filtered and the concentration of the dissolved product is measured by reading the UV absorbance at 260 nm. The solubility is 2.5 mg/mL. The dissolution rate is measured by adding 2 mg of product to 40 mL of water at 37° C., stirring at 500 rpm, and measuring the absorbance at 260 nm every 0.05 min; the dissolution rate is found to be $1.04 \times 10^{-3}$ gr/min.

EXAMPLE 47

Bioavailability of Form A

The pharmacokinetics of 6-(1H-imidazol-1-yl)-2-phenylquinazoline tartrate dihydrate, form A, were evaluated in rats as described in Example 8, and the pharmacokinetic parameters measured are summarized hereinbelow: it is noted that the salt under consideration has optimum bioavailability (F %).

| PK parameters for 6-(1H-imidazol-1-yl)-2-phenylquinazoline tartrate form A | | | | |
|---|---|---|---|---|
| Route | T½ (min). | V L/Kg | CL (L/Kg/min) | F (%) |
| IV | 47.7 | 1.4 | 0.023 | — |
| OS | 47.23 ($T_{max}$: 100 min) | 5.47 | 0.017 | 81.0 |

EXAMPLE 47

Preparation of 6-(1H-imidazol-1-yl)-2-phenylquinazoline (L) tartrate (tartrate salt form B)

6-(1H-Imidazol-1-yl)-2-phenylquinazoline, 50 mg (0.18 mmol), is suspended in 4 mL of acetonitrile, the mixture is then heated at reflux and 30 mg of L-tartaric acid are added, the suspension is heated at reflux for a further 30 min, it is filtered and then cooled to 0° C., and the resulting suspension is stirred at 25° C. for three days and then filtered and dried at 20° C., 20 mmHg, for 12 hours. 30 mg of product are obtained in the form of yellow crystals, KF=14.67%, Calculated for $C_{17}H_{12}N_4.C_4H_6O_6.4H_2O$: C, 51.01; H, 5.30; N, 11.33. found: C, 50.64; H, 5.41; N, 11.28. XRPD form B. Form B heated at 40° C., 85% RH for 7 days is stable (XRPD), but gives rise to the amorphous form when heated at 90° C. for 12 hours.

EXAMPLE 48

Preparation of 6-(1H-imidazol-1-yl)-2-phenylquinazoline (L) tartrate (tartrate salt form C)

6-(1H-Imidazol-1-yl)-2-phenylquinazoline, 500 mg (1.8 mmol), is suspended in 40 mL of isopropanol, the mixture is then heated at reflux with stirring, 300 mg of L-tartaric acid are added, the mixture is stirred for a few minutes, it is filtered, the filtrate is heated to 50° C. evaporating off the solvent under a gentle vacuum to about ⅓ of the volume, then cooled to 0° C. and stirred overnight, and then filtered, washed with a small amount of isopropanol and dried at 20° C., 20 mmHg, for 24 hours. 120 mg of product are obtained in the form of yellow crystals, KF=5.2%, TG-IR LOD 4.93%, the IR spectrum confirms the loss of $H_2O$. XRPD form C.

Calculated for $C_{17}H_{12}N_4.C_4H_6O_6.H_2O$: C, 57.27; H, 4.58; N, 12.72. found: C, 57.16; H, 4.61; N, 12.68.

Form C heated at 40° C., 85% RH for 7 days is stable (XRPD), and is also stable when heated at 90° C. for 12 hours.

EXAMPLE 49

Preparation of 6-(1H-imidazol-1-yl)-2-phenylquinazoline (L) tartrate (tartrate salt form D)

6-(1H-Imidazol-1-yl)-2-phenylquinazoline, 500 mg (1.8 mmol), is dissolved in 50 mL of nitromethane at reflux, with stirring and under a stream of nitrogen, 300 mg of L-tartaric acid are added, the mixture is stirred for a few minutes, it is filtered under nitrogen and the filtrate is heated to 60° C., evaporating off the solvent under a gentle vacuum, with stirring and under a stream of nitrogen, down to about ½ of the volume, and is then allowed to cool to 0° C. under nitrogen, stirred overnight at room temperature, and then filtered and dried at 30° C., 20 mmHg, for 24 hours. 520 mg of product are obtained in the form of yellow crystals, KF<0.5%, Calculated for $C_{17}H_{12}N_4.C_4H_6O_6$: C, 59.71; H, 4.30; N, 13.26. found: C, 59.76; H, 4.34; N, 13.22. XRPD form D. Form D heated at 40° C., 85% RH for 7 days gives an XRPD corresponding to form A, and an amorphous product when heated at 90° C. for 12 hours.

EXAMPLE 50

Preparation of 6-(1H-imidazol-1-yl)-2-phenylquinazoline fumarate (fumarate salt form A)

6-(1H-Imidazol-1-yl)-2-phenylquinazoline, 500 mg (1.8 mmol), is dissolved in 200 mL of EtOH at 40° C., with stirring, and when the solution is clear, 220 mg of fumaric acid are added, and the resulting mixture is stirred for 15 min and then concentrated slowly to the point of precipitation, while applying a gentle vacuum.

The suspension obtained is stirred at room temperature for 2 hours, and then filtered. The non-hygroscopic product obtained is dried at 20° C., 20 mmHg, for 12 hours. 541 mg of product are obtained, KF<0.5%, XRPD form A. Calculated for $C_{17}H_{12}N_4.1/2C_4H_4O_4$: C, 67.93; H, 4.24; N, 16.25. found: C, 67.53; H, 4.27; N, 16.09; H-NMR (d$_6$-DMSO) δ: 9.71 (d. 1H), 8.59-8.56 (m, 3H), 8.49 (m, 1H), 8.46 (d, 1H), 8.21 (d, 1H), 7.97 (s, 1H), 7.95-7.57 (m, 3H), 6.61 (s, 1H). The crystal for determination of the cell structure (SC-XR) was obtained by dissolving 50 mg of 6-(1H-imidazol-1-yl)-2-phenylquinazoline fumarate in boiling EtOH (2 mL), the solution is left to stand at room temperature, and a few crystals are obtained. The one used for SC-XR had dimensions of about 0.3×0.2×0.2 mm. Form A proved to be stable (XRPD) on heating at 40° C., 85% RH, for 7 days. The SC-XR determination was performed at room temperature, using an Oxford Xcalibur S radiation Mo-K refractometer, λ=0.71073 Å with a graphite monochromator and a Sapphire CCD detector.

EXAMPLE 51

Solubility of Form A

The sample of 6-(1H-imidazol-1-yl)-2-phenylquinazoline fumarate form A, is stirred in an aqueous solution of NaCl 0.9%, at 500 rpm, so as to obtain a suspension (100 mg in 4 mL), for 24 hours at 37° C. The suspension is then filtered and the concentration of the dissolved product is measured by reading the UV absorbance at 260 nm. The solubility is 1.2 mg/mL. The dissolution rate is measured by adding 2 mg of product to 40 mL of water at 37° C., stirring at 500 rpm, and measuring the absorbance at 260 nm every 0.05 min; the dissolution rate is found to be $2.67 \times 10^{-5}$ gr/min.

EXAMPLE 52

Preparation of 6-(1H-imidazol-1-yl)-2-phenylquinazoline maleate (maleate salt form A), method 1

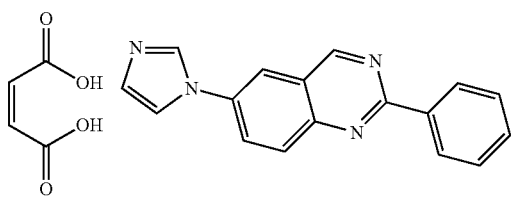

6-(1H-Imidazol-1-yl)-2-phenylquinazoline, 2.7 g (0.01 mol), is dissolved in 65 mL of acetone at reflux with stirring, a hot solution of 1.16 g (0.01 mol) of maleic acid in acetone (13 mL) is added, the mixture is then allowed to cool to room temperature, the resulting suspension is stirred at room temperature overnight, and the mixture is then filtered and the product is washed with acetone and dried at 60° C., 20 mmHg, for 12 hours. 2.68 g (69%) of non-hygroscopic product are obtained, XRPD form A. KF<0.5%. Calculated for $C_{17}H_{12}N_4.C_4H_4O_4$: C, 64.94; H, 4.15; N, 14.43. found: C, 64.51; H, 4.20; N, 14.45; H-NMR (d$_6$-DMSO) δ: 9.74 (s, 1H), 8.83 (s, 1H), 8.59-8.71 (m, 2H), 8.51 (d, 1H), 8.42 (d, 1H), 8.09 (s, 1H), 7.61-7.58 (m, 3H), 7.59 (s, 1H), 6.19 (s, 2H).

EXAMPLE 53

Preparation of 6-(1H-imidazol-1-yl)-2-phenylquinazoline maleate (maleate salt form A), method 2

6-(1H-Imidazol-1-yl)-2-phenylquinazoline, 2.7 g (0.01 mol) are dissolved in EtOH (75 mL) at reflux with stirring, 1.16 g (0.01 mol) of maleic acid are then added, the mixture is stirred for 30 min. and is then allowed to cool to room temperature, and the resulting solution is stirred at room temperature overnight and then filtered, washed with a small amount of EtOH and dried at 60° C., 20 mmHg, for 12 hours. 2.4 g (62%) of non-hygroscopic product are obtained, XRPD form A. KF<0.5%. Form A may similarly be prepared from methanol, isopropanol or acetonitrile. The crystal for determination of the cell structure (SC-XR) was obtained in a similar manner by dissolving 68 mg of 6-(1H-imidazol-1-yl)-2-phenylquinazoline maleate in boiling EtOH (4 mL), and the mixture is then left to evaporate slowly at room temperature and atmospheric pressure, to obtain a few crystals. The one used for SC-XR had dimensions of about 0.2×0.08×0.08 mm.

EXAMPLE 54

Preparation of 6-(1H-imidazol-1-yl)-2-phenylquinazoline maleate (maleate salt form A), method 3

6-(1H-Imidazol-1-yl)-2-phenylquinazoline, 5.44 g (0.021 mol), is dissolved in a 1/1 mixture of isopropyl acetate/isopropyl alcohol (75 mL) at reflux, with stirring, 2.9 g (0.025 mol) of maleic acid are added, the mixture is stirred for 15 min. and is allowed to cool to room temperature, and the resulting solution is stirred at room temperature overnight and then filtered, washed with isopropyl acetate and dried at 60° C., 20 mmHg, for 12 hours. 5.5 g (77%) of non-hygroscopic product are obtained, XRPD form A. KF<0.5%. Form A may similarly be prepared from mixtures of ethanol with ethyl acetate, or methyl acetate, or DCM, or THF, or methyl ethyl ketone, or dioxane.

EXAMPLE 55

Preparation of
6-(1H-imidazol-1-yl)-2-phenylquinazoline maleate
(maleate salt form A), method 4

6-(1H-Imidazol-1-yl)-2-phenylquinazoline, 147 g (0.54 mol), is dissolved in a mixture of acetone (3.5 L) and methanol (350 mL) at reflux, the mixture is filtered while hot with stirring at 30° C., 59.7 g (0.514 mol) of maleic acid are added, the resulting mixture is dissolved in hot acetone (300 mL), it is stirred for 30 min. at 40° C., and is then allowed to cool to room temperature, and the resulting suspension is stirred at room temperature overnight, and then filtered, washed with cold acetone (200 mL) and dried at 60° C., 20 mmHg, for 12 hours. 180 g (98%) of non-hygroscopic product are obtained, XRPD form A. KF<0.5%. Form A heated at 40° C., 70% RH for 7 days is stable (XRPD), as it is when heated at 90° C. for 12 hours.

EXAMPLE 56

Stability of Form A to Mechanical Stress (Milling)

6-(1H-Imidazol-1-yl)-2-phenylquinazoline maleate, form A, was subjected to milling by means of a Retsch MM 200 mill, at 50 Hz for 5 min., and the product thus obtained was subjected to XRPD analysis. The diffractogram obtained shows that form A has not undergone any changes of crystalline form, but a slight increase in the presence of amorphous product is revealed, which recrystallizes within a few hours on standing.

EXAMPLE 57

Stability of Form A to Moisture

The sample of 6-(1H-imidazol-1-yl)-2-phenylquinazoline maleate, form A, was subjected to DVS analysis. The change is given in FIG. 50. It is noted that the product is not hygroscopic in the range 0-85% RH, and similarly is not particularly hygroscopic even at values of greater than 85% RH.

EXAMPLE 58

Solubility of Form A

The sample of 6-(1H-imidazol-1-yl)-2-phenylquinazoline maleate, form A, is stirred in an aqueous solution of NaCl 0.9%, at 500 rpm, so as to obtain a suspension (150 mg in 4 mL), for 24 hours at 37° C. The suspension is then filtered and the concentration of the dissolved product is measured by reading the UV absorbance at 260 nm. The solubility is 7.9 mg/mL. The dissolution rate is measured by adding 2 mg of product to 40 mL of water at 37° C., stirring at 500 rpm, and measuring the absorbance at 260 nm every 0.05 min; the dissolution rate is found to be $1.45 \times 10^{-3}$ gr/min.

EXAMPLE 59

Bioavailability of Form A

The pharmacokinetics of 6-(1H-imidazol-1-yl)-2-phenylquinazoline maleate, form A, were evaluated in rats, as described in Example 8. The pharmacokinetic parameters measured are summarized hereinbelow: it is noted that the salt under consideration has optimum bioavailability (F %).

| PK parameters for 6-(1H-imidazol-1-yl)-2-phenylquinazoline maleate form A | | | | |
|---|---|---|---|---|
| Route | T½ (min). | V L/Kg | CL (L/Kg/min) | F (%) |
| IV | 45.6 | 1.3 | 0.022 | — |
| OS | 44.97 ($T_{max}$: 60 min) | 1.90 | 0.016 | 100 |

EXAMPLE 60

Preparation of
6-(1H-imidazol-1-yl)-2-phenylquinazoline maleate,
form A/B 6-(1H-Imidazol-1-yl)-2-phenylquinazoline, 136 mg (0.5 mmol), is dissolved in a mixture of isopropanol (15 mL) and water (0.5 mL) at reflux, with stirring at 50° C., 60 mg (0.5 mmol) of maleic acid are added, the mixture is stirred for 30 min. at 40° C., and then cooled to 0° C., and the resulting suspension is stirred at 0° C. a few minutes, filtered, washed with cold isopropanol and dried at 30° C., 20 mmHg, for 5 hours. 120 mg of product are obtained, XRPD: form A+form B as in FIG. 51.

EXAMPLE 61

Preparation of
6-(1H-imidazol-1-yl)-2-phenylquinazoline maleate
(maleate salt form B)

6-(1H-Imidazol-1-yl)-2-phenylquinazoline, 136 mg (0.5 mmol), is dissolved in a mixture of isopropanol (15 mL) and water (0.5 mL) at reflux, 60 mg (0.5 mmol) of maleic acid are added, the mixture is stirred for 30 min. at 40° C., and is then allowed to cool to room temperature and is left to stand for 3 days while allowing the solution to evaporate slowly, and the resulting material is filtered, washed with cold isopropanol and dried at 30° C., 20 mmHg, for 5 hours. 180 mg of product are obtained, XRPD: Form B. KF: 2.03%. Form B heated at 40° C., RH 85% for 7 days is partially converted into form A (XRPD). Form B heated at 90° C. for 12 hours is converted into form A.

EXAMPLE 62

Preparation of 6-(1H-imidazol-1-yl)-2-phenylquinazoline phosphate, form A

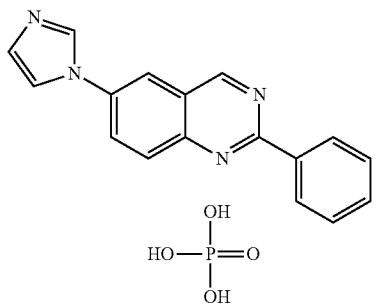

6-(1H-Imidazol-1-yl)-2-phenylquinazoline, 275 mg (1 mmol), is dissolved in EtOH (15 mL) at reflux, 100 mg (1 mmol) of phosphoric acid are added, the mixture is stirred for 30 min., and is then allowed to cool to room temperature and left to stand for 3 days while allowing the solution to evaporate slowly, and the resulting material is filtered and dried at 30° C., 20 mmHg, for 8 hours. 270 mg of product are obtained, XRPD: Form A. TGA: no weight loss up to 250° C. Calculated for $C_{17}H_{12}N_4 \cdot H_3PO_4$: C, 48.59; H, 4.13; N, 15.84. found: C, 57.22; H, 4.22; N, 15.84; H-NMR (d$_6$-DMSO) δ: 9.72 (s, 1H), 8.60-8.50 (m, 2H), 8.48 (d, 1H), 8.41 (d, 1H), 8.23 (d, 1H), 8.21 (s, 1H), 7.98-7.58 (m, 3H), 7.22 (s, 1H).

EXAMPLE 63

Solubility of Form A

The sample of 6-(1H-imidazol-1-yl)-2-phenylquinazoline phosphate, form A, is stirred in an aqueous solution of NaCl 0.9%, at 500 rpm, so as to obtain a suspension (50 mg in 2 mL), for 24 hours at 37° C. The suspension is then filtered and the concentration of the dissolved product is measured by reading the UV absorbance at 260 nm. The solubility is 6.2 mg/mL. The dissolution rate is measured by adding 2 mg of product to 40 mL of water at 37° C., stirring at 500 rpm, and measuring the absorbance at 260 nm every 0.05 min; the dissolution rate is found to be $1.73 \times 10^{-4}$ gr/min.

EXAMPLE 64

Preparation of 6-(1H-imidazol-1-yl)-2-phenylquinazoline oxalate, form A

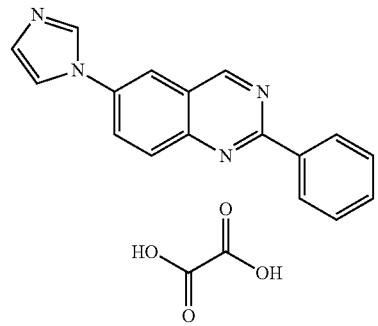

6-(1H-Imidazol-1-yl)-2-phenylquinazoline, 275 mg (1 mmol), is dissolved in EtOH (15 mL) at reflux, 90 mg (1 mmol) of oxalic acid are added, the mixture is stirred for 30 min. and is then allowed to cool to room temperature and is left to stand for 3 days while allowing the solution to evaporate slowly, and the resulting material is filtered and dried at 30° C., 20 mmHg, for 8 hours. 180 mg of product are obtained, XRPD: Form A. TGA: no weight loss up to 230° C. H-NMR (d$_6$-DMSO) δ: 9.73 (s, 1H), 8.60-8.58 (m, 2H), 8.48 (d, 1H), 8.43 (d, 1H), 8.24 (d, 1H), 8.00 (s, 1H), 7.60-7.58 (m, 3H), 7.24 (s, 1H).

EXAMPLE 65

Solubility of Form A

The sample of 6-(1H-imidazol-1-yl)-2-phenylquinazoline phosphate, form A, is stirred in an aqueous solution of NaCl 0.9%, at 500 rpm, so as to obtain a suspension (70 mg in 2 mL), for 24 hours at 37° C. The suspension is then filtered and the concentration of the dissolved product is measured by reading the UV absorbance at 260 nm. The solubility is 3.6 mg/mL. The dissolution rate is measured by adding 2 mg of product to 40 mL of water at 37° C., stirring at 500 rpm, and measuring the absorbance at 260 nm every 0.05 min; the dissolution rate is found to be $1.9 \times 10^{-4}$ gr/min.

Pharmaceutical Formulations

The compounds of the invention described above may be used for the preparation of pharmaceutical formulations that may be administered orally or parenterally. For all the formulations discussed herein, the compound will be administered in the treatment of the indicated pathologies, in an amount preferably of between about 0.1 and about 20 mg/kg, the optimum amount and the number of daily administrations being determined by the nature and severity of the treated pathology.

The present invention also includes pharmaceutical preparations containing a pharmacologically active amount of a compound of the invention in combination with suitable dispersants, lubricants and/or solvents.

The compounds of the invention may be prepared in various oral pharmaceutical forms such as: capsules, tablets, pills, granules. Appropriate dispersants and lubricants for such formulations include, but are not limited to: magnesium carbonate, magnesium stearate, talc, lactose, methylcellulose, sodium carboxymethylcellulose. The techniques used for preparing such formulations include mixing of the active principle with the dispersants, granulation and compression, or the filling of capsules.

The compounds of the invention may be formulated for parenteral administration in the form of prefilled vials or syringes. The active principle may be dissolved in an aqueous vehicle or may be in the form of an oily emulsion.

The invention claimed is:

1. A crystalline form of 6-(1H-imidazol-1-yl)-2-phenylquinazoline hydrochloride, having one or more of the following features:
   i) an X-ray powder diffraction spectrum (XRPD) as shown in FIG. 20 and/or comprising the main peaks at diffraction angles (2θ°) 4.72, 9.36, 10.37, 14.69, 18.34, 20.76, and 21.87; and
   ii) a melting point with decomposition at about 240° C.

2. A crystalline form of 6-(1H-imidazol-1-yl)-2-phenylquinazoline (L)-tartrate, form D, having one or more of the following features:
   i) an X-ray powder diffraction spectrum (XRPD) as shown in FIG. 41 and/or comprising the main peaks at diffraction angles (2θ°) 9.60, 9.98, 11.47, 12.44, 17.37, 18.75, 18.99, 19.21, and 19.56;
   ii) a DSC thermogram with endothermic effect at about 189° C., as shown in FIG. 42; and
   iii) an FT-IR spectrum as shown in FIG. 43.

3. A crystalline form of 6-(1H-imidazol-1-yl)-2-phenylquinazoline maleate, comprising a triclinic system with cell parameters a=8.9412 (5) Å, b=9.8081 (5) Å, c=10.5922 (6) Å, α: 90.517° (4), β=101.969° (5), γ=99.132° (4), V=896.34 (8) Å$^3$, space group P-1, having one or more of the following features:
   i) an X-ray powder diffraction spectrum (XRPD) as shown in FIG. 47 and/or comprising the main peaks at diffraction angles (2θ°) 8.77, 9.31, 12.05, 12.38, 12.75, 15.89, 18.49, 20.05, 25.91, and 27.29;
   ii) a DSC thermogram with an endothermic effect with onset at about 156° C. and a second endothermic effect with onset at about 243° C., as shown in FIG. 48; and
   iii) an FT-IR spectrum as shown in FIG. 49.

4. A hemihydrated crystalline form of 6-(1H-imidazol-1-yl)-2-phenylquinazoline maleate, having one or more of the following features:
   i) an X-ray powder diffraction spectrum (XRPD) as shown in FIG. 50 and/or comprising the main peaks at diffraction angles (2θ°) 8.77, 9.31, 12.05, 12.38, 12.75, 15.89, 18.49, 20.05, 25.91, and 27.29;
   ii) a DSC thermogram as shown in FIG. 51, which shows an endothermic event with peak at about 83° C., and an endothermic event with onset at about 153° C. and an endothermic event with onset at about 228° C.; and
   iii) an FT-IR spectrum as shown in FIG. 52.

5. A crystalline form of 6-(1H-imidazol-1-yl)-2-phenylquinazoline fumarate, comprising a monoclinic system with cell parameters a=10.7980 (8) Å, b=11.6643 (7) Å, c=13.0888 (11) Å, α: 90°, β=106.842° (8), γ=90°, V=1577.8 (2) Å$^3$, space group P21/c, having one or more of the following features:
   i) an X-ray powder diffraction spectrum (XRPD) as shown in FIG. 44 and/or comprising the main peaks at diffraction angles (2θ°) 15.22, 16.85, 17.54, 17.96, 22.64, 25.90, and 26.72;
   ii) a DSC thermogram with endothermic effect with onset at about 199° C., endothermic effect with onset at about 200° C., and a third endothermic effect with onset at about 240° C., as shown in FIG. 45; and
   iii) an FT-IR spectrum as shown in FIG. 46.

6. A crystalline form of 6-(1H-imidazol-1-yl)-2-phenylquinazoline phosphate, having one or more of the following features:
   i) an X-ray powder diffraction spectrum (XRPD) as shown in FIG. 53 and/or comprising the main peaks at diffraction angles (2θ°) 4.40, 9.96, 10.82, 13.18, 16.43, 19.98, 20.42, 26.22; and
   ii) a melting point of 242-246° C.

* * * * *